United States Patent
Ng et al.

(10) Patent No.: US 10,543,333 B2
(45) Date of Patent: Jan. 28, 2020

(54) MASK VENT

(71) Applicant: ResMed Pty Ltd, Bella Vista, New South Wales (AU)

(72) Inventors: Eva Ng, Sydney (AU); Robert Henry Frater, Sydney (AU); Lee James Veliss, Rotterdam (NL); Barton John Kenyon, Sydney (AU); Daniel Robert Judson, Blue Mountains (AU); Robert Edward Henry, Sydney (AU); Alison Oldenburg, Sydney (AU); Renee Frances Flower, Sydney (AU); Michael John Reid, Sydney (AU)

(73) Assignee: ResMed Pty Ltd, Bella Vista (AU)

(*) Notice: Subject to any disclaimer, the term of this patent is extended or adjusted under 35 U.S.C. 154(b) by 0 days.

(21) Appl. No.: 15/837,100

(22) Filed: Dec. 11, 2017

(65) Prior Publication Data

US 2018/0104431 A1    Apr. 19, 2018

Related U.S. Application Data

(63) Continuation of application No. 14/475,941, filed on Sep. 3, 2014, now abandoned, which is a continuation (Continued)

(51) Int. Cl.
*A61M 16/06* (2006.01)
*A61M 16/08* (2006.01)
(Continued)

(52) U.S. Cl.
CPC ...... *A61M 16/0666* (2013.01); *A61M 16/009* (2013.01); *A61M 16/0057* (2013.01);
(Continued)

(58) Field of Classification Search
CPC .......... A61M 16/0666; A61M 16/1065; A61M 16/0057; A61M 16/0066; A61M 16/009;
(Continued)

(56) References Cited

U.S. PATENT DOCUMENTS

| 2,241,535 A | 5/1941 | Boothby |
| 2,944,547 A | 7/1960 | Ziherl et al. |

(Continued)

FOREIGN PATENT DOCUMENTS

| DE | 103 31 134 | 3/2005 |
| EP | 0 697 225 | 2/1996 |

(Continued)

OTHER PUBLICATIONS

First Examination Report dated Oct. 24, 2017 issued in New Zealand Application No. 735401 (3 pages).

(Continued)

*Primary Examiner* — Kendra D Carter
*Assistant Examiner* — Jonathan S Paciorek
(74) *Attorney, Agent, or Firm* — Nixon & Vanderhye P.C.

(57) ABSTRACT

A vent arrangement is provided to a mask or associated conduit to discharge exhaled gas from the mask to atmosphere. The vent arrangement is structured to diffuse the exhaust vent flow to produce less air jetting, thereby increasing the comfort of the patient and their bed partner. For example, the vent arrangement may include one or more grill components and/or media constructed and arranged to diffuse vent flow.

18 Claims, 59 Drawing Sheets

Related U.S. Application Data of application No. 13/773,846, filed on Feb. 22, 2013, now Pat. No. 8,851,075, which is a continuation of application No. 12/230,120, filed on Aug. 22, 2008, now Pat. No. 8,397,727.

(60) Provisional application No. 61/129,253, filed on Jun. 13, 2008, provisional application No. 61/064,405, filed on Mar. 4, 2008, provisional application No. 60/957,766, filed on Aug. 24, 2007.

(51) Int. Cl.
*A61M 16/10* (2006.01)
*A61M 16/00* (2006.01)
*A61M 16/20* (2006.01)

(52) U.S. Cl.
CPC ........ *A61M 16/0066* (2013.01); *A61M 16/06* (2013.01); *A61M 16/08* (2013.01); *A61M 16/0816* (2013.01); *A61M 16/0875* (2013.01); *A61M 16/1055* (2013.01); *A61M 16/1065* (2014.02); *A61M 16/208* (2013.01); *A61M 2202/0085* (2013.01); *A61M 2202/0225* (2013.01); *A61M 2205/0238* (2013.01); *A61M 2205/42* (2013.01)

(58) Field of Classification Search
CPC .. A61M 16/06; A61M 16/08; A61M 16/0816; A61M 16/0875; A61M 16/1055; A61M 16/208; A61M 2202/0085; A61M 2202/0225; A61M 2205/0238; A61M 2205/42
See application file for complete search history.

(56) References Cited

U.S. PATENT DOCUMENTS

| | | |
|---|---|---|
| 4,501,271 A | 2/1985 | Clifton et al. |
| 4,784,129 A | 11/1988 | Garrafa |
| 4,919,128 A | 4/1990 | Kopala |
| 4,981,134 A | 1/1991 | Courtney |
| 4,989,596 A | 2/1991 | Macris et al. |
| 5,117,821 A | 6/1992 | White |
| 5,372,130 A | 12/1994 | Stern et al. |
| 5,438,981 A | 8/1995 | Starr et al. |
| 5,558,466 A | 9/1996 | Kuo et al. |
| 5,560,354 A | 10/1996 | Berthon-Jones et al. |
| 5,647,357 A | 7/1997 | Barnett et al. |
| 5,657,752 A | 8/1997 | Landis et al. |
| 5,662,101 A | 9/1997 | Ogden et al. |
| D387,734 S | 12/1997 | Hawkins et al. |
| 5,746,201 A | 5/1998 | Kidd |
| 5,896,857 A | 4/1999 | Hely et al. |
| 5,937,851 A | 8/1999 | Serowski et al. |
| 6,123,071 A | 9/2000 | Berthon-Jones et al. |
| 6,125,849 A | 10/2000 | Williams et al. |
| 6,460,539 B1 | 10/2002 | Japuntich et al. |
| 6,581,594 B1* | 6/2003 | Drew .............. A61M 16/06 128/204.18 |
| 6,584,977 B1 | 7/2003 | Serowski |
| 6,662,803 B2 | 12/2003 | Gradon et al. |
| 6,691,707 B1 | 2/2004 | Gunaratnam et al. |
| 6,851,425 B2 | 2/2005 | Jaffre et al. |
| 6,907,882 B2* | 6/2005 | Ging .............. A61M 16/06 128/202.27 |
| 7,066,178 B2 | 6/2006 | Gunaratnam et al. |
| D535,023 S | 1/2007 | Smart et al. |
| 7,267,120 B2 | 9/2007 | Rustad et al. |
| 7,316,230 B2* | 1/2008 | Drew .............. A61M 16/06 128/202.27 |
| 7,341,060 B2* | 3/2008 | Ging .............. A61M 16/06 128/206.11 |
| D580,048 S | 11/2008 | Guney et al. |
| D594,113 S | 6/2009 | Reid et al. |
| D612,481 S | 3/2010 | Reid et al. |
| 7,836,886 B2 | 11/2010 | McDonald et al. |
| 7,861,713 B2 | 1/2011 | Dhuper et al. |
| 7,913,692 B2 | 3/2011 | Kwok |
| 8,397,727 B2 | 3/2013 | Ng et al. |
| 8,439,035 B2 | 5/2013 | Dantanarayana et al. |
| 8,678,003 B2 | 3/2014 | Darkin et al. |
| 8,851,075 B2 | 10/2014 | Ng et al. |
| 2003/0005931 A1 | 1/2003 | Jaffre et al. |
| 2004/0025881 A1* | 2/2004 | Gunaratnam ......... A61M 16/06 128/206.15 |
| 2004/0094157 A1 | 5/2004 | Dantanarayana et al. |
| 2004/0103899 A1 | 6/2004 | Noble |
| 2004/0226566 A1 | 11/2004 | Gunaratnam |
| 2006/0266365 A1 | 11/2006 | Stallard |
| 2007/0062536 A1 | 3/2007 | McAuley et al. |
| 2009/0050156 A1 | 2/2009 | Ng |
| 2011/0061655 A1 | 3/2011 | McDonald et al. |
| 2011/0120457 A1 | 5/2011 | Dhuper et al. |
| 2011/0180071 A1 | 7/2011 | Veliss et al. |
| 2013/0160769 A1 | 6/2013 | Ng et al. |
| 2014/0366882 A1 | 12/2014 | Ng et al. |
| 2017/0291004 A1 | 10/2017 | Ng et al. |

FOREIGN PATENT DOCUMENTS

| | | |
|---|---|---|
| EP | 0 958 841 | 11/1999 |
| JP | 2004-535226 | 11/2004 |
| JP | 2005-537906 | 12/2005 |
| JP | 2009-50707 | 3/2009 |
| WO | WO 98/34665 | 8/1998 |
| WO | WO 1998/34665 | 8/1998 |
| WO | WO 98/48879 | 11/1998 |
| WO | WO 00/78382 | 12/2000 |
| WO | WO 2002/051486 | 7/2002 |
| WO | WO 2002/096342 | 12/2002 |
| WO | 2005/051468 A1 | 6/2005 |
| WO | WO 2005/051468 | 6/2005 |
| WO | WO 2006/024288 | 3/2006 |
| WO | WO 2006/069415 | 7/2006 |
| WO | WO 2006/074516 | 7/2006 |
| WO | WO 2006/096924 | 9/2006 |
| WO | WO 2006/122369 | 11/2006 |
| WO | WO 2007/012140 | 2/2007 |
| WO | WO 2007/012145 | 2/2007 |

OTHER PUBLICATIONS

First Office Action issued in corresponding Japanese Application No. 2014-160191 dated Aug. 24, 2015, with English translation thereof.
Communication pursuant to Article 94(3) EPC issued in corresponding European Application No. 11 181 712.8 dated Apr. 26, 2016.
Second Office Action issued in corresponding Japanese Application No. 2014-160191 dated Apr. 18, 2016 with English translation thereof.
Further Examination Report issued in corresponding New Zealand Patent Application No. 718484 dated Jul. 5, 2016.
Statement of Case dated Oct. 28, 2016 filed in New Zealand Application No. 701093 (11 pages).
Office Action dated Dec. 21, 2016 issued in European Application No. 11181712.8 (4 pages).
Office Action dated Dec. 19, 2016 issued in Japanese Application No. 2014-160191 with English translation (5 pages).
Extension of Time Granted dated Aug. 31, 2016, together with a Notice of Opposition to Grant of Patent (Section 21) filed on Aug. 29, 2016 by Fisher & Paykel Healthcare Limited in corresponding New Zealand Application No. 701093 (3 pages).
U.S. Appl. No. 10/585,091 (2007-0267023), filed Dec. 2004 (Nov. 2007), Ging et al.
U.S. Appl. No. 11/027,689 (2005-0172969), filed Jan. 2005 (Aug. 2005), Ging et al.
U.S. Appl. No. 11/878,932 (2008/0060649), filed Jul. 2007 (Mar. 2008), Veliss et al.

(56) References Cited

OTHER PUBLICATIONS

U.S. Appl. No. 11/878,933 (2008/0047560), filed Jul. 2007 (Feb. 2008), Veliss et al.
U.S. Appl. No. 11/952,167 (2008-0087287), filed Dec. 2007 (Apr. 2008), Ging et al.
U.S. Appl. No. 60/924,359, filed May 2007, Davidson et al.
European Search Report, Appln. No. 08162863, dated Nov. 17, 2008, 7 pages.
Extended European Search Report issued in Ep Appln. No. 11181712.8 dated Jan. 24, 2012.
Chinese Office Action issued in related Application No. 200810210534.1 dated Mar. 15, 2012.
Office Action issued in a corresponding Japanese Application No. 2008-215721 dated Dec. 21, 2012, with English translation thereof.
Further Examination Report issued in corresponding New Zealand Appln. No. 599608 dated Mar. 13, 2013.
First Examination Report issued in corresponding New Zealand Appln. No. 610424 dated May 16, 2013.
Further Examination Report issued in corresponding New Zealand Appln. No. 599608 dated Aug. 22, 2013.
Notice of Reasons for Rejection issued in corresponding Japanese Appln. No. 2013-058108 dated Feb. 17, 2014, with English translation thereof.
Office Action dated Apr. 5, 2018 issued in U.S. Appl. No. 15/628,852 (35 pages).
Office Action dated Aug. 8, 2018 issued in U.S. Appl. No. 15/628,852 with Form PTO-892 citing U.S. Pat. No. 2,241,535 A, U.S. Pat. No. 4,919,128 A, U.S. Pat. No. 6,341,606 B1, U.S. Pat. No. 2004/0226566 A1, and U.S. Pat. No. 8,485,181 B2 (21 pages).
Amended Statement of Case (Clean and Track Changes), filed by Fisher & Paykel Healthcare Limited dated Feb. 7, 2019 in New Zealand Application No. 701093, 28 pages.

* cited by examiner

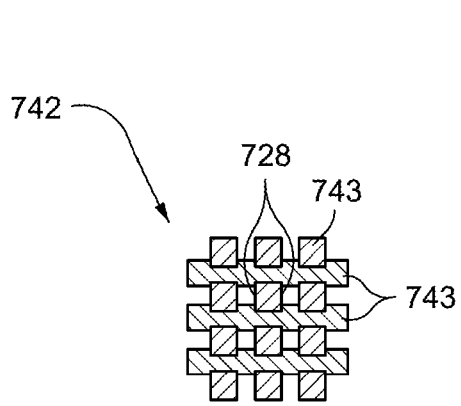
Fig. 2-8
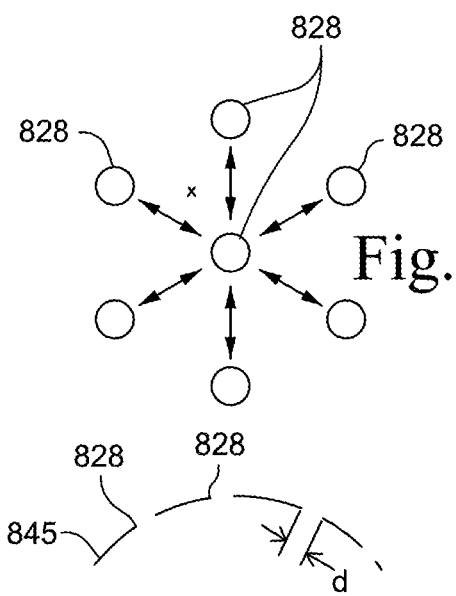
Fig. 2-9-2
Fig. 2-9-1
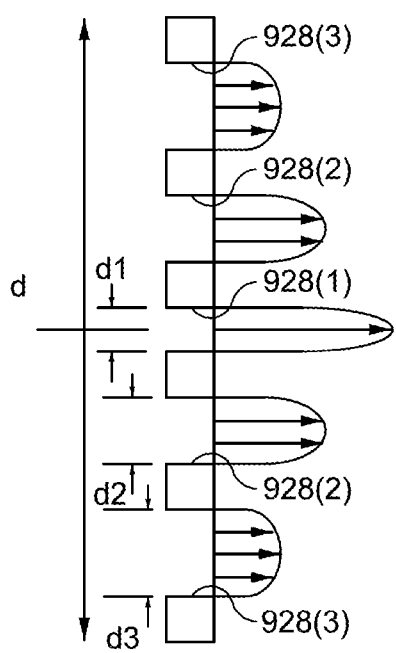
Fig. 2-10-2
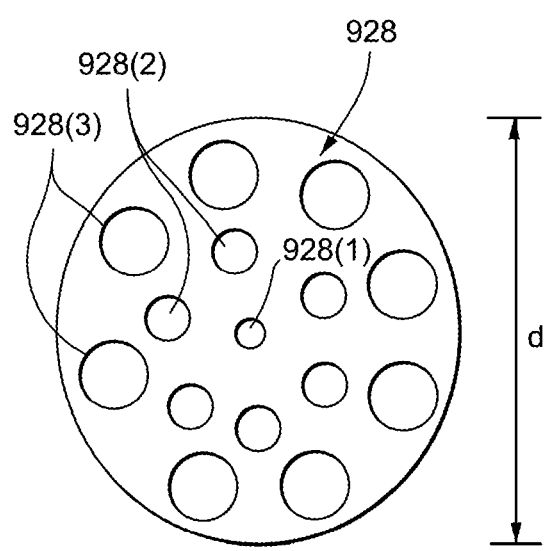
Fig. 2-10-1

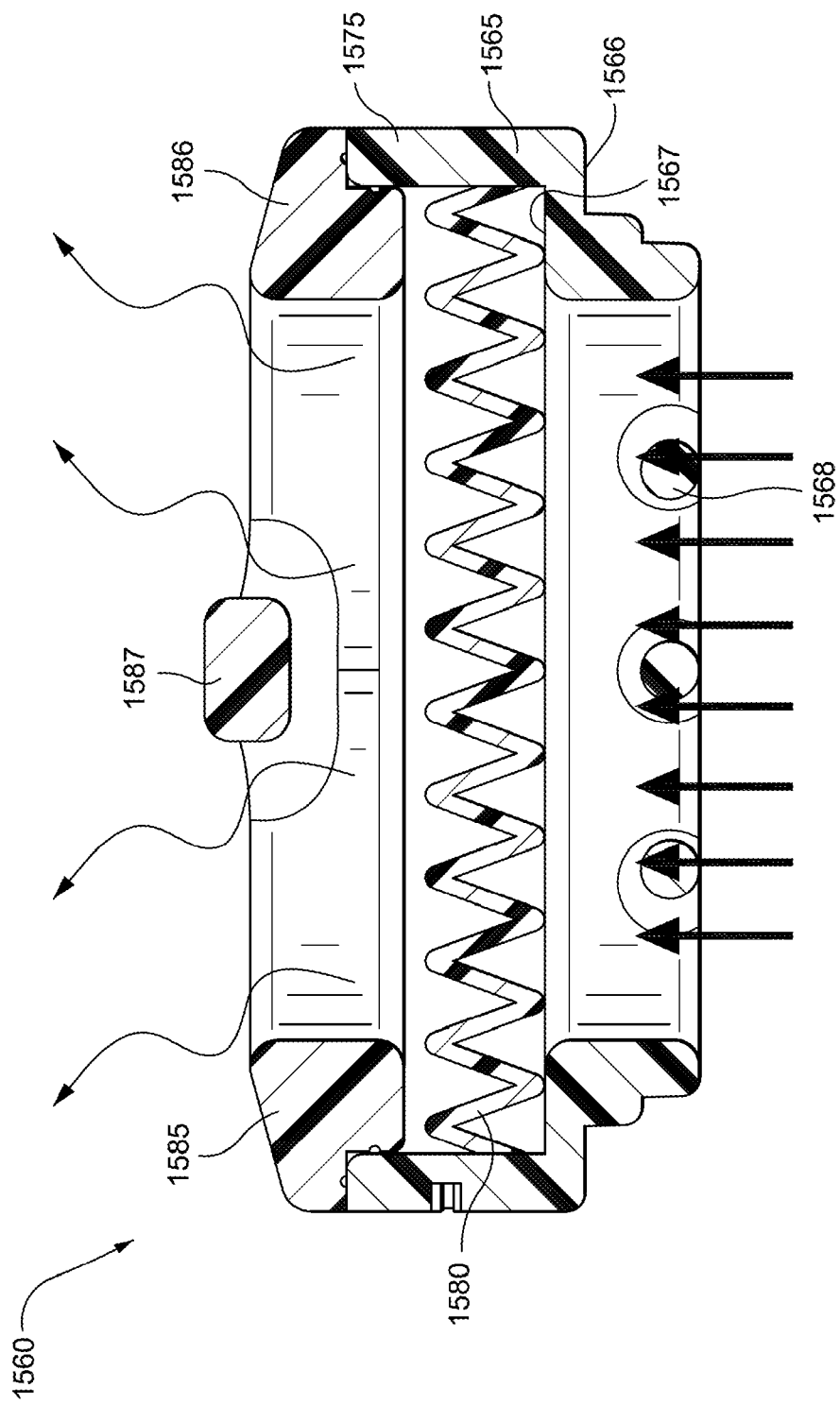

| Vent Material | Diameter (mm) | Unobstructed | | | | Obstructed | | |
|---|---|---|---|---|---|---|---|---|
| | | 10cmH2O | | 20cmH2O | | 10cmH2O | | |
| | | dBA | L/min | dBA | L/min | dBA | L/min | |
| Standard Vent with no material | | 26.6 | 28.1 | 34.4 | 42.0 | 31.8 | 28.1 | |
| Polypropelene mesh 1 | 15 | 24.7 | 24.9 | 32.0 | 38.5 | 24.5 | 24.9 | |
| Polypropelene mesh 2 | 15 | 23.0 | 14.6 | 28.2 | 23.7 | 22.7 | 14.6 | |
| Polypropelene mesh 3 | 15 | 23.5 | 19.1 | 29.7 | 30.6 | 23.8 | 19.1 | |
| Stainless steel mesh | 15 | 22.3 | 19.1 | | | 22.4 | 19.1 | |
| Woven wicking fabric | 10 | 34.2 | 28.1 | | | | | |
| Reticulated foam | 10 | 44.2 | 56.5 | | | | | |
| ePTFE membrane | 10 | 23.2 | 6.6 | | | | | |
| Non woven | 10 | 30.5 | 28.1 | | | | | |
| PET mesh 1 | 15 | 25.8 | 24.3 | | | | | |
| PET mesh 2 | 15 | 33.1 | 48.3 | | | | | |
| PET mesh 3 | 15 | 24.1 | 30.8 | | | | | |

Fig. 3

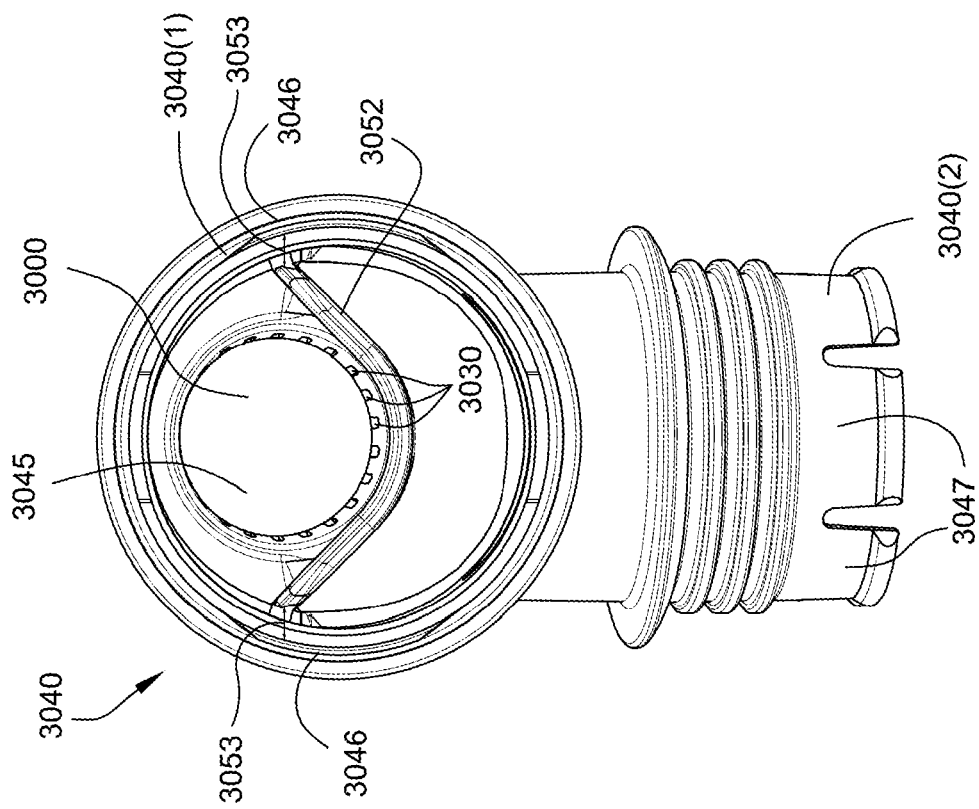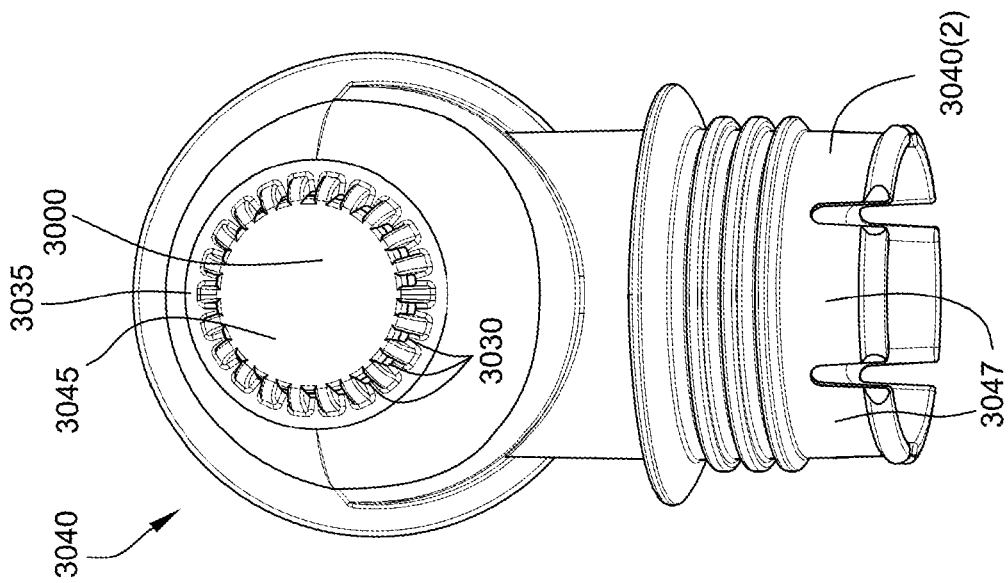

MASK VENT

CROSS-REFERENCE TO APPLICATION

This application is a continuation of U.S. patent application Ser. No. 14/475,941, filed Sep. 3, 2014, currently pending, which is a continuation of U.S. patent application Ser. No. 13/773,846, filed Feb. 22, 2013, now U.S. Pat. No. 8,851,075, which is a continuation of U.S. patent application Ser. No. 12/230,120, filed Aug. 22, 2008, now U.S. Pat. No. 8,397,727, which claims the benefit of U.S. Provisional Application Nos. 61/129,253, filed Jun. 13, 2008, 61/064,405, filed Mar. 4, 2008, and 60/957,766, filed Aug. 24, 2007, each of which is incorporated herein by reference in its entirety.

FIELD OF THE INVENTION

The field of the invention relates to mask vents used for Non-invasive Positive Pressure Ventilation (NPPV) and for continuous positive airway pressure (CPAP) therapy of sleep disordered breathing (SDB) conditions such as obstructive sleep apnea (OSA).

BACKGROUND OF THE INVENTION

Treatment of sleep disordered breathing (SDB), such as obstructive sleep apnea (OSA), by continuous positive airway pressure (CPAP) flow generator systems involves the continuous delivery of air (or other breathable gas) pressurized above atmospheric pressure to the airways of a human or other mammalian patient via a conduit and a mask. Typically, the mask fits over the mouth and/or nose of the patient. Pressurized air flows to the mask and to the airways of the patient via the nose and/or mouth. As the patient exhales, carbon dioxide gas may collect in the mask. A washout vent in the mask or conduit discharges the exhaled gas from the mask to atmosphere.

The washout vent is normally located in the mask or near the mask in the gas delivery conduit coupled to the mask. The washout of gas through the vent to the atmosphere removes exhaled gases to prevent carbon dioxide build-up, and hence "rebreathing", which represent a health risk to the mask wearer. Adequate gas washout is achieved by selecting a vent size and configuration that allows a minimum safe washout flow at a low operating CPAP pressure, which typically can be as low as 4 cm $H_2O$ for adults and 2 cm $H_2O$ for children.

Noise is a significant issue in CPAP treatment for the patient and/or the patient's bed partner. Excessive noise can lead to patients being non-compliant with the CPAP therapy. One source of noise is the exhaust through the vent in the mask or conduit. The flow of gas through the vent creates noise as it exits to and interacts with the atmosphere. Noise can adversely affect patient and bed-partner comfort, depending on both the magnitude and character of the noise. Further, bi-level gas delivery regimes tend to generate more noise than do constant level gas delivery regimes. This is thought to be due to the extra turbulence created by the gas accelerating and decelerating as it cycles between relatively low and relatively high pressures in the bi-level gas delivery systems.

"Air Jetting" out of the vents is also a significant issue. Air jetting, or lack of diffusion in the vent, involves a high-velocity jet stream of exhaust gases blowing onto obstacles (such as bedding, bed partner, or even onto the mask wearer themselves). This not only causes a significant increase in noise due to a sudden change in velocity of the exhausted air, but the high-velocity jet stream also creates great discomfort for the bed partner or mask wearer as a result of "wind chill".

Exemplary devices to reduce noise associated with gas washout are Respironics' Whisper Swivel II, Weinmann's SilentFlow 2, Weinmann's Noise Suppressor, ResMed MAP's Aero-Click, Fisher & Paykel's Aclaim 2, and Drager's E-Vent.

Other exemplary devices to reduce noise associated with gas washout are ResMed's Gore-Tex membrane vent, ResMed's stainless steel laser-cut orifices, and ResMed's Porex or sintered plastic vent. For example, see PCT Publication No. WO 2006/069415, published Jul. 6, 2006, which is incorporated herein by reference in its entirety.

There is a long felt and continuing need to reduce the noise associated with the washout or venting of exhaled gases. Reducing the noise of gas being exhausted from a mask or conduit can significantly improve the user friendliness of the CPAP treatment.

SUMMARY OF THE INVENTION

One aspect of the invention relates to a vent insert for a mask. The vent insert includes a base including one or more cross-bars and one or more grill components provided to the base. Each grill component includes a grill. The one or more grill components are stackable on top of the base and selectively rotatable with respect to the base to adjust the angle of the one or more grills of the one or more grill components with respect to the one or more cross-bars of the base so as to selectively define fine, porous vent orifices through the insert.

Another aspect of the invention relates a vent insert for a mask. The vent insert includes a base adapted to be supported within an outlet opening in the mask, one or more media provided to the base, and a cover including a cross-bar provided to the base to retain the at least one media within the base. The base includes one or more base cross-bars.

Another aspect of the invention relates to a mask including a mask component including a venting area having a plurality of vent orifices and a cover provided to the mask component. The cover includes a venting area having a plurality of vent clusters. Each vent cluster includes a tubular spigot that defines an orifice and a plurality of arcuate shaped orifices regularly spaced and separated from one another along a circle about the spigot. The cover is attachable to the mask component such that each vent cluster of the cover is aligned with a respective vent orifice of the mask component.

Another aspect of the invention relates to a mask including a mask component including a plurality of vent orifices and a cover provided to the mask component. The cover includes a plurality of vent clusters. Each vent cluster of the cover is aligned with a respective vent orifice of the mask component.

Another aspect of the invention relates to a mask including a mask component including a plurality of vent orifices and a cover provided to the mask component. The cover includes a plurality of vent orifices. Each orifice of the mask component corresponds to a plurality of orifices of the cover.

Another aspect of the invention relates to a mask assembly including a mask having a mask interior, an air delivery tube provided to the mask, and a shroud covering a portion of a length of the air delivery tube. The shroud and air delivery tube define a vent passage there between. The vent passage has an annular cross-section and including an inlet in communication with the mask interior and an outlet opening to atmosphere.

Another aspect of the invention relates to a mask assembly including an interfacing structure, a manifold positioned on a top of the patient's head and adapted to connect with a supply of breathable gas, and two inlet conduits extending along respective sides of the patient's face. The two inlet conduits are connected to the manifold and adapted to deliver the supply of breathable gas to the interfacing structure. Each inlet conduit and/or the manifold includes one or more vent orifices for gas washout.

Another aspect of the invention relates to a mask frame including a main body and a plurality of vent orifices distributed over a majority of the main body.

Another aspect of the invention relates to a vent arrangement for a mask including a mask component, at least one vent orifice provided to the mask component, each vent orifice including a vent exit, and a protrusion provided to the mask component adjacent each vent exit. The protrusion may be pyramidal, conical, or dome shaped. Such arrangement provides adjacent vent orifices adapted to deliver streams of exhaust gas that are substantially directionally perpendicular to each other.

Another aspect of the invention relates to a vent arrangement for a mask including a mask component and at least one vent orifice provided to the mask component. Each vent orifice has an hourglass shape including an inlet portion with a convergent configuration in which the orifice tapers from larger to smaller cross-section along its entire length and an outlet portion with a divergent configuration in which the orifice tapers from smaller to larger cross-section along its entire length. The inlet portion is continuous with the outlet portion, and the inlet portion and outlet portion include substantially similar lengths.

Another aspect of the invention relates to a mask including a mask frame including a mask interior, at least one vent orifice provided to the frame, and an obstruction provided within the mask interior and positioned in front of the at least one vent orifice.

Another aspect of the invention relates to a vent arrangement for a mask including a mask component and a mesh structure provided to the mask component. The mesh structure is woven to create a plurality of vent orifices. In an embodiment, the mesh structure includes stainless steel mesh or stainless steel wires. In an alternative embodiment, the mesh structure includes woven fabrics constructed of polypropylene, polycarbonate, polyamide, polyesters, polytetrafluoroethylene, or 3-dimensional spacer fabrics.

Another aspect of the invention relates to a vent arrangement for a mask including a mask component including a dome-shaped portion and a plurality of vent orifices provided to the dome-shaped portion. In an embodiment, the orifices include a central orifice and a plurality of orifices arranged in a circle about the central orifice.

Another aspect of the invention relates to a vent arrangement for a mask including a mask component and a plurality of vent orifices provided to the mask component. Adjacent vent orifices have a different diameter.

Another aspect of the invention relates to a vent insert for a mask including a sheet having a plurality of perforated sections. The perforated sections are adapted to be folded against each other to produce vent orifices through the perforated sections.

Another aspect of the invention relates to a vent arrangement for a mask. The vent arrangement includes a mask component and a plurality of adjacent protrusions provided to the mask component. Each of the protrusions includes one or more vent openings. The vent openings of the protrusions are arranged so that vent flow is directed in different directions, into one another, and/or slightly offset from one another to create diffuse air flow.

Another aspect of the invention relates to a vent arrangement for a mask. The vent arrangement includes a mask component and one or more protrusions provided to the mask component. Each of the protrusions includes a plurality of vent openings. The vent openings of each protrusion are arranged so that vent flow is directed in different directions, into one another, and/or slightly offset from one another to create diffuse air flow.

Another aspect of the invention relates to a vent arrangement for a mask. The vent arrangement includes a mask component and one or more recesses provided to the mask component. Each of the recesses includes a plurality of vent openings. The vent openings of the recesses are arranged so that vent flow is directed in different directions, into one another, and/or slightly offset from one another to create diffuse air flow.

Another aspect of the invention relates to a vent arrangement for a mask including a mask component and a vent cap provided to the mask component. The vent cap includes a base wall and a dome or raised portion that extends upwardly from the base wall. The dome or raised portion includes a side wall with multiple vent holes arranged along the side wall. The vent holes are open in use at least during the inhalation and exhalation phases of the user's breathing cycle.

Another aspect of the invention relates to a mask system including a mask, an elbow provided to the mask, and a baffle provided between the mask and the elbow. The elbow includes an annular side wall and a plurality of vent holes for gas washout arranged on the annular side wall. The baffle includes an annular configuration with one or more undulations and/or guides structured to guide washout gas along a flow path to the vent holes.

Another aspect of the invention relates to a mask system including a mask component including one or more openings for gas washout and a vent component provided to the mask component. The vent component includes one or more tracks or grooves along its outer surface adapted to guide gas washout. The vent component is adapted to cover the one or more openings in the mask component so that gas washout escapes along the one or more tracks or grooves between an outer surface of the mask component and the vent component.

Another aspect of the invention relates to a vent arrangement for a mask including a vent component adapted to be provided to the mask and at least partially define one or more openings for gas washout, and at least one port cap integrated with the vent component. Each port cap is adapted to engage a respective port provided to the mask.

Other aspects, features, and advantages of this invention will become apparent from the following detailed description when taken in conjunction with the accompanying drawings, which are a part of this disclosure and which illustrate, by way of example, principles of this invention.

BRIEF DESCRIPTION OF THE DRAWINGS

The accompanying drawings facilitate an understanding of the various embodiments of this invention. In such drawings:

FIG. 1-2 is a schematic view illustrating vent flow for a diffused vent having a branched outlet according to an embodiment of the present invention;

FIG. 2-1 is a schematic view of a mask including semi-remote venting according to an embodiment of the present invention;

FIGS. 2-2-1 and 2-2-2 are perspective views of a mask including venting along inlet conduits according to embodiments of the present invention;

FIGS. 2-3-1 and 2-3-2 are perspective views of a mask including venting at the top of the patient's head according to embodiments of the present invention;

FIG. 2-4 is a perspective view of a completely vented frame according to an embodiment of the present invention;

FIG. 2-5 is a schematic view of a mask including protrusions adjacent vent exits according to an embodiment of the present invention;

FIG. 2-6 is a schematic view of an hourglass-shaped vent orifice according to an embodiment of the present invention;

FIG. 2-7-1 is a perspective view illustrating flow through the vent inlet of ResMed's Mirage mask;

FIG. 2-7-2 is a perspective view illustrating an obstruction in front of a vent inlet according to an embodiment of the present invention;

FIG. 2-8 is a top view of a stainless steel mesh including vent orifices according to an embodiment of the present invention;

FIGS. 2-9-1 and 2-9-2 are schematic views of orifices distributed over a dome according to an embodiment of the present invention;

FIGS. 2-10-1 and 2-10-2 are schematic views of orifices defining different levels of velocity shrouds according to an embodiment of the present invention;

FIG. 2-11 is a schematic view of a slot-orifice vent according to an embodiment of the present invention;

FIG. 2-12 is a schematic graph illustrating a diameter range for an orifice to balance cleanability and quietness;

FIGS. 2-13-1 to 2-13-3 are schematic views of a foldable vent insert according to an embodiment of the present invention;

FIGS. 2-14-1 to 2-14-3 are various views of a stackable vent insert according to an embodiment of the present invention;

FIGS. 2-15-1 to 2-15-3 are various views of a vent insert including a single layer of media according to an embodiment of the present invention;

FIGS. 2-16-1 to 2-16-3 are various views of a vent insert including double layer media according to an embodiment of the present invention;

FIGS. 2-17-1 to 2-17-3 are various views of a vent insert including pleated media according to an embodiment of the present invention;

FIGS. 2-18-1 to 2-18-3 are various views of a vent insert as a common component according to an embodiment of the present invention;

FIG. 2-19 is a schematic view of a vent including a central higher-velocity stream and outer lower-velocity streams;

FIG. 2-20 is a schematic view of a dual flow mouthpiece for an air compressor demonstrating an application of the theory in FIG. 2-19;

FIGS. 2-21-1 to 2-21-4 are various views of an elbow assembly according to an embodiment of the present invention;

FIG. 2-22-1 illustrates a vent arrangement including a plurality of protrusions with vents according to another embodiment of the present invention;

FIG. 2-22-2 is a cross-sectional view of the vent arrangement shown in FIG. 2-22-1;

FIGS. 2-22-3 illustrates a vent arrangement including a plurality of protrusions with vents according to another embodiment of the present invention;

FIG. 2-22-4 is a cross-sectional view of the vent arrangement shown in FIG. 2-22-3;

FIG. 2-22-5 is a schematic view of a mold for molding the protrusions of FIGS. 2-22-3 and 2-22-4;

FIG. 2-23 is a cross-sectional view of a vent arrangement including a recess with vents according to another embodiment of the present invention;

FIG. 2-24 illustrates a vent arrangement including a plurality of dome-shaped protrusions with vents according to another embodiment of the present invention;

FIG. 2-25 illustrates a vent arrangement including a plurality of elongated three-dimensional trapezoidal-shaped protrusions with vents according to another embodiment of the present invention;

FIG. 2-26 illustrates a disk-like vent arrangement according to another embodiment of the present invention;

FIG. 3 is a chart illustrating sound power for vent media according to embodiments of the invention;

FIG. 4-1A is a top view of a vent cap according to an embodiment of the present invention;

FIG. 4-1B is a top view of a vent cap according to another embodiment of the present invention;

FIG. 4-1C is a top view of a vent cap according to another embodiment of the present invention;

FIGS. 4-2A to 4-2C are top, bottom, and side schematic views of the vent cap shown in FIG. 4-1B;

FIGS. 4-3A to 4-3C are top, side, and perspective views of the vent cap shown in FIG. 4-1B;

FIGS. 4-4A to 4-4B are perspective views of a vent cap according to another embodiment of the present invention;

FIGS. 4-5A to 4-5B are top and side views of an elbow according to an embodiment of the present invention;

FIGS. 4-6A to 4-6B are top and side schematic views illustrating an unlocked position of a vent cap with respect to an elbow according to an embodiment of the present invention;

FIGS. 4-7A to 4-7B are top and side schematic views illustrating a locked position of a vent cap with respect to an elbow according to an embodiment of the present invention;

FIG. 4-7C is a perspective view showing a vent cap on an elbow according to an embodiment of the present invention;

FIG. 4-7D is a perspective view showing a vent cap and elbow according to an embodiment of the present invention;

FIG. 5-1 is a schematic side view of a baffle provided between a mask and elbow according to an embodiment of the present invention;

FIG. 5-2 is a schematic plan view of a baffle according to an embodiment of the present invention;

FIG. 5-3-1 is an exploded view showing a baffle and elbow according to an embodiment of the present invention;

FIG. 5-3-2 is a cross-sectional view of the baffle and elbow shown in FIG. 5-3-1 in an assembled configuration;

FIG. 5-4 is a schematic view of a bayonet connection according to an embodiment of the present invention;

FIG. 5-5 is a schematic view of a bayonet connection according to another embodiment of the present invention;

FIG. 5-6-1 is a schematic side view of a coil-type baffle according to an embodiment of the present invention, the coil-type baffle in an uncoiled position;

FIG. 5-6-2 is a schematic side view of the coil-type baffle shown in FIG. 5-6-1 with the coil-type baffle in a coiled position;

FIGS. 5-7-1 and 5-7-2 are top and bottom perspective views of an elbow according to an embodiment of the present invention;

FIG. 5-8-1 is a perspective view of a baffle according to an embodiment of the present invention;

FIG. 5-8-2 is an exploded view showing a baffle and elbow according to an embodiment of the present invention;

FIG. 5-8-3 is a cross-sectional view of a baffle and elbow according to an embodiment of the present invention;

FIG. 5-9-1 is a perspective view of a vent ring and elbow according to another embodiment of the present invention;

FIG. 5-9-2 is a top view of the vent ring of FIG. 5-9-1;

FIG. 5-9-3 is a top view of the vent ring of FIG. 5-9-1 in a deformed position;

FIG. 5-9-4 is a perspective view showing assembly of the vent ring and elbow of FIG. 5-9-1;

FIG. 5-9-5 is a cross-sectional view of the assembled vent ring and elbow of FIG. 5-9-1;

FIG. 5-9-6 is a side view of the vent ring and elbow of FIG. 5-9-1;

FIG. 5-10-1 is a perspective view of a vent ring according to another embodiment of the present invention;

FIG. 5-10-2 is a perspective view showing assembly of the vent ring of FIG. 5-10-1 to an elbow;

FIG. 5-10-3 is an enlarged top view of the vent ring of FIG. 5-10-1;

FIG. 5-11-1 is a perspective view of a vent ring and elbow according to another embodiment of the present invention;

FIG. 5-11-2 is a perspective view showing the assembly of the vent ring and elbow of FIG. 5-11-1;

FIG. 5-12-1 is a perspective view of a vent ring and elbow according to another embodiment of the present invention;

FIG. 5-12-2 is a perspective view showing the assembly of the vent ring and elbow of FIG. 5-12-1;

FIGS. 6-1 to 6-7 are various views of an elbow including a vent arrangement according to another embodiment of the present invention;

FIG. 7-1 is a rear perspective view of a plug-type vent and frame according to another embodiment of the present invention;

FIG. 7-2 is a top perspective view of the plug-type vent and frame of FIG. 7-1;

FIG. 7-3 is a perspective view of the plug-type vent of FIG. 7-1;

FIG. 8-1 is a rear perspective view of a plug-type vent and frame according to another embodiment of the present invention;

FIG. 8-2 is a top perspective view of the plug-type vent and frame of FIG. 8-1;

FIG. 8-3 is a perspective view of the plug-type vent of FIG. 8-1;

FIG. 9-1 is a perspective view of a plug-type vent and frame according to another embodiment of the present invention;

FIG. 9-2 is an exploded view of the plug-type vent and frame of FIG. 9-1;

FIG. 9-3 is a perspective view of the plug-type vent of FIG. 9-1; and

FIG. 9-4 is a side view of the frame of FIG. 9-1.

DETAILED DESCRIPTION OF ILLUSTRATED EMBODIMENTS

The following description is provided in relation to several embodiments which may share common characteristics and features. It is to be understood that one or more features of any one embodiment may be combinable with one or more features of the other embodiments. In addition, any single feature or combination of features in any of the embodiments may constitute additional embodiments.

In this specification, the word "comprising" is to be understood in its "open" sense, that is, in the sense of "including", and thus not limited to its "closed" sense, that is the sense of "consisting only of". A corresponding meaning is to be attributed to the corresponding words "comprise", "comprised" and "comprises" where they appear.

The term "air" will be taken to include breathable gases, for example air with supplemental oxygen. It is also acknowledged that the PAP devices or blowers described herein may be designed to pump fluids other than air.

1. Mask Embodiments

A range of masks (also referred to as patient interfaces or mask systems) are known including nasal masks, nose & mouth masks, full-face masks and nasal prongs, pillows, nozzles & cannulae.

Masks typically include a rigid or semi-rigid portion (often referred to as a shell or frame) and a soft, patient contacting portion adapted to form a seal with the patient's nose and/or mouth (often referred to as a cushion or nasal prong arrangement). An elbow may be provided to the frame and adapted to be connected to an air delivery tube (not shown) that delivers breathable gas to the patient. However, it should be appreciated that other mask arrangements are possible, e.g., not rigid (e.g., constructed of cloth).

One or more washout vents are provided to the mask or associated conduit to discharge exhaled gas from the mask to atmosphere. In embodiments, the one or more vents may be provided to the frame and/or the elbow of the mask. One or more vents in the associated conduit is also possible.

2. Vent Embodiments

The following describes alternative embodiments of vent arrangements for gas washout from a mask.

It should be appreciated that each vent arrangement may be adapted for use with any suitable interface type, e.g., nasal masks, nose & mouth masks, full-face masks, nasal prongs, etc. In addition, each vent arrangement may be adapted for use in any suitable portion of the mask, e.g., frame, elbow, conduit, etc.

In an embodiment, the vent arrangement may be a common component structured for use in multiple interface types. For example, the vent arrangement may be adapted for use in a mask elbow, a mask frame for a full-face mask, and a frame for a nasal prong arrangement. Such an arrangement is described in greater detail below.

2.0 Diffused Vents

The vent arrangements described below may be structured to diffuse the exhaust vent flow. Increased diffusion of the exhaust vent flow may cause less air jetting onto bed clothes and bed partners, and may also produce less noise.

Figure 1:
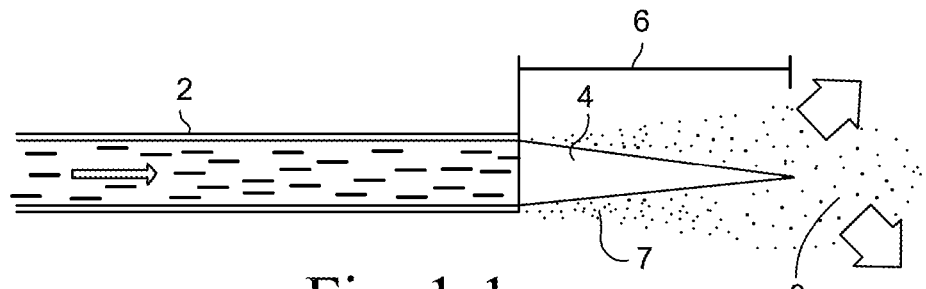
FIG. 1-1 is a schematic view illustrating vent flow for a single large outlet as known in the art.

For example, relatively large aperture vent orifices with relatively short flow path lengths produce high velocity, undeveloped flow which can generate excessive noise. FIG. 1-1 illustrates vent flow for a single large outlet 2. As illustrated, the exhaust vent flow produces a large core stream 4 with a large mixing area 6. High frequency noise is indicated at 7 and low frequency noise is indicated at 8.

Figures 1, 2:
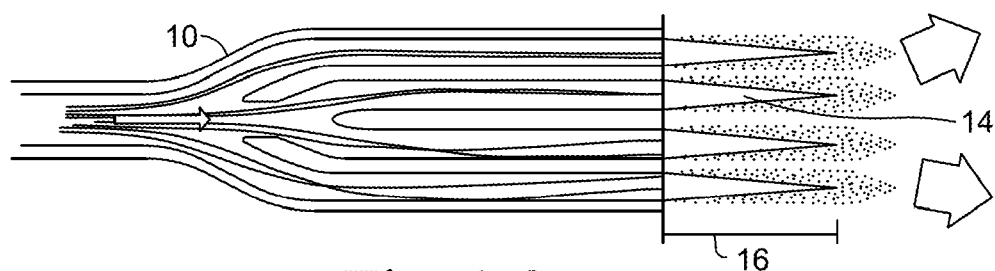

In contrast, FIG. 1-2 illustrates vent flow for a diffused vent having a branched outlet 10 according to an embodiment of the present invention. As illustrated, the core stream 14 and mixing area 16 is significantly smaller than that of the large outlet 2 of FIG. 1-1. In addition, the noise (e.g., high frequency noise from air streams contacting very low velocity ambient air streams) travels significantly less from the branched outlet 10 than that of the large outlet 2 of FIG. 1-1.

At a distance x from the outlet, the vent flow of outlet 2 has a higher velocity that produces more noise if the air flow is interrupted (e.g., by the patient's bed clothes) while the vent flow of branched outlet 10 has a lower velocity that produces less noise if the air flow is interrupted. Noise is caused by the sudden change in high velocity of the exiting air contacting the very low velocity ambient air, so the slower velocity created by diffusion reduces the velocity change and hence the noise. Thus, the branched outlet 10 diffuses the vent flow to produce lower velocity flow than that of the large outlet 2 of FIG. 1-1 which may produce less noise. Also, the diffused vent flow produces less noise with an obstruction, e.g., vent flow against bed sheet, pillow, etc.

Each of the vent arrangements described below may include one or more of the following properties: high level of diffusion to prevent vent jetting and to reduce the sensitivity of vent noise to obstructions, quietness, maintain vent flow under humidified conditions, maintain vent flow under saturated conditions, avoid vent blockage from grease and debris, minimize $CO_2$ rebreathing, physical size to fit the smallest masks, low cost, manufacturability, no particulates, robustness, cleanable and disposable, usability, durability and lifespan, compliance with existing flow generators, maintainability, biocompatibility, resist bacterial growth, quality of noise, and/or perception of reliability.

2.1 Semi-Remote Venting

FIG. 2-1 illustrates a mask including a vent arrangement according to an example of the present invention. In the illustrated example, the mask 20 includes an air delivery tube 22 having a mask end provided to the mask and a supply end provided to a flow generator adapted to deliver breathable gas to the mask. A short outer tube or shroud 25 covers a portion of the air delivery tube 22, e.g., from the mask end.

An interior surface of the outer tube 25 and an exterior surface of the air delivery tube 22 form a gap there between that defines a vent passage 26. The vent passage 26 includes an inlet 26(1) in fluid communication with the mask interior and an outlet 26(2) opening to atmosphere.

The vent passage 26 includes an annular cross-section, and the outlet 26(2) of the vent passage 26 is remote from the mask 20 and faces away from the mask and the patient. In an embodiment, the vent passage 26 may taper from the inlet to the outlet, e.g., to reduce noise.

Also, in an embodiment, the outer tube 25 may be perforated to include one or more small, diffused vent orifices 28 for gas washout.

2.2 Venting Along Inlet Conduits

FIGS. 2-2-1 and 2-2-2 illustrate a mask 220 including an interfacing structure 230 and two tubes or inlet conduits 232 extending along respective sides of the patient's face and adapted to deliver breathable gas to the interfacing structure 230. Exemplary embodiments of such a mask are disclosed in U.S. patent application Ser. No. 11/878,933, filed Jul. 27, 2007, and Ser. No. 11/878,932, filed Jul. 27, 2007, each of which is incorporated herein by reference in its entirety.

According to an embodiment of the present invention, each of the inlet conduits 232 may include one or more vent orifices 228 for gas washout. For example, the orifices 228 may be provided in a region adjacent the interfacing structure 230 (see FIG. 2-2-1) and/or the orifices 228 may be provided along the length of each conduit 232 (see FIG. 2-2-2). The orifices 228 may be arranged in any suitable pattern on the conduit (e.g., random, aligned in columns, etc.) and may be arranged to direct washout gas in any suitable direction. In addition, each conduit may have any suitable number of orifices, and each orifice may have any suitable cross-sectional configuration along its length (e.g., tapered).

2.3 Venting at the Top of the Head

In another example, a vent arrangement for a mask may be provided at the top of the patient's head in order to redirect vent exhaust away from the patient and bed partner. For example, in the mask described above in FIGS. 2-2-1 and 2-2-2, the inlet conduits extend to the top of the patient's head and are coupled to one another via a manifold. According to an embodiment of the present invention, each of the inlet conduits 232 may include one or more vent orifices 228 for gas washout in a region adjacent the manifold 235 (see FIG. 2-3-1) and/or one or more vent orifices 228 may be provided in the manifold 235 itself (see FIG. 2-3-2).

The orifices 228 may be arranged in any suitable pattern on the conduit (e.g., random, aligned in columns, etc.) and may be arranged to direct washout gas in any suitable direction. In addition, each conduit may have any suitable number of orifices, and each orifice may have any suitable cross-sectional configuration along its length (e.g., tapered).

2.4 Completely Vented Frame

Figures 1, 2:
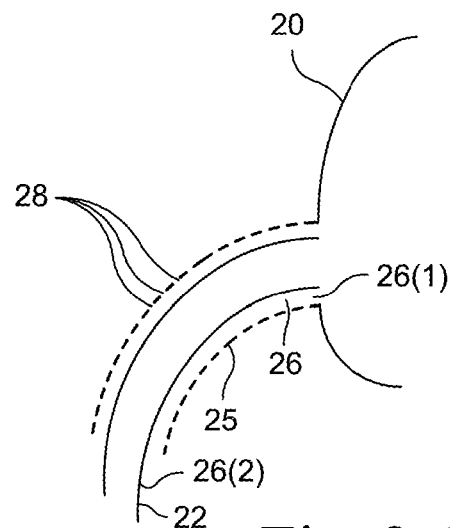
Figures 1, 2:
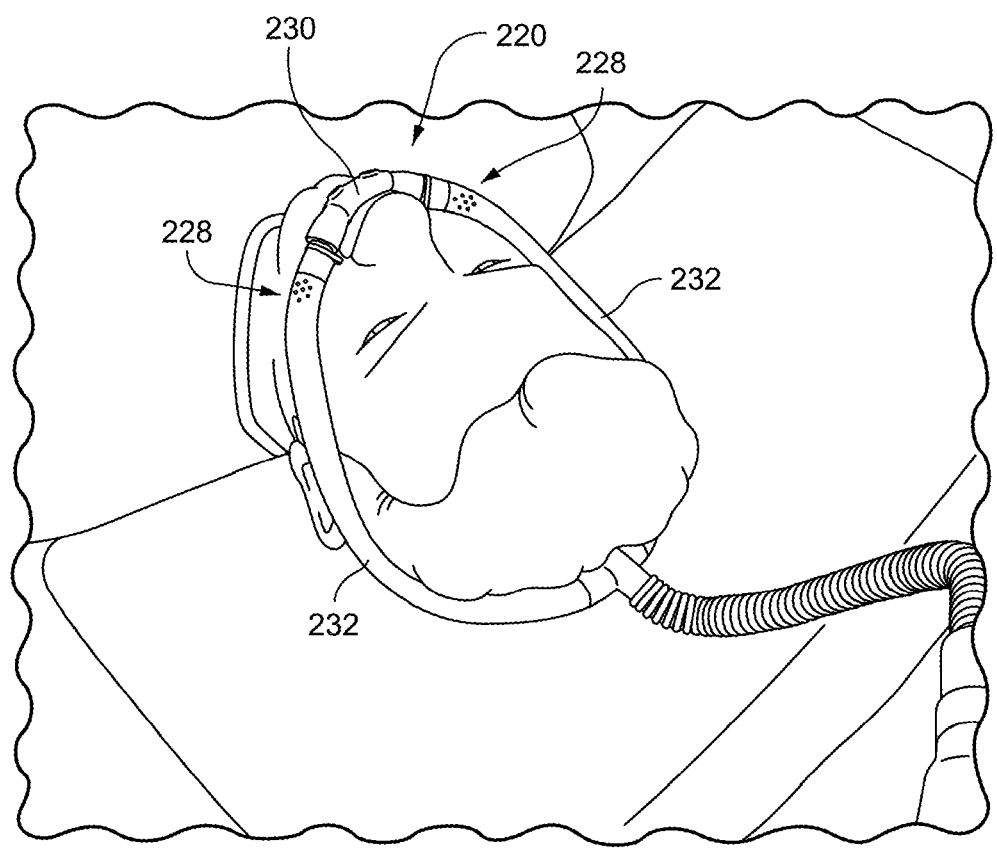
Figure 2:
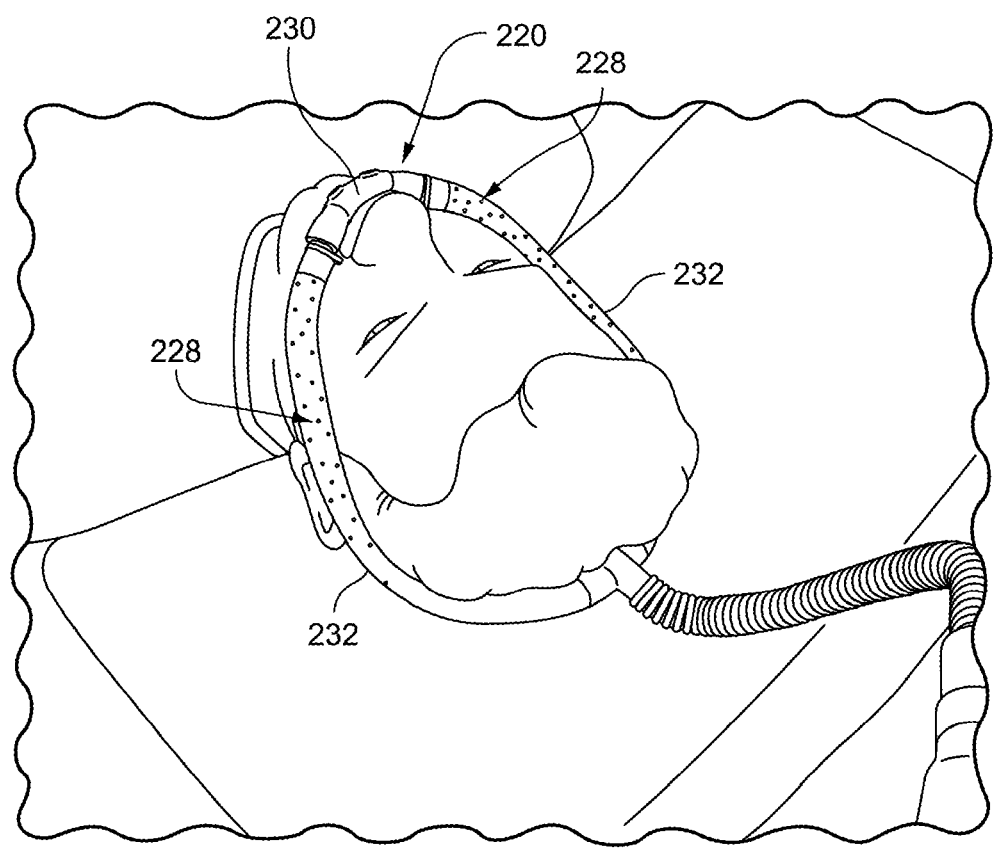
Figures 1, 2, 3:
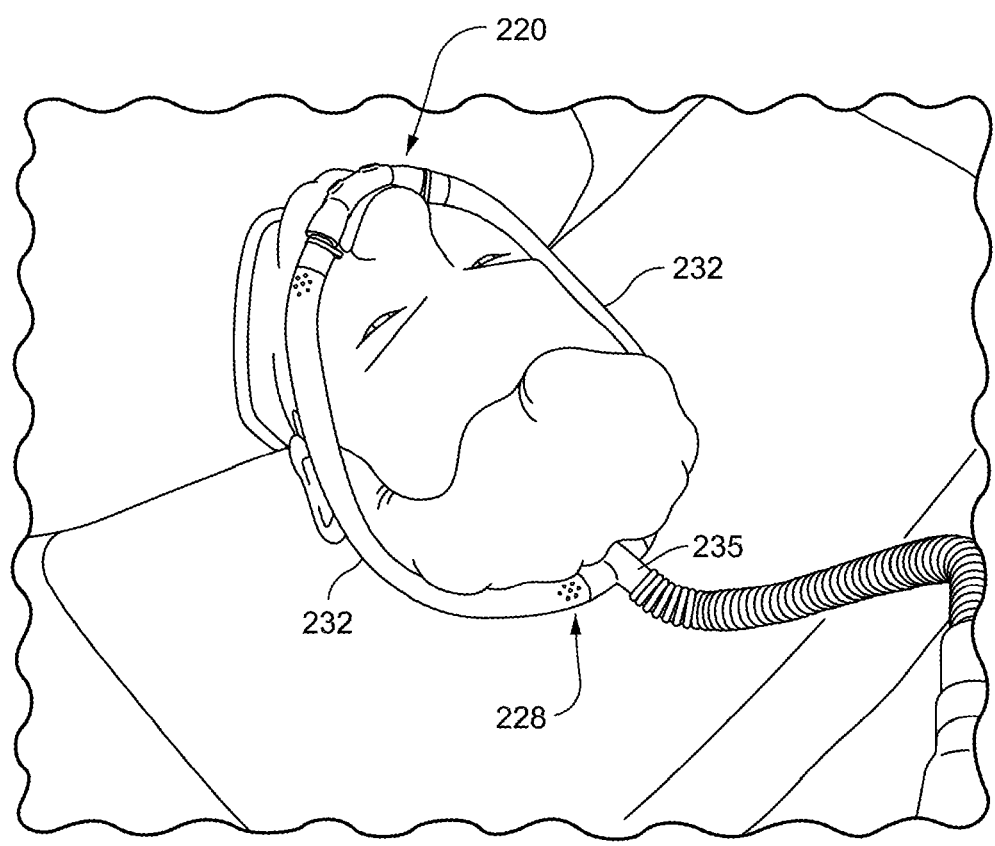
Figures 2, 3:
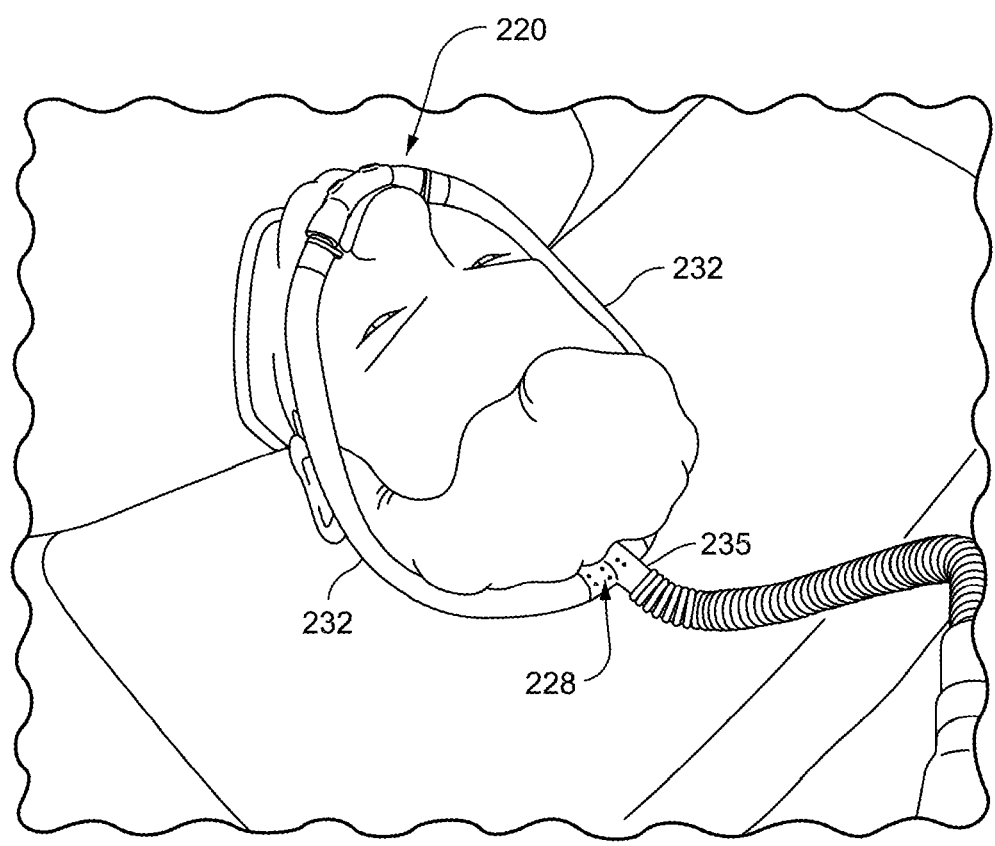
Figures 2, 3, 4:
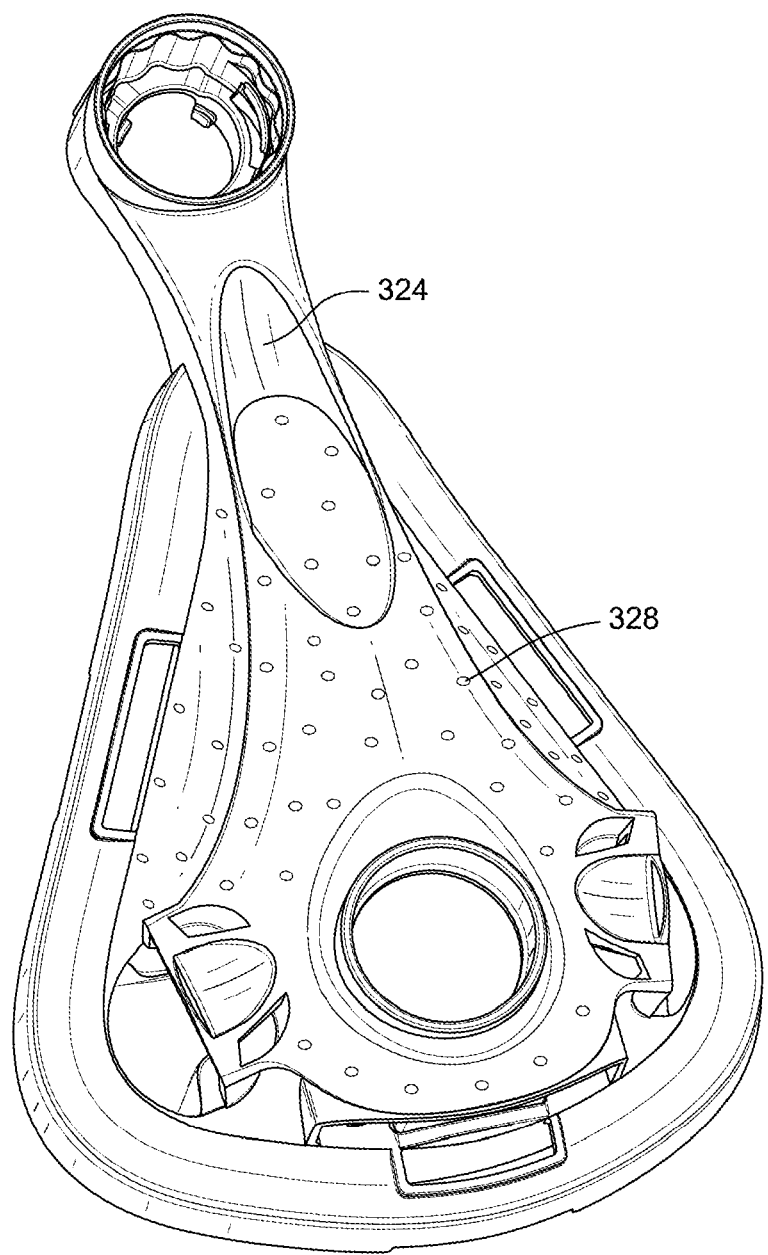

In another embodiment, a shown in FIG. 2-4, the mask frame 324 for a mask may include multiple vent orifices or clusters of vent orifices 328 spread out all over the frame 324 to diffuse gas washout. The vent orifices may be clustered in selected regions of the frame and/or the vent orifices may be distributed over the frame. In addition, the frame may have any suitable number of orifices, and each orifice may have any suitable cross-sectional configuration along its length (e.g., tapered).

2.5 Protrusions Adjacent Vent Exits

In another embodiment as shown in FIG. 2-5, the mask may include multiple, adjacent vent orifices 428, and pyramidal or conical shaped protrusions 440 may be provided adjacent the vent exits to fill in viscous shearing regions and therefore reduce noise.

It is the viscous shearing region just outside the vent exits of multiple clusters of orifices that generates vent noise, i.e., the pyramidal/conical region in between adjacent vent orifices. According to an embodiment of the present invention, protrusions 440 are provided to fill in these voids to reduce this shearing region and therefore reduce noise generated.

2.6 Hourglass-Shaped Orifice

In another embodiment, as shown in FIG. 2-6, the mask may include multiple, closely spaced vent orifices 528 with each vent orifice 528 having an hourglass shape, i.e., vent orifice 528 including the combination of a convergent orifice and a divergent orifice. Specifically, each vent orifice 528 includes an inlet portion 528(1) with a convergent configuration (i.e., orifice tapers from larger to smaller cross-section) and an outlet portion 528(2) with a divergent configuration (i.e., orifice tapers from smaller to larger cross-section). The inlet portion 528(1) to the orifice may be rounded off or include a radius to minimize entrance effects. Hourglass-shaped orifices enable longer holes to be molded as the convergent inlets and divergent outlets are formed from tooling (pins) on opposite sides that meet at the "neck". Longer holes provide a longer flow path which helps to fully develop the flow.

2.7 Reduce High Velocities Entering the Vent Inlet

In another embodiment, an obstruction may be provided in front of the inlet to the vent orifice to significantly reduce the vent inlet velocity and therefore reduce vent noise.

For example, FIG. 2-7-1 illustrates ResMed's Mirage mask 620 including a mask frame 624, an insert 627 including a plurality of vent orifices 628 provided to the frame, and an inlet tube 622 provided to frame and adapted to deliver pressurized gas. In such embodiment, the direct flow of air into the vent inlets of the orifices 628 produces high velocity, laminar flow which can generate relatively high vent noise.

According to an embodiment of the present invention, as shown in FIG. 2-7-2, an obstruction 638 (e.g., side wall extending from frame) may be placed in front of the vent inlets of the orifices 628 to create resistance and reduce flow velocity and generated vent noise. That is, the obstruction 638 reduces high velocity gas from directly entering the orifices 628, which reduces noise.

This arrangement is counter-intuitive as it challenges the notion that everything within the mask chamber should remain as undisturbed and laminar as possible, which results in high velocity flow into the vents. Any obstructions should still be "smoothly contoured" to avoid excessive noise from turbulence. Obstructions create a more tortuous, labyrinth-like path for the exhaust gases to flow through. The increased resistance of these paths reduce the kinetic energy, and therefore velocity of the flow. The reduced velocity results in reduced noise and less air jetting. Reduced velocity, fully developed laminar flow is most desirable.

2.8 Reduce Exit Vent Flow Velocity

The sound power of the vents is very sensitive to exit vent flow velocity. For example, $$W \propto \frac{S\rho V^4}{c} \text{ or } W \propto \frac{S\rho V^8}{c^5}$$

(depending on monopole or quadrupole source, respectively) where: W=radiated sound power; S=cross-sectional area of the vent; $\rho$=density of air; V=vent exit flow velocity; and c=speed of sound.

According to embodiments of the invention, the exit vent flow velocity may be reduced in order to reduce noise.

2.9 Stainless Steel Mesh

In another embodiment, as shown in FIG. 2-8, a portion of the mask may be provided with a stainless steel mesh 742 that includes plurality of vent orifices 728 for gas washout. In an embodiment, the stainless steel mesh 742 includes wires 743 that are woven with one another to create the mesh structure with the plurality of vent orifices 728. The venting or permeability provided by the mesh 742 may depend on the wire size and the tightness of the weave, e.g., orifice area may be around 25% of the total area of the mesh and the minimum orifice size may be dictated by the minimum stainless steel wire diameter as the wires weave in and out of one another. In alternative embodiments, the mesh may be constructed from other woven fabrics or meshed media, e.g., polypropylene, polycarbonate, polyamide (e.g., nylon), polyesters, polytetrafluoroethylene (e.g., Teflon), 3-dimensional spacer fabrics.

2.10 Alarm to Signal Vent Replacement/Washing

Vent arrangements including fine meshing, textiles, fragile construction of materials, and/or very small orifices are potentially prone to blockage from dirt and bio-build-up or damage. Therefore, the user either needs to regularly wash the vents or replace them to ensure that adequate vent flow is maintained for good $CO_2$ washout.

According to an embodiment of the present invention, the positive airway pressure device (PAP) device or flow generator may include an alarm to signal the user in the event of reduced vent flow so that the user knows when to replace/wash the vent arrangement. Fail-safe modes are also ways to ensure that the user is cautioned to replace/wash their vents. For instance, if the vent media were assembled to the mask with an adhesive, the adhesive could be $CO_2$-sensitive/$H_2O$-sensitive which would gradually dissolve with a pre-determined exposure to exhaled $CO_2$/humidity. Eventually, the vent media may become loose and may expose a gap (between the vent media and mask) which would still allow for the exhaustion of exhaled gases, however, it may be quite noisy. Another fail-safe mode that is somewhat similar is to ensure that the vent component has a preloaded assembly feature that gradually relaxes (i.e., creeps) with time resulting in a loosely fitting vent that would expose a gap between the vent component and the mask interface to which it is assembled.

2.11 Hydrophobic Coating

In another embodiment, a hydrophobic coating may be provided on the inside of the vent material, i.e., hydrophobic coating along the vent inlets. The hydrophobicity of the vent inlets will help to prevent the vent orifices from being blocked by humidity.

2.12 Cluster of Fine Vent Orifices Distributed Over a Dome

As shown in FIGS. 2-9-1 and 2-9-2, the mask may include a dome-shaped portion 845 and a cluster of fine vent orifices 828 distributed over the dome-shaped portion 845 for gas washout. In the illustrated embodiment, the orifice arrangement includes a central orifice and a plurality of orifices arranged in a circle about the central orifice. As illustrated, the orifices 828 are separated from one another by a distance x and each orifice 828 has a diameter size d. However, other suitable orifice arrangements are possible. For example, the orifices may be distributed over the dome in other manners, e.g., random, linearly, other patterns, etc.

In an embodiment, Computational Fluid Dynamics (CFD) may be used to model variation in orifice size and orifice separation to achieve an optimum balance of these two parameters in an attempt to mimic the diffusive properties of membranes such as Gore-Tex™.

In terms of manufacturability, the orifices may be molded out of a sheet of silicone rubber or elastomer and the sheet may be subsequently stretched over a support structure or railing (provided to the mask) structured to curve the sheet into a dome shape. However, the vent arrangement may be constructed in other suitable manners.

2.13 Adjacent Vent Orifices of Different Size and Length

In another embodiment, the mask may include multiple vent orifices with adjacent vent orifices having a different size, e.g., alternating smaller and larger vent orifices. Such arrangement may reduce noise in use.

The amount of generated vent noise is very sensitive to the difference in velocity between the exit vent flow and the velocity of the air surrounding the exit vent stream (i.e., typically the ambient air, which is relatively still).

By having variation in the size and length of adjacent vent orifices, differences in adjacent exit vent velocities are created since jet stream velocity is dependent on orifice size and flow path length. This can effectively reduce the velocity gradient between the exhaust streams and the still ambient air.

2.14 Different Levels of Velocity Shrouds

In another embodiment, the vent arrangement may include a cluster of vent orifices distributed over a portion of the frame for gas washout. In FIGS. 2-10-1 and 2-10-2, the vent orifices 928 are arranged within a circular area having a diameter d, and the orifices 928 have different sizes.

In the illustrated embodiment, the cluster includes a central or inner orifice 928(1) having a first diameter d1, a plurality of middle orifices 928(2) (e.g., six orifices) regularly spaced and separated from one another along a circle about the inner orifice 928(1) and each having a second diameter d2 that is larger than diameter d1, and a plurality of outer orifices 928(3) (e.g., eight orifices) regularly spaced and separated from one another along a circle that is concentric with the middle orifices 928(2) and each having a third diameter d3 that is larger than diameter d2.

Similar to the concept described above in section 2.13, the vent arrangement includes adjacent orifices of different size to reduce noise. Specifically, as shown in FIG. 2-10-2, the vent arrangement gradually creates different levels of velocity shrouds going from inside to outside a cluster of vent orifices. As illustrated, the velocity shroud is highest on the inner orifice 928(1) and lowest on the outer orifices 928(3) to help reduce the velocity gradient between the highest velocity, central stream and the slow moving ambient air. However, it should be appreciated that the number of orifices, size, length, spacing, and/or general layout may include a range of different permutations, e.g., non-circular arrangement of orifices.

2.15 Coated, Stainless Steel Mesh

As noted above with respect to FIG. 2-8, a portion of the mask may be provided with a stainless steel mesh that includes plurality of vent orifices for gas washout. In an embodiment, the stainless steel mesh may be heavily coated with a hydrophobic material. If the hydrophobic coating is sufficiently thick, the coating can help to block up the typically large orifice size defined in stainless steel woven meshes such as the mesh 742 described above.

2.16 Hydrophobic Meshes

In an embodiment, a hydrophobic mesh/fabric such as that described above may be a medical grade filtration mesh with an extremely consistent, fine, orifice size, e.g., mesh and fabric available from Sefar.

2.17 Slot-Orifice Vent

In another embodiment, as shown in FIG. 2-11, the mask may include a vent orifice 1028 and a cap 1050 that covers the vent orifice 1028 to define a small gap or vent passage 1026 that directs gas washout to an outlet remote from the mask, e.g., similar to the slot-orifice vent in ResMed's UltraMirage mask. The cap 1050 may include an arcuate portion 1051 adjacent the vent outlet.

The thin slot or vent passage 1026 provides for much greater effective area to encourage a long flow path to fully develop flow, thereby reducing the amount of generated vent noise. The effective venting area is just the area of the small orifice at 1028. However, the relatively large vent cap radius, half d1, provides for a long flow path.

2.18 Balance of Cleanability and Quietness of Orifice Size

In another embodiment, the orifice size may be selected so that it is both cleanable and quiet. In an exemplary embodiment as shown in FIG. 2-12, for a mask having a frame thickness of about 1.7 mm, the diameter range between d1 and d2 of the orifice may be between about 0.4-0.8 mm. As illustrated, a larger diameter orifice is easier to clean, however the larger the orifice the nosier the orifice. Such orifice size may vary, e.g., depending on frame thickness, desired cleanability and/or quietness, etc.

2.19 Fold-A-Vent

In another embodiment, the mask vent may be in the form of an insert that is provided to a mask (e.g., snap-fit into position) and defines a plurality of vent orifices. In an embodiment, as shown in FIGS. 2-13-1 to 2-13-3, the insert 1160 is constructed of a molded/stamped sheet of plastic (e.g., polypropylene with thickness in the range of about 0.5-0.8 mm) having a plurality (e.g., FIG. 2-5 or 3) of perforated sections 1162(1), 1162(2), 1162(3) that are folded against each other to produce a three-dimensional matrix of finer, porous vent orifices.

As illustrated, the first section 1162(1) includes a series of slots 1163(1) arranged at a first angle, the second section 1162(2) includes a series of slots 1163(2) arranged at a second angle, and the third section 1162(3) includes a series of slots 1163(3) arranged at a third angle. In the illustrated embodiment, the first angle is about 135° from horizontal, the second angle is about 45° from horizontal (i.e., perpendicular to the first angle), and the third angle is vertical or about 90° from horizontal. However, the slots may be arranged at other varying angles. Also, each of the slots has a similar width. However, the slots may have varying widths, which may vary from slots in other sections.

The sections 1162(1), 1162(2), 1162(3) are joined to one another by integral hinges 1164 (e.g., reduced width, slotted edges between sections) to facilitate folding. Also, ends of the first and third sections 1162(1), 1162(3) may includes locking snaps or tabs 1165 structured to retain the insert in its folded configuration.

When in its folded configuration, the slots 1163(1), 1163(2), 1163(3) overlap one another to provide fine, porous vent orifices through the insert 1160. The insert 1160 may be unfolded or opened for cleaning and/or quick drying.

2.20 Stack-A-Vent

FIGS. 2-14-1 to 2-14-3 illustrate another embodiment of a vent insert 1260 for a mask. In this embodiment, the vent insert 1260 includes a plurality of grill components 1270(1), 1270(2), 1270(3), 1270(4) (also referred to as cover members) that are stacked on top of one another to produce a three-dimensional matrix of finer, porous vent orifices.

As illustrated, the vent insert 1260 includes a cylindrical base 1265 that provides a flange or shoulder 1266 adapted to support the base within an outlet opening in the mask. A grill 1268 (e.g., one or more cross-bars) defining a series of slots or outlet openings 1263 is provided to an upper portion of the base 1265.

Also, the upper portion of the base 1265 includes an annular rim 1267 adapted to support a plurality of disk-like grill components 1270(1), 1270(2), 1270(3), 1270(4). In the illustrated embodiment, four grill components 1270(1), 1270(2), 1270(3), 1270(4) are provided to the base 1265. However, more or less grill components may be used, e.g., 1, 2, 3, 4, or more grill components.

Each disk-like grill component 1270(1), 1270(2), 1270(3), 1270(4) includes a grill 1272 defining a series of slots and an annular rim 1274 adapted to interlock with the base 1265 and/or other grill components. Specifically, the upper edge of the annular rim includes diametrically opposed protrusions 1276 and the lower/outer edge of the annular rim includes a series of recesses 1278 (e.g., twelve recesses) regularly spaced and separated from one another.

In use, a first grill component 1270(1) is coupled to the base 1265 by interlocking selected recesses 1278 with the diametrically opposed protrusions 1269 provided on the annular rim 1267 of the base 1265. The first grill component 1270(1) may be selectively rotated and interlocked with the base 1265 in order to adjust the angle of its grill 1272 with respect to the grill 1268 of the base 1265.

Then, the second grill component 1270(2) may be selectively coupled to the first grill component 1270(1) by interlocking selected recesses 1278 with the diametrically opposed protrusions 1276 provided on the first grill component 1270(1). Similarly, the third grill component 1270(3) may be selectively coupled to the second grill component 1270(2), and the forth grill component 1270(4) may be selectively coupled to the third grill component 1270(3). In each coupling, the grill components 1270(1), 1270(2), 1270(3), 1270(4) may be selectively rotated and interlocked in order to adjust the angle of the grills 1272 with respect to one another. That is, the grill components 1270(1), 1270(2), 1270(3), 1270(4) may be stacked in different configurations to create different arrays of vent orifices through the insert.

In use, as shown in FIG. 2-14-3, the grill 1268 of the base 1265 and the grills 1272 of the grill components 1270(1), 1270(2), 1270(3), 1270(4) overlap one another to provide fine, porous vent orifices through the insert 1260. Each of the grill components or cover members 1270(1), 1270(2), 1270(3), 1270(4) includes a surface 1279 that extends over an outlet of at least one outlet opening 1263. The insert 1260 may be uncoupled or unstacked for cleaning and/or quick drying.

2.21 Single and Double Layer Media

FIGS. 2-15-1 to 2-15-3 illustrate another embodiment of a vent insert 1360 for a mask. In this embodiment, the vent insert 1360 includes media 1380 (e.g., (anti-bacterial) filter, membrane, fabric, mesh, or other porous material) to diffuse flow.

As illustrated, the vent insert 1360 includes a cylindrical base 1365 that provides a flange or shoulder 1366 adapted to support the base within an outlet opening in the mask (e.g., base secured to mask by friction-fit, adhesive, etc.). A grill 1368 (e.g., one or more cross-bars) defining a series of slots is provided to a lower portion of the base 1365. The grill or cross-bar(s) 1368 prevents inadvertent touching of the vent media during mask handling, and thereby minimizes the contamination of the vent media through handling.

The upper portion of the base 1365 includes an annular rim 1367 adapted to support at least one or more media 1380, e.g., one or more layers, e.g., two layers. Also, a plurality of snap-fit tabs 1375 (e.g., four snap-fit tabs) extend upwardly from the rim. The tabs 1375 are adapted to interlock with a cover 1385 structured to maintain the media 1380 within the base 1365.

The cover 1385 includes an annular side wall 1386 and a cross-bar 1387. An edge of the side wall includes an engagement flange 1386(1) adapted to engage within a recess 1375(1) provided in each of the tabs 1375 with a snap-fit. The cross-bar 1387 prevents inadvertent touching of the vent media during handling of the mask to minimize contamination of the vent media (e.g., from body oils, hand moisturizers, etc.).

In use, at least one media 1380 is selected (e.g., (anti-bacterial) filter, membrane, fabric, mesh, or other porous material) and inserted within the base 1365, and the cover 1385 is snap-fit to the base 1365 to retain the media 1380 therein. As shown in FIG. 2-15-3, the vent flow is diffused as it passes through the grill 1368 and media 1380 of the insert 1360, which reduces noise. The cover 1385 may be removed to clean and/or replace the media 1380.

In an embodiment, the base 1365 and cover 1385 may be molded of a plastic material to define a plastic casing for the at least one media 1380. The at least one media 1380 may be overmolded or adhered to the casing. In such arrangement, the entire vent insert 1360 may be replaced (i.e., replaceable cartridge), rather than replace the individual media.

2.22 Double Layer Media with Expansion Chamber

FIGS. 2-16-1 to 2-16-3 illustrate another embodiment of a vent insert 1460 for a mask. In this embodiment, the vent insert 1460 includes two layers of media 1480(1), 1480(2) (e.g., (anti-bacterial) filter, membrane, fabric, mesh, or other porous material) to diffuse flow.

As illustrated, the vent insert 1460 includes a cylindrical base 1465 that provides a flange or shoulder 1466 adapted to support the base within an outlet opening in the mask. A grill 1468 defining a series of slots is provided to a lower portion of the base 1465. The grill 1468 prevents inadvertent touching of the vent media during mask handling, and thereby minimizes the contamination of the vent media through handling.

The upper portion of the base 1465 includes a lower annular rim 1467(1) adapted to support a first media 1480(1) and an upper annular rim 1467(2) adapted to support a second media 1480(2). Also, an engagement flange 1475 extends upwardly from the upper rim and is adapted to engage a cover 1485 structured to maintain the first and second media 1480(1), 1480(2) within the base 1465.

The cover 1485 includes a ring portion 1486 and a cross-bar 1487. An edge of the ring portion 1486 is adapted to engage the flange 1475 provided to the base 1465. The cross-bar 1487 prevents inadvertent touching of the vent media during handling of the mask to minimize contamination of the vent media (e.g., from body oils, hand moisturizers, etc.).

Further, the perimeter of the base 1465 includes a recessed side wall and a series of slots 1482 extending through the side wall. A cylindrical band 1483 (e.g., filter or other suitable permeable media) is provided to the recessed side wall and covers the slots 1482.

In use, a first media 1480(1) is selected (e.g., (anti-bacterial) filter, membrane, fabric, mesh, or other porous material) and inserted into the lower rim 1467(1) of the base 1465, a second media 1480(2) is selected (e.g., (anti-bacterial) filter, membrane, fabric, mesh, or other porous material) and inserted into the upper rim 1467(2) of the base 1465, and the cover 1485 is engaged with the base 1465 to retain the media 1480(1), 1480(2) therein. As illustrated, the cover 1485 includes an annular protrusion 1469 adapted to engage an upper surface of the second media 1480(2) to secure the same in position. It should be appreciated that the first and second media may include similar structures (e.g., material, thickness, etc.), or the first and second media may include structures that are different from one another. Also, the first and second media may include different diameters (as illustrated) or the first and second media may include similar diameters (with the base structured to support the same).

As shown in FIG. 2-16-3, the vent flow is diffused as it passes through the grill 1468 and first and second media 1480(1), 1480(2) of the insert 1460, which reduces noise. In addition, the vent flow may pass through the slots 1482 and band 1483 between the first and second media 1480(1), 1480(2) to diffuse the flow. The cover 1485 may be removed to clean and/or replace the first and second media 1480(1), 1480(2). Utilizing an arrangement of double layer vent media compared with a single layer of vent media allows the use of more permeable, open-structured weaves. The larger orifices of these more open-weaves are less likely to occlude with debris, humidity and saturation. More open-weaves are also easier to clean.

2.23 Pleated Media

FIGS. 2-17-1 to 2-17-3 illustrate another embodiment of a vent insert 1560 for a mask. In this embodiment, the vent insert 1560 includes pleated media 1580 (e.g., (anti-bacterial) filter, membrane, fabric, mesh, or other porous material) to diffuse flow.

As illustrated, the vent insert 1560 includes a cylindrical base 1565 that provides a flange or shoulder 1566 adapted to support the base within an outlet opening in the mask. A grill 1568 defining a series of slots is provided to a lower portion of the base 1565. The grill 1568 prevents inadvertent touching of the vent media during mask handling, and thereby minimizes the contamination of the vent media through handling.

The upper portion of the base 1565 includes an annular rim 1567 adapted to support media 1580 having a plurality of pleats or folds. Also, an engagement flange 1575 extends upwardly from the rim and is adapted to engage a cover 1585 structured to maintain the media 1580 within the base 1565.

The cover 1585 includes a ring portion 1586 and a cross-bar 1587. The cross-bar 1587 prevents inadvertent touching of the vent media during handling of the mask to minimize contamination of the vent media (e.g., from body oils, hand moisturizers, etc.). The edge of the ring portion 1586 includes a recess and adapted to engage the flange 1575 provided to the base 1565.

In use, a pleated media 1580 is selected (e.g., (antibacterial) filter, membrane, fabric, mesh, or other porous material) and inserted within the base 1565, and the cover 1585 is engaged with the base 1565 to retain the media 1580 therein.

As shown in FIG. 2-17-3, the vent flow is diffused as it passes through the grill 1568 and the pleated media 1580 of the insert 1560, which reduces noise. The cover 1585 may be removed to clean and/or replace the pleated media 1580. The use of pleated media allows for a greater area of lower air permeability, venting media to be used whilst still maintaining the footprint within a relatively small area. The lower the air permeability of the venting media, the more effective it is at reducing noise and diffusing air flow as it is much more restrictive to flow.

2.24 Media to Diffuse Flow

In embodiments described above, media (e.g., (anti-bacterial) filter, membrane, fabric, mesh, or other porous material) may be provided to the vent arrangement (e.g., vent insert) to diffuse flow. Media may be selected from a range of materials, properties, and manufacturers.

For example, exemplary media may be disposable and/or hydrophobically treated and may be in the form of a plastic mesh, stainless steel mesh, 3D spacer fabric, felt, and/or membranes (e.g., PALL, Gore-Tex, GE Energy). Specific examples include PALL BB Filter (hydrophobic), GE Energy ePTFE membrane, Gore-Tex ePTFE membrane, Sefar PP mesh 05-1001-K120, Sefar PP mesh 05-1001-1 (079, Sefar PP mesh 05-8000-K085, 3D spacer fabric SPC-121, Sefar SS mesh 165/1400, Sefar PET mesh 07-88-1(080 double layer, Sefar PET mesh 07-88-K080 double-layer-gap, Sefar PET mesh 07-88-1(060 double layer, Sefar NFW-PEPE-384-CS17, Transpor Drylayer woven wicking fabric, reticulated foam, and/or 3M 8710E non-woven.

Advantages of the plastic mesh include: hydrophobic treatment, small footprint, humidification, biocompatible, and/or simple automated punching and overmolding. Advantages of the stainless steel mesh include high perceived value, robustness, and/or biocompatible. Advantages of the 3D spacer fabric include small footprint and/or humidification. Advantages of the felt include semi-hydrophobic, control of permeability with density, and/or less expensive. Advantages of the membranes include pleating, cost, hydrophobic. "high tech", and/or biocompatible.

In an embodiment, the media may be constructed of an electrically conductive material that allows a current to pass through the media, e.g., to dry the media during and/or after use and prevent water vapor from clogging the vent openings.

2.25 Common Component

As noted above, the vent arrangement may be a common component structured for use in multiple interface types. For example, FIGS. 2-18-1 to 2-18-3 illustrate the vent insert 1360 shown in FIGS. 2-15-1 to 2-15-3 provided to three different types of interfaces. In FIG. 2-18-1, the vent insert 1360 is attached to the mask frame 1624 of a mask. In FIG. 2-18-2, the vent insert 1360 is attached to the mask elbow 1627 of a mask. In FIG. 2-18-3, the vent insert 1360 is attached to the end of a frame 1629 for a nasal prong arrangement. The interchangeability of the vent insert 1360 facilitates manufacturing and replacement.

2.26 Annular Vent

As noted above in FIG. 1-1, vent flow for a single large outlet with a relatively short flow path produces relatively high velocity flow. Such high velocity flow is considered a "jet stream", generating large changes in speed directly outside the outlet. Such arrangement generates high jet noise.

Since the noise level is determined by the speed of the jet stream in relation to the speed of the surrounding air, noise production can be greatly reduced by using an extra air stream with a lower speed outside the jet stream as shown in FIG. 2-19 (i.e., central higher-velocity stream and outer lower-velocity streams. As illustrated, the graduated change in speed across the streams is less than that of a single stream to ambient air. FIG. 2-19 is a schematic of the velocity shrouds described above with respect to FIG. 2-10-2 for example.

FIG. 2-20 illustrates an embodiment of a dual flow mouthpiece 1790 for an air compressor. This embodiment is an example illustrating an application of the theory in FIG. 2-19 to reduce noise of the jet stream. As illustrated, the dual flow mouthpiece 1790 includes a central conduit 1792 that provides a fast inner stream and an outer annular conduit 1794 that provides a slow outer stream. Such arrangement produces less noise than a mouthpiece having a single conduit or stream.

FIGS. 2-21-1 to 2-21-4 illustrate an elbow assembly 1845 according to an embodiment of the present invention. The elbow assembly 1845 includes a vent arrangement that allows part of the vented gas to move at a slower speed outside a faster central stream to reduce noise. Such vent arrangement may be adapted for use with elbow assemblies described in U.S. Provisional Application No. 60/924,359, filed May 10, 2007, which is incorporated herein by reference in its entirety. However, it should be appreciated that such vent arrangement may be applied to other portions of a mask, e.g., mask frame.

As shown in FIGS. 2-21-1 to 2-21-4, the elbow assembly 1845 includes an elbow 1846 and a cover 1850 releasably attached to the elbow 1846. The elbow 1846 includes a first end 1846(1) for releasably engaging with an opening in a mask frame and a second end 1846(2) for releasably engaging with a swivel. Each of the first and second ends 1846(1), 1846(2) include a plurality of resilient flexible arms 1847 adapted to engage the frame/swivel with a snap-fit.

The main body of the elbow 1846 includes a venting area which includes a plurality of vent orifices 1828 for gas washout. As best shown in FIGS. 2-21-3 and 2-21-4, each vent orifice 1828 tapers from a smaller cross-section at the vent inlet to a larger cross-section at the vent outlet. A pair of lugs 1848 (only one being visible in FIG. 2-21-1) are provided on opposing sides of the venting area. The lugs 1848 are adapted to engage respective retaining members 1851 (see FIG. 2-21-2) provided on an inside surface of the cover 1850. Also, one or more tabs 1849 (see FIG. 2-21-1) are provided to the main body of the elbow 1846 to space the cover 1850 away from the outer surface of the main body. In an alternative embodiment, the taper direction of the vent orifices may be reversed, i.e., from larger cross-section at the inlet to smaller cross-section at the outlet.

As shown in FIG. 2-21-2, the elbow 1846 includes a baffle 1852 adjacent to where the elbow 1846 is attached to the mask frame. The baffle 1852 has a generally U-shape and is arranged to divide the upper arm of the elbow into an air delivery passage and an exhaust passage.

The cover 1850 includes a venting area which includes a plurality of vent clusters 1854 for gas washout. Specifically, each vent cluster 1854 includes a tubular spigot that defines an orifice 1856 that tapers from a larger cross-section at the inlet to a smaller cross-section at the outlet, and a plurality of arcuate shaped orifices 1858 (e.g., 4 orifices) regularly spaced and separated from one another along a circle about the spigot and each having a cross-section that tapers from a larger cross-section at the inlet to a smaller cross-section at the outlet. In an alternative embodiment, the taper direction of the orifices may be reversed, i.e., from smaller cross-section at the inlet to larger cross-section at the outlet.

In the connected position, the venting area of the cover 1850 is aligned with the venting area of the elbow 1846 to define vent flows with a faster inner stream and a slower outer stream as shown in FIG. 2-21-3. Specifically, each vent cluster 1854 of the cover 1850 is aligned with a respective orifice 1828 of the elbow 1846 such that the spigot of each vent cluster 1854 extends partially within the respective orifice 1828 of the elbow 1846.

In use, vent flow passes through the orifices 1828 of the elbow 1846 and into respective vent clusters 1854 of the cover 1850. As shown in FIG. 2-21-3, the flow passing through the orifice 1856 of the spigot is faster than the flow passing through the orifices 1858 outside the spigot. The extra, slower outer stream can reduce vent noise in use.

Such arrangement also allows pins with a thickness of 0.7 mm or less to be used to mold very small holes, i.e., the arcuate orifices 1858 around the central orifice 1856. In known embodiments, normal molding pins having a diameter of less than 0.7 mm are not particularly robust for use in tooling for molds.

In an embodiment of the vent arrangement, as shown in FIG. 2-21-4, $D_1$ may be about 1.76 mm, $D_2$ may be about 0.7 mm, $D_3$ may be about 0.3 mm, $D_4$ may be about 1.13 mm, $D_5$ may be about 1.6 mm, $D_6$ may be about 2.6 mm, $D_7$ may be about 2.5 mm, $D_8$ may be about 1.5 mm, and $D_9$ may be about 2 mm Although specific dimensions and ranges of the vent arrangement are indicated, it is to be understood that these dimensions and ranges are merely exemplary and other dimensions and ranges are possible depending on application. For example, the exemplary dimensions may vary by 10-20% or more or less depending on application.

2.27 Protrusions with Vents

FIGS. 2-22-1 and 2-22-2 illustrate a vent arrangement 2000 according to another embodiment of the present invention. In this embodiment, the vent arrangement 2000 includes one or more protrusions 2002 provided to a venting area 2004 of the mask, and one or more vent openings 2006 are provided in side walls of each protrusion 2002 to vent washout gas. In addition, one or more vent openings 2008 may be provided in the venting area adjacent the protrusions 2002 to vent washout gas. In use, washout gas from the vent openings 2006 in the protrusions 2002 and washout gas from the vent openings 2008 in the adjacent venting area are directed into one another to diffuse the air flow, which results in more diffused venting. Alternatively, the adjacent streams may also be slightly offset to avoid direct collision of the streams to minimize turbulent noise yet still provide some degree of diffusion.

In the illustrated embodiment, the venting area 2004 provides a base wall 2005 and the plurality of protrusions 2002 extend outwardly from the base wall 2005. As illustrated, each protrusion 2002 is in the form of a truncated pyramid, and a vent opening 2006 is provided through each side wall of the pyramid, i.e., four vent openings 2006 per pyramid. However, it should be appreciated that any suitable number of openings may be provided to each pyramid, e.g., multiple openings in each side wall, opening in only selected side walls, opening in at least one side wall, etc. Also, in the illustrated embodiment, each opening 2006 has a generally trapezoidal shape, e.g., height of about 0.2-0.6 mm (e.g., 0.4 mm). However, the openings may have other suitable shapes, sizes, and/or arrangement, e.g., circular, tapered along its length, etc.

As shown in FIG. 2-22-1, the protrusions 2002 are arranged corner to corner in a spaced-apart, grid-like manner Such arrangement defines multiple venting areas between the protrusions 2002 in which respective vent openings 2008 are provided. However, other suitable arrangements of the protrusions are possible, e.g., random, circular, rows, columns, etc. In addition, it should be appreciated that more than one opening 2008 may be provided in each venting area defined between protrusions 2002. Also, openings 2008 may simply not be provided.

In the illustrated embodiment, each opening 2008 has a generally circular shape. However, the openings 2008 may have other suitable shapes, sizes, and/or arrangement, e.g., non-circular, tapered along its length, etc.

The protrusions 2002 are structured to increase the surface area available for venting so more vent openings may be provided over a venting area of the mask. For example, in the illustrated embodiment, the protrusion 2002 provides four vent openings 2006 in a similar area as each vent 2008.

In use, the vent openings 2006 in the protrusions 2002 and the vent openings 2008 in the base wall 2005 are arranged so that washout gas is directed in different directions, into one another and/or slightly offset from one another to create diffuse air flow, e.g., see FIG. 2-22-1.

It should be appreciated that the protrusions may have other suitable shapes or arrangements. For example, the protrusions may be star-shaped, crescent-shaped, alpha-numerically shaped, logo-shaped, hexagonal, octagonal, etc. That is, the protrusions may have any suitable shape with vent openings arranged to deliver exhaust gases in a direction that is not parallel to adjacent vent orifices. Also, as shown in FIGS. 2-22-3 and 2-22-4, the lower edge of the vent openings 2006 may align with the base wall 2005, rather than be spaced upwardly from the base wall 2005 as in FIGS. 2-22-1 and 2-22-2. Additionally, the inner base wall or interior surface of protrusion 2002 may be shaped rather than planar (as shown in FIGS. 2-22-2 and 2-22-4), for example angular or rounded. This arrangement may direct the air stream out of vent openings 2006 in a smoother pathway, thereby reducing turbulent flow and thus noise.

FIG. 2-22-5 is a schematic view of a mold for molding the protrusions of FIGS. 2-22-3 and 2-22-4. As illustrated, upper and lower molds UM, LM cooperate to define the top of the protrusions, the base wall, and the vent openings there between.

In another example, as shown in FIG. 2-23, each of the protrusions may have an inverted configuration, e.g., truncated pyramid-shaped recess that extends inwardly from the base wall 2005 and into the breathing cavity. In such arrangement, a vent opening 2007 may be provided in the bottom wall of each truncated pyramid-shaped recess rather than the base wall 2005 to create diffuse flow.

In another example, as shown in FIG. 2-24, each protrusion may have a dome-shape with vent openings 2006 provided along the dome.

In yet another example, as shown in FIG. 2-25, each protrusion may be in the form of an elongated three-dimensional trapezoid with vent openings 2006 along side walls thereof. As illustrated, the 3-D trapezoids may be spaced apart to define venting areas there between in which vent openings 2008 are provided.

In an embodiment, the protrusion may be provided as a separate component from the mask that is adapted to be attached or retrofit to the mask including one or more vent openings. That is, the protrusion may be secured in position (e.g., glued, snap-fit, etc.) over a selected vent opening to cover the vent opening and provide diffused vent flow as gas passes there through in use.

2.28 Disk-Like Vent Arrangement

FIG. 2-26 illustrates a vent arrangement 2100 according to another embodiment of the present invention. In this embodiment, the vent arrangement 2100 is structured to be connected between the mask and the air delivery conduit. As illustrated, the vent arrangement 2100 includes a plurality of disks 2195 adapted to be stacked on top of one another. A plurality of the disks 2195 (e.g., every disk in the stack, every other disk in the stack, etc.) include vent openings 2197 (e.g., curved recesses) that create passages for diffused vent flow. A longer length of the stacked disks may create more diffuse vent flow.

In an embodiment, the disks may be coupled to one another (e.g., slinky-like arrangement) to create a one-piece structure, e.g., to facilitate cleaning and reduce the risk of losing small parts.

3.0 Sound Power

FIG. 3 provides a chart illustrating sound power for vent media described above. As illustrated, at 10 cmH$_2$O, the sound power for vent media described above may range from about 22 dBA to about 45 dBA for a flow rate of about 6-57 L/min, and at 20 cmH$_2$O, the sound power may range from about 28-35 dBA for a flow rate of about 23-42 L/min. The standard vent can be, for example, the vent arrangement shown in FIG. 4-1A.

The vent media may be selected based on sound requirements, preferences, etc. For example, in an embodiment, the vent may be quieter than about 30 dBA. In another embodiment, the vent may be quieter than about 25 dBA. The sound power for the vent media may be dependent on the coarseness of the fibers in each vent media, the size of the holes in the vent media, and/or the flow path through the vent media.

In an embodiment, the fibers in the vent media may not be coarse so as to avoid turbulent flow. For example, ePTFE membrane may have flaws and variations throughout the membrane and therefore may cause higher noise levels particularly at higher flow rates.

In an embodiment, the size of the holes in the vent media may be small, for example, the stainless steel meshes may have small vent holes that emit an acceptable level of noise.

In an embodiment, the flow path through the vent media may be generally long and direct, forming for example a continuous tunnel. For example, the flow path through the PP mesh may be more direct (due to the arrangement of fibers) than that through the reticulated foam or woven wicking fabric thereby reducing the noise emitted from the PP mesh than the foam.

4.1 Bayonet Vent

FIG. 4-1A to 4-7D illustrate a vent arrangement according to another embodiment of the present invention. In this embodiment, the mask vent is in the form of a vent cap structured to be releasably attached to an opening or venting area of the mask. The vent cover includes a plurality of vent holes constructed and arranged to diffuse airflow leaving the mask in use.

Figures 1A, 4:
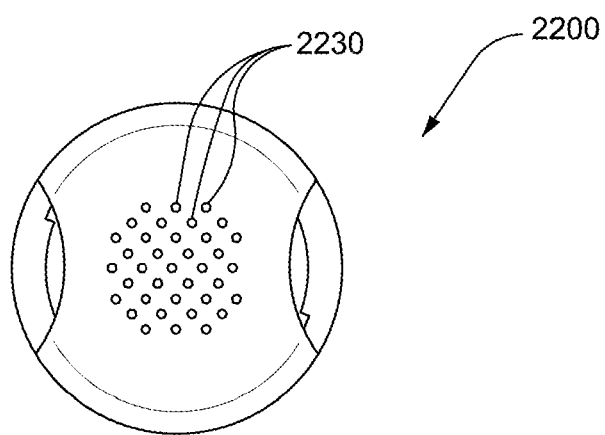
Figures 1B, 4:
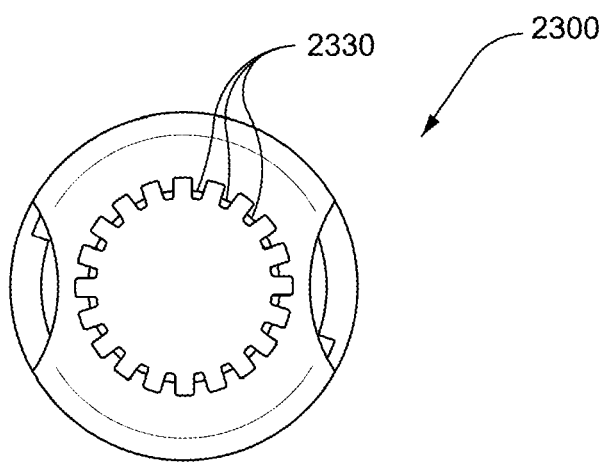
Figures 1C, 4:
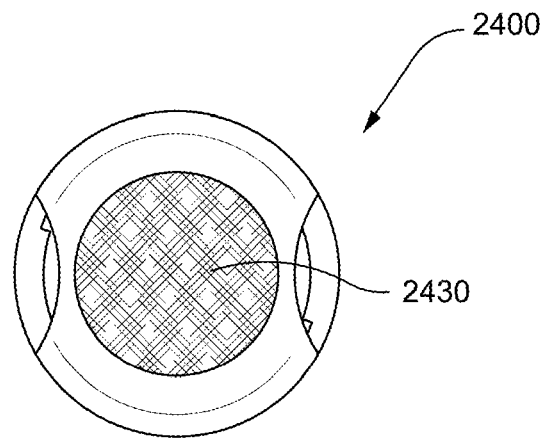
Figures 2A, 4:
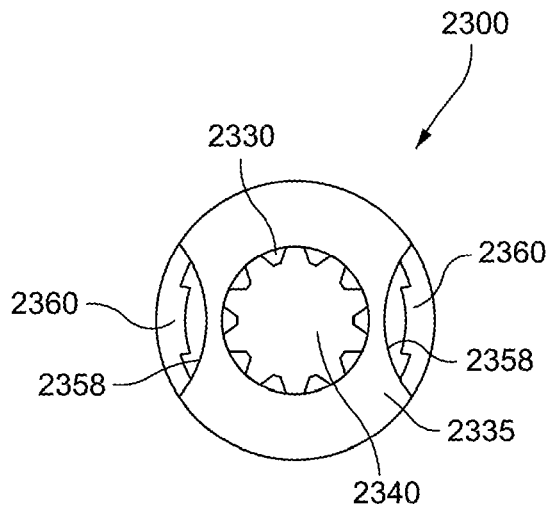

FIGS. 4-1A to 4-1C illustrate vent caps according to alternative embodiments of the present invention. FIG. 4-1A illustrates a vent cap 2200 including multiple vent holes 2230 arranged on a base wall to direct airflow away from the patient's face in use. FIG. 4-1B illustrates a vent cap 2300 including multiple vent holes 2330 arranged on an annular side wall to provide diffuse airflow that is directed away from the patient's face as well as the bed partner. The angle of the diffused airflow can be tuned by altering the dimensions of the vent cap. FIG. 4-1C illustrates a vent cap 2400 including media 2430 (e.g., textile, filter, membrane, fabric, mesh, or other porous material or means of ventilation) structured to diffuse airflow from the mask.

In each vent cap embodiment, there may be any suitable number of holes distributed around the vent cap. Each hole may have any suitable shape, e.g., generally round, square, tapered along its length, etc. Also, the holes may be uniform or varying in size and/or shape. In an embodiment, each hole may be no smaller than about 0.00-0.08 mm in diameter. Preferably, each hole may be no smaller than 0.6-0.8 mm (e.g., 0.7 mm) in diameter. Smaller holes may be preferable as they direct air flows in such a way that they become more fully developed flows. In an alternative embodiment, the vent cap may include a venting area adapted to be aligned with a venting area of the mask (e.g., elbow) when assembled together to define "full" vent passages, e.g., similar to the arrangement shown in FIGS. 2-21-1 to 2-21-4 described above.

In an embodiment, the vent cap may be made from a polymer, such as polypropylene or polycarbonate. However, other suitable materials are possible. Also, the vent cap may be constructed and arranged to be relatively durable, or the vent cap may be constructed and arranged to be less durable, replaceable, and/or disposable.

The vent cap 2300 will now be described in greater detail. As shown in FIGS. 4-2A to 4-2C and 4-3A to 4-3C, the vent cap 2300 includes a base wall 2335 and a dome 2340 that extends upwardly from the base wall 2335 above the horizontal surface of the base wall 2335. As illustrated, the multiple vent holes 2330 are arranged on an annular side wall of the dome 2340.

Figures 2B, 4:
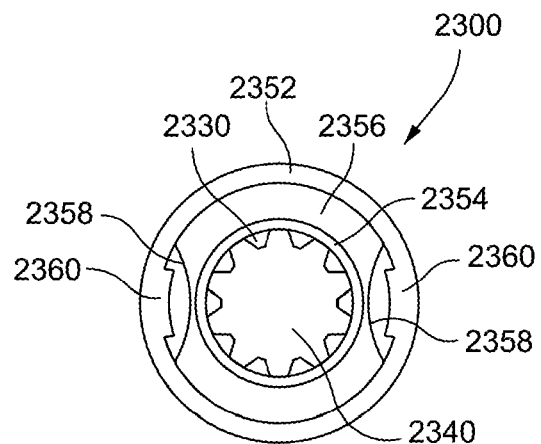
Figures 2C, 4:
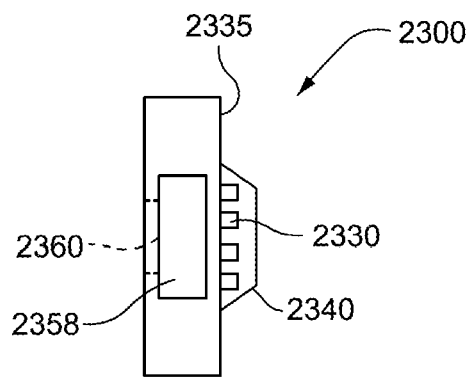
Figures 3A, 4:
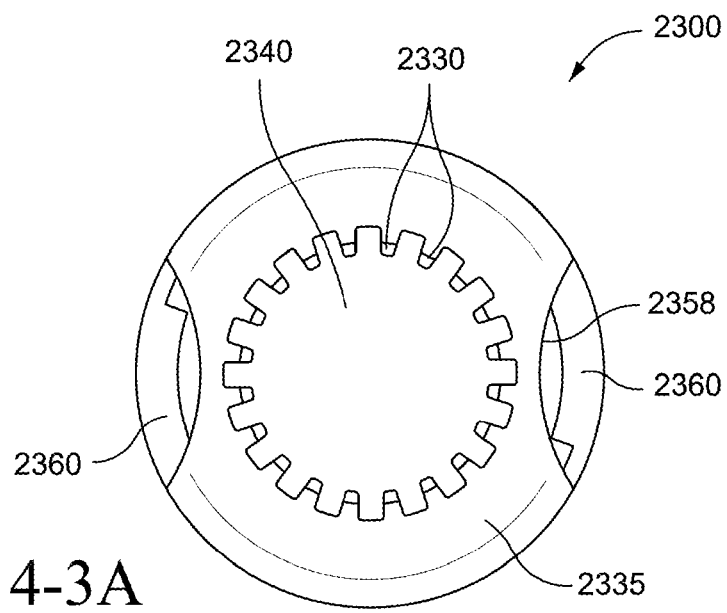
Figures 3B, 4:
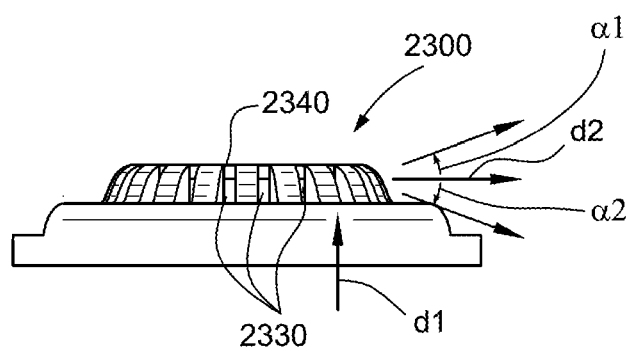
Figures 3C, 4:
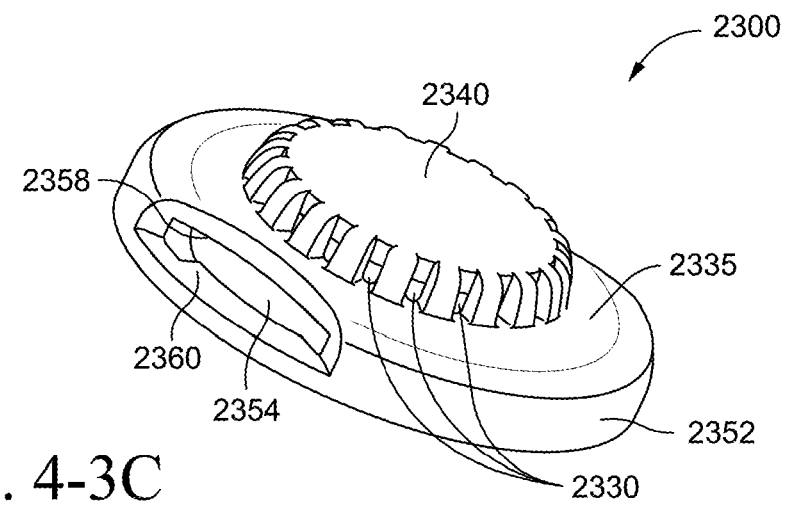

The dome 2340 may have a generally hemispherical, trapezoidal, square, or other desired shape. Preferably, the dome 2340 has a low profile, e.g., raised 1-3 mm (e.g., 2 mm) from the horizontal surface of the base wall. This arrangement helps to direct air flow in long, thin paths so as to maintain more fully developed and/or laminar flow. Also, the "domed" vent cap directs exhaust flow up and out from the mask, i.e., "domed" vent cap alternates the direction of exhaust flow from a first incoming direction d1 to a second outgoing direction d2 that is sloped or angled with respect to the first direction d1, e.g., substantially perpendicular, as shown in FIG. 4-3B. In addition, the vent cap constitutes an exhaust divider as the vent holes are arranged to divide the exhaust flow in different directions as it exits the vent cap. In the illustrated embodiment, the vent holes are arranged radially along the annular side wall of the dome 2340 to radially divide the exhaust flow in 360°. However, it should be appreciated that the vent holes may be arranged in other suitable manners along the circumference of the dome, e.g., a portion of the circumference up to 360° (e.g., 270°, 180°, 90°, or less and anywhere in between), selected arcs or portions of the circumference (e.g., selected portions on opposite sides of the dome). Alternative vent hole arrangements on the dome may be selected to direct exhaust gas in certain directions, e.g., away from the patient's face or bed partner. Also, as shown in FIG. 4-3B, the vent holes may be configured to direct exhaust gas at an angle with respect to horizontal, e.g., vent holes may direct exhaust in direction d2 or at angles α1, α2 with respect to d2 (e.g., α1, α2 about 0-) 20°. The dome 2340 may be any suitable size, but should not be wider than the base wall. The outer surface of the dome 2340 may have a smooth finish, e.g., the vent holes 2330 are not raised or sunken into the outer surface of the dome 2340. However, in an alternative embodiment, the holes 2330 may be raised or sunken into the outer surface of the dome 2340.

In the illustrated embodiment, each of the vent caps is structured to be releasably attached to the mask by means of a bayonet connection. Attachment of the vent cap 2300 to an elbow 2390 of the mask will now be described in greater detail. However, it should be appreciated that the vent cap may be releasably attached to another portion of the mask in a similar manner, e.g., mask frame. Also, it should be appreciated that the vent cap may be attached to the mask in other suitable manners, e.g., snap fit, ultrasonically welded (in which case, it would not be a releasable component), interference fit, sliding fit, permanently machined into the mask, etc.

As shown in FIGS. 4-2A to 4-2C and 4-3A to 4-3C, the vent cap 2300 includes outer and inner side walls (e.g., see FIG. 4-2B) 2352, 2354 that extend downwardly from the base wall 2335 and define a channel 2356 there between. Two diametrically opposed projections 2360 extend radially inwardly from the outer side wall 2352. In addition, the vent cap 2300 includes a window 2358 adjacent each projection 2360 that allows the user to visually recognize when the vent cap 2300 is in a locked position as described below.

As shown in FIGS. 4-5A to 4-5B and 4-7D, the elbow 2390 includes an opening 2392 for gas washout. An annular lip 2394 surrounds the opening 2392 and one or more ribs 2396 (e.g., two diametrically opposed ribs) extend radially outwardly from the lip 2394. In the illustrated embodiment, each rib 2396 is generally L-shaped including a first leg 2396(1) and a second leg 2396(2). The second leg 2396(2) is a bayonet "stop" which prevents the vent cap from over-turning and subsequently disengaging. The second leg 2396(2) also offers feedback to the user that they have reached the "end" and the vent cap is properly locked.

FIGS. 4-6A to 4-6B and 4-7A to 4-7C illustrate attachment of the vent cap 2300 to the elbow 2390. FIGS. 4-6A to 4-6B illustrate the vent cap 2300 in an unlocked position with the vent cap 2300 resting on the elbow lip 2394, i.e., channel 2356 receives elbow lip 2394 and ribs 2396 there between. As illustrated, the outer side wall 2352 of the vent cap 2300 overhangs the elbow lip 2394 such that the projections 2360 are circumferentially spaced from the elbow ribs 2396.

The vent cap 2300 is rotatable with respect to the elbow 2390 to move the vent cap 2300 to a locked position as shown in FIGS. 4-7A to 4-7C. As illustrated, the vent cap 2300 is rotated to position the projections 2360 underneath respective first legs 2396(1) of the ribs 2396, and thereby axially lock the vent cap 2300 in position on the elbow 2390. The second legs 2396(2) of the ribs 2396 prevent further rotation of the vent cap 2300 with respect to the elbow 2390, i.e., further rotation causes projections 2360 to engage respective second legs 2396(2). As shown in FIG. 4-7B, the window 2358 in the vent cap 2300 allows the user to visually recognize when the first legs 2396(1) of the ribs 2396 are aligned with the projections 2360 and hence locked.

The bayonet connection provides a relatively simple and intuitive arrangement to use. It also minimizes leak from the vent cap since the connection is radial and does not require an interference to lock the vent cap in position, e.g., like a clip-on vent cover.

In an embodiment, vent cap will diffuse air so that the air flow is undetectable by a person at a distance of less than about 500 mm from the vent, e.g., less than 200 mm, less than 100 mm, less than 50 mm, less than 30 mm.

In an embodiment, vent cap will produce less than about 40 dBA sound power at 10 $cmH_2O$ tested according to ISO3744, e.g., less than 30 dBA, less than 25 dBA, less than 20 dBA.

Figures 4, 4A:
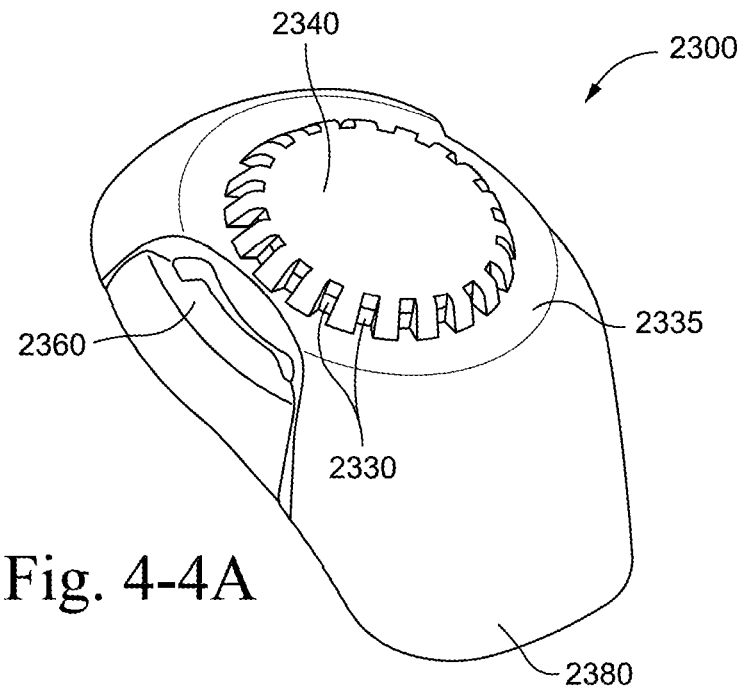
Figures 4, 4B:
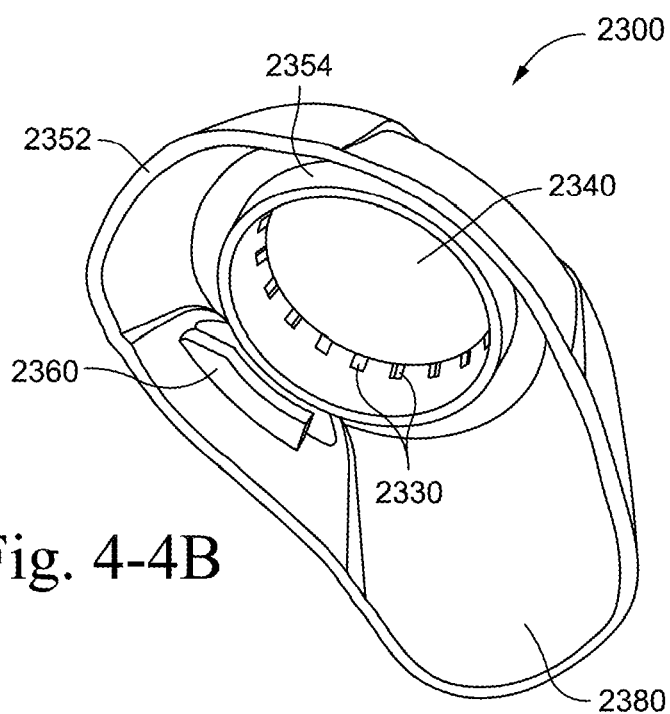
Figures 4, 5, 5A:
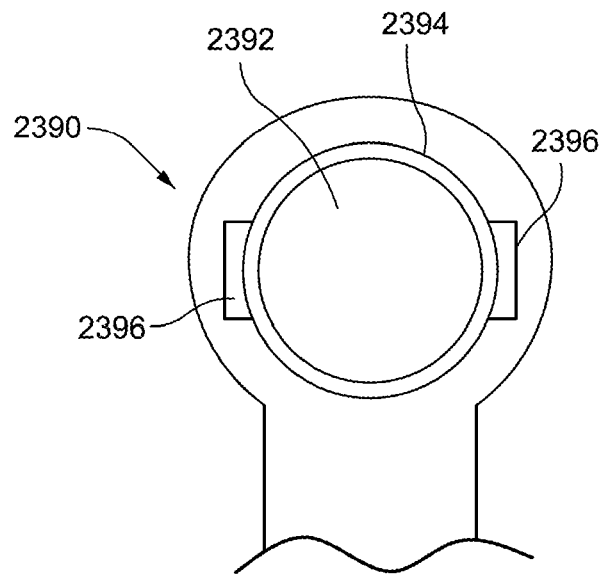
Figures 4, 5, 5B:
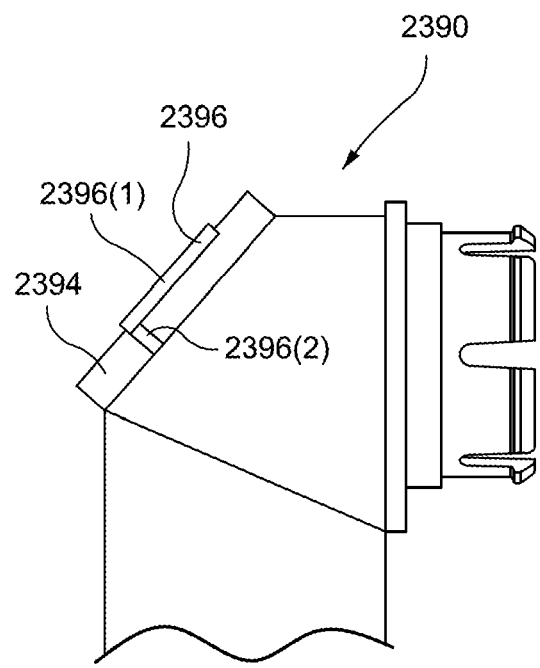
Figures 4, 5, 6, 6A:
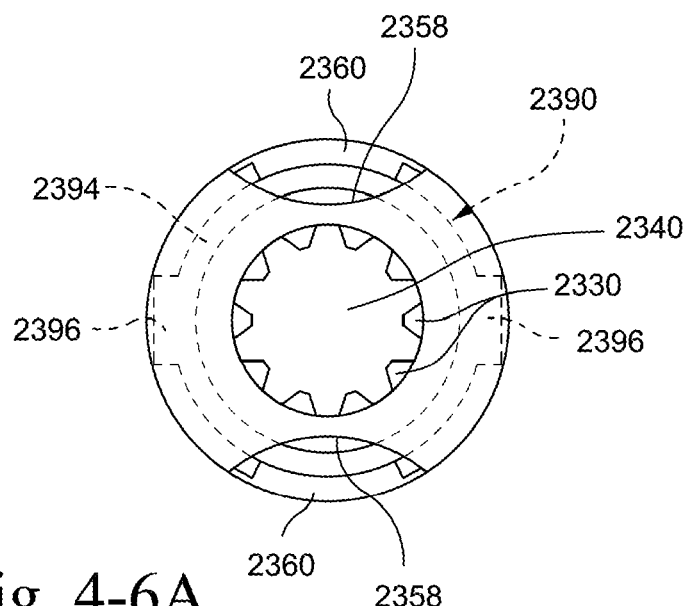
Figures 4, 5, 6, 6B:
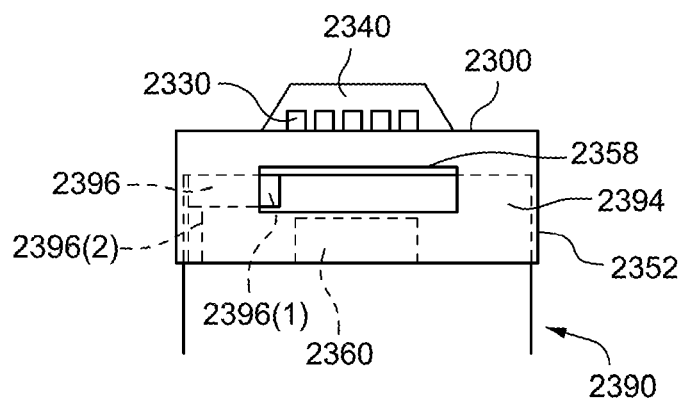
Figures 4, 5, 6, 7, 7A:
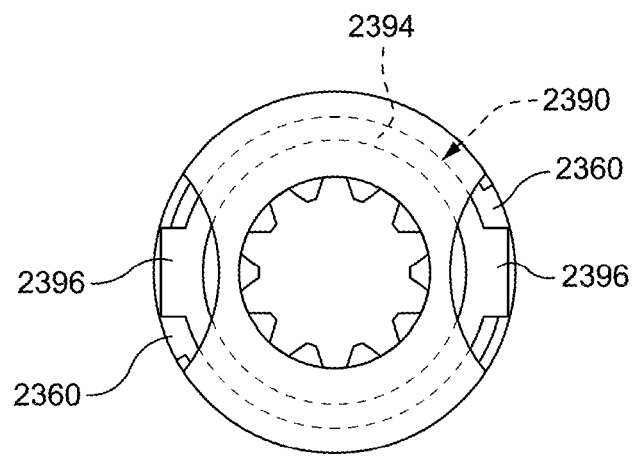
Figures 4, 5, 6, 7, 7B:
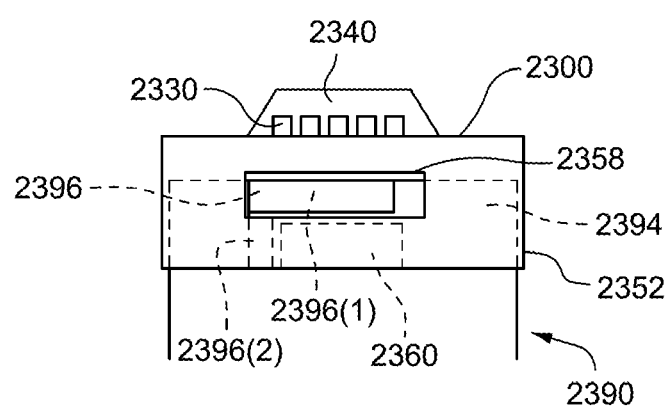
Figures 4, 5, 6, 7, 7C:
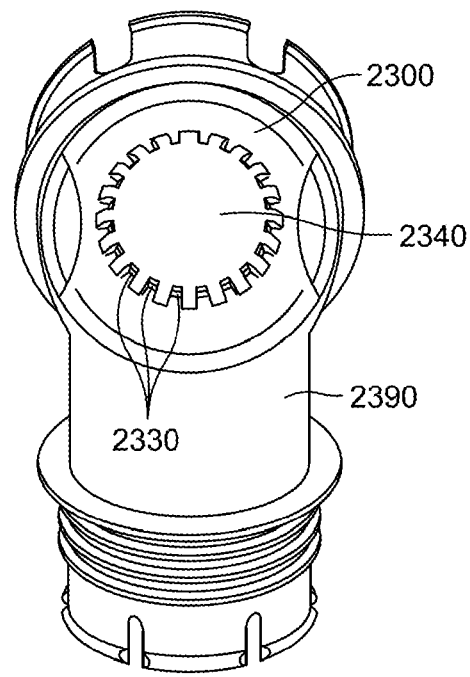
Figures 4, 5, 6, 7, 7D:
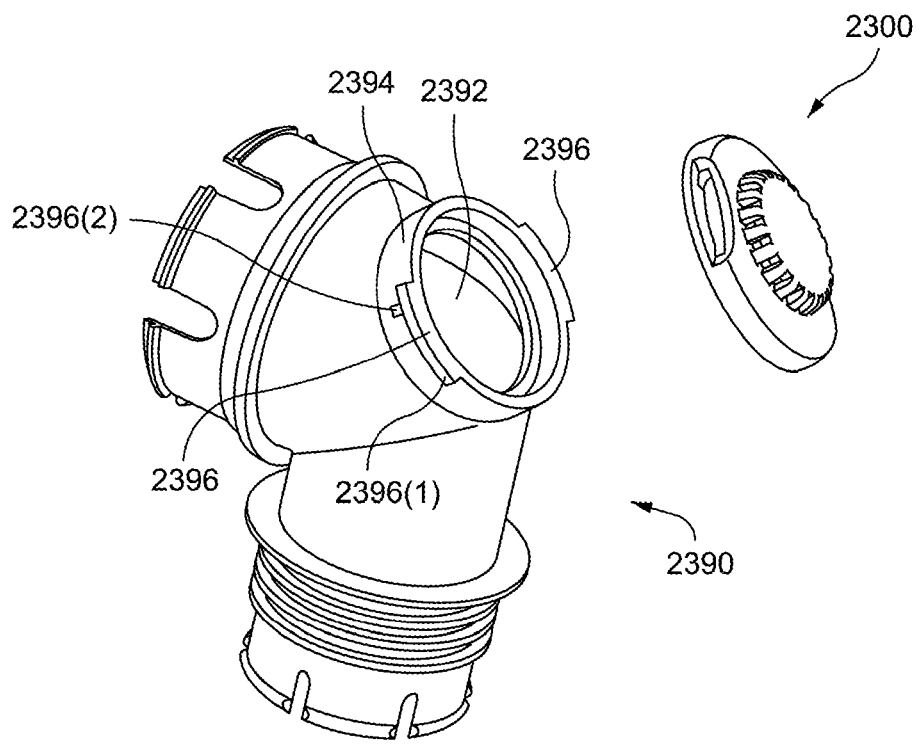
Figures 1, 5:
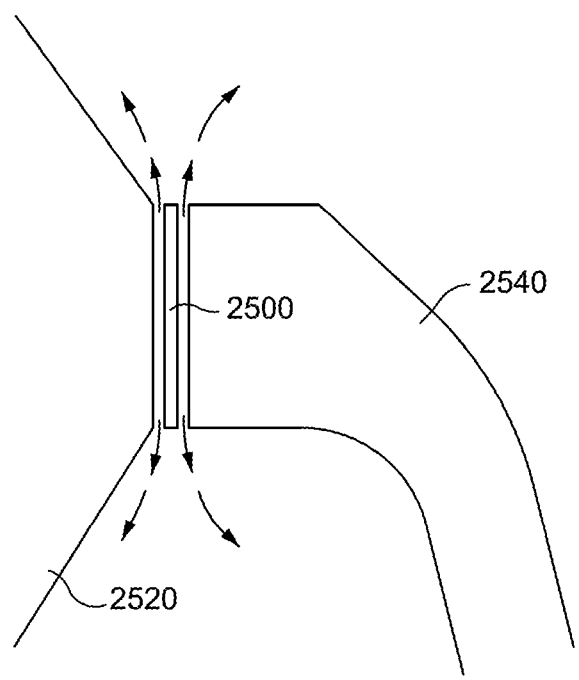
Figures 2, 5:
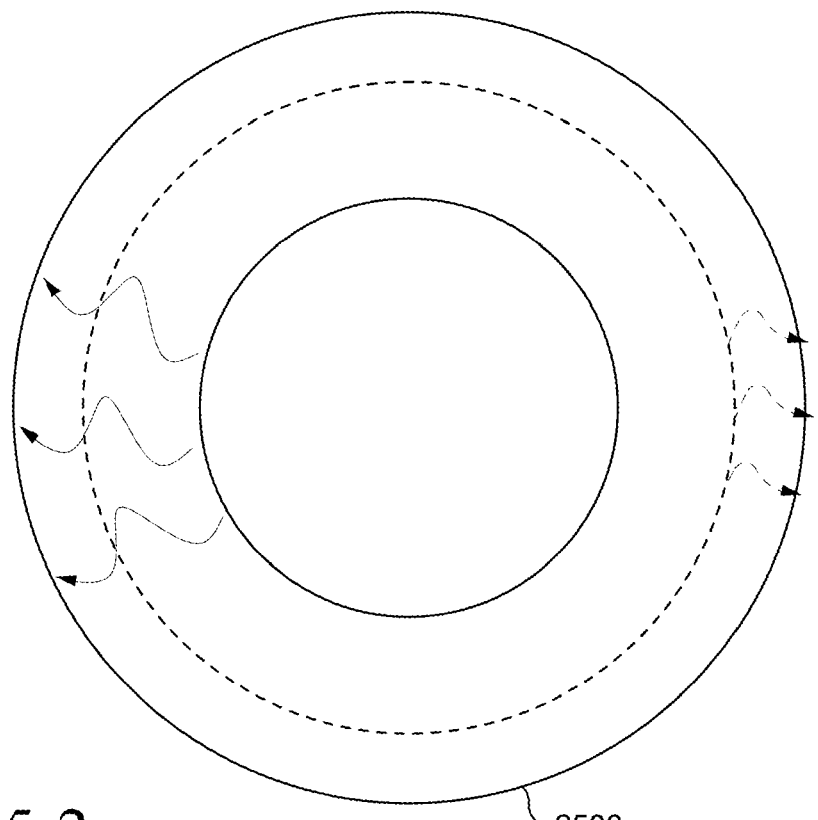
Figures 1, 3, 5:
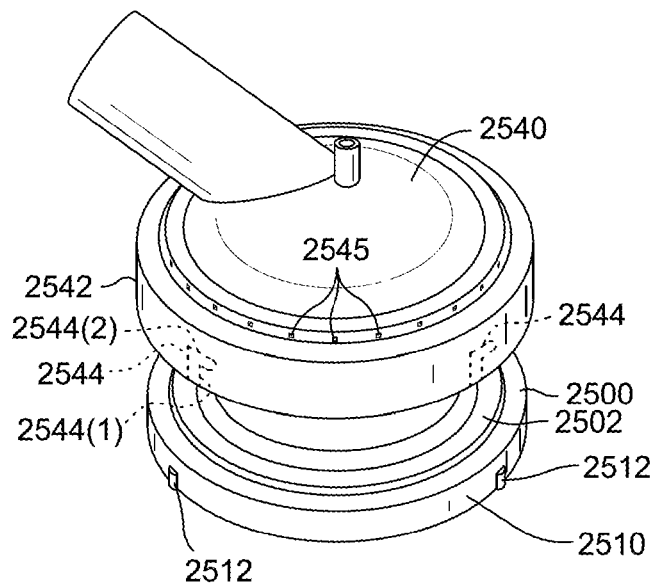
Figures 2, 3, 5:
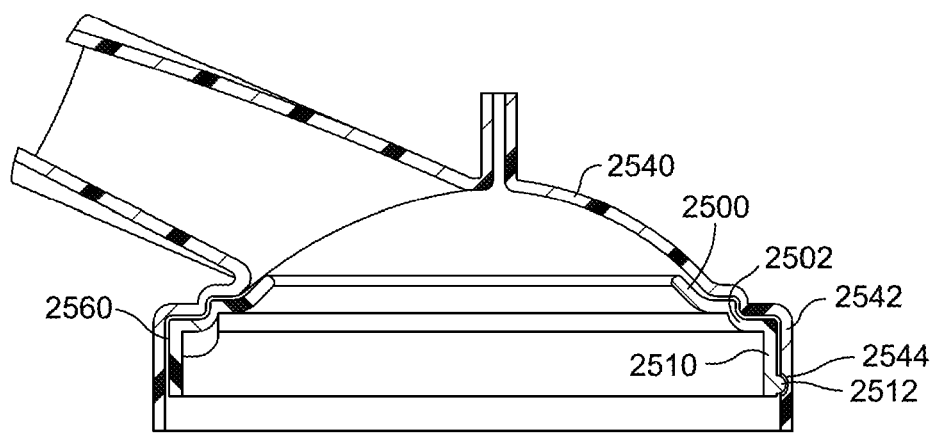
Figures 4, 5:
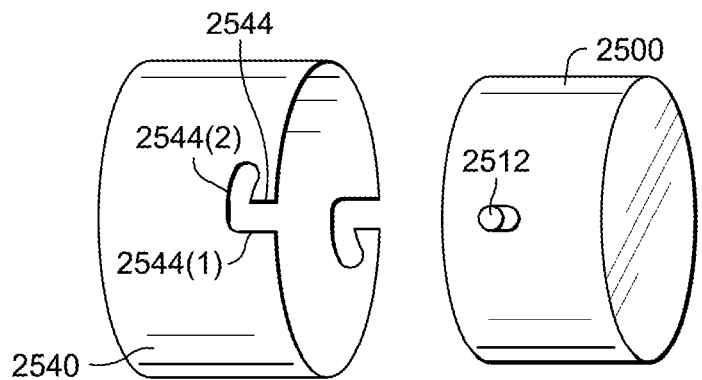
Figure 5:
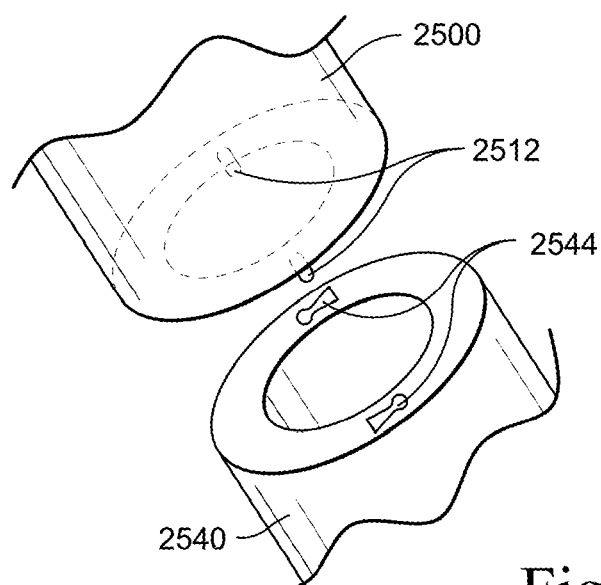
Figures 1, 5, 6:
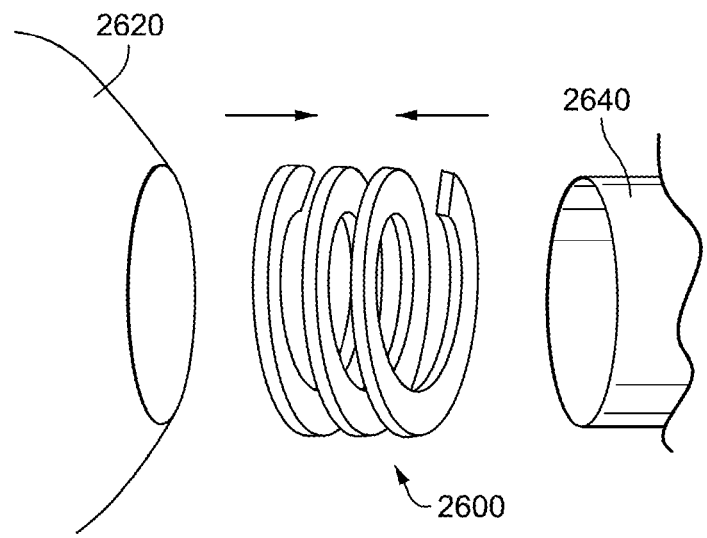
Figures 2, 5, 6:
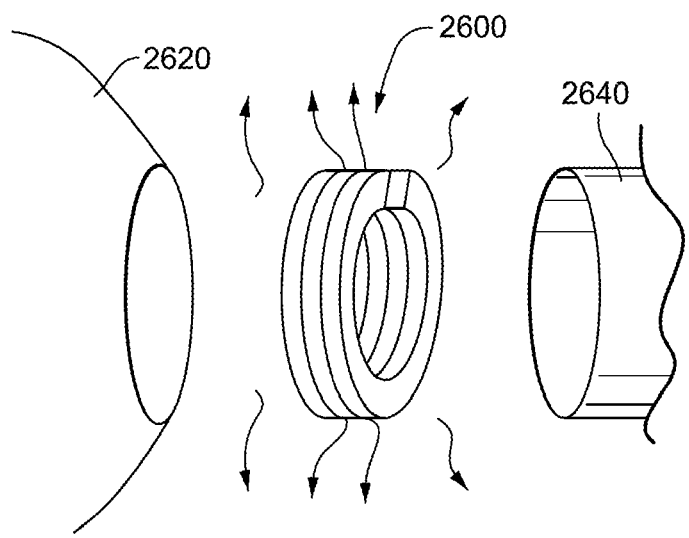
Figures 1, 5, 6, 7:
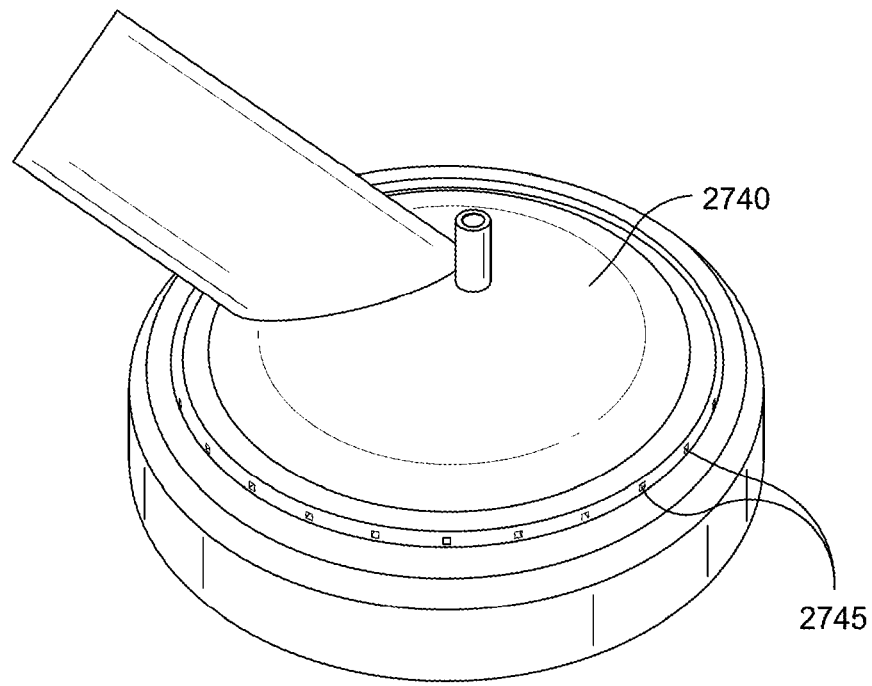
Figures 2, 5, 6, 7:
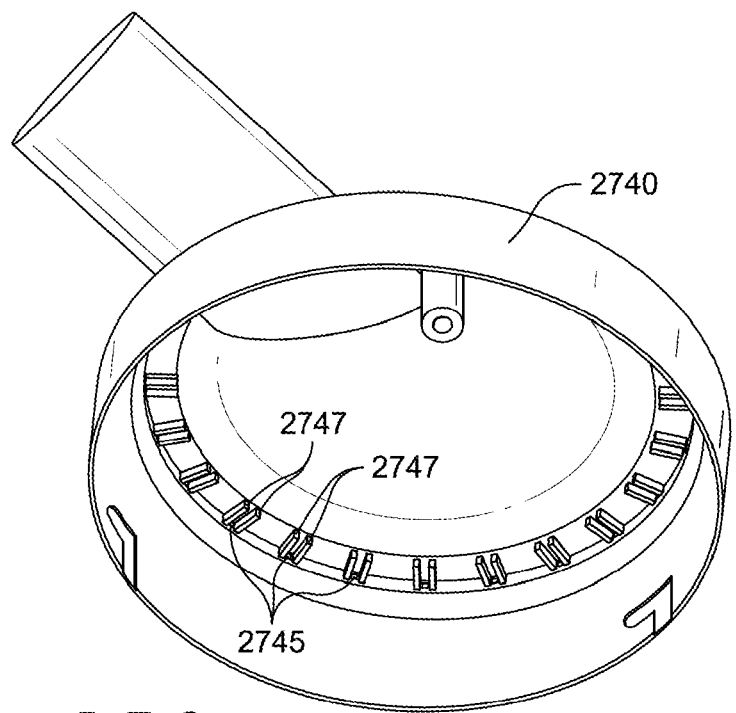
Figures 1, 5, 6, 7, 8:
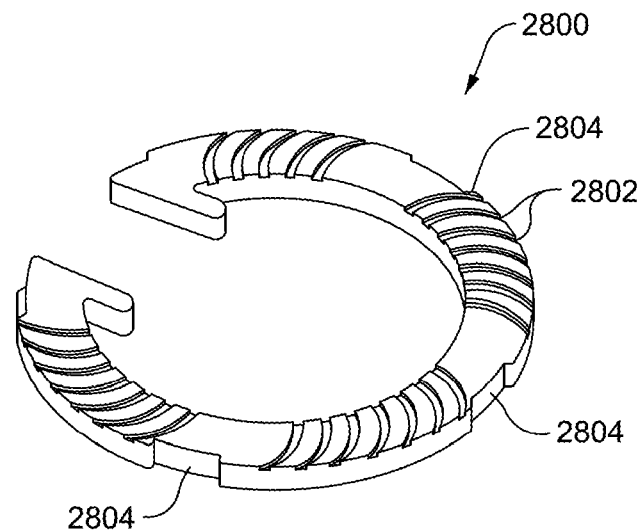
Figures 2, 5, 6, 7, 8:
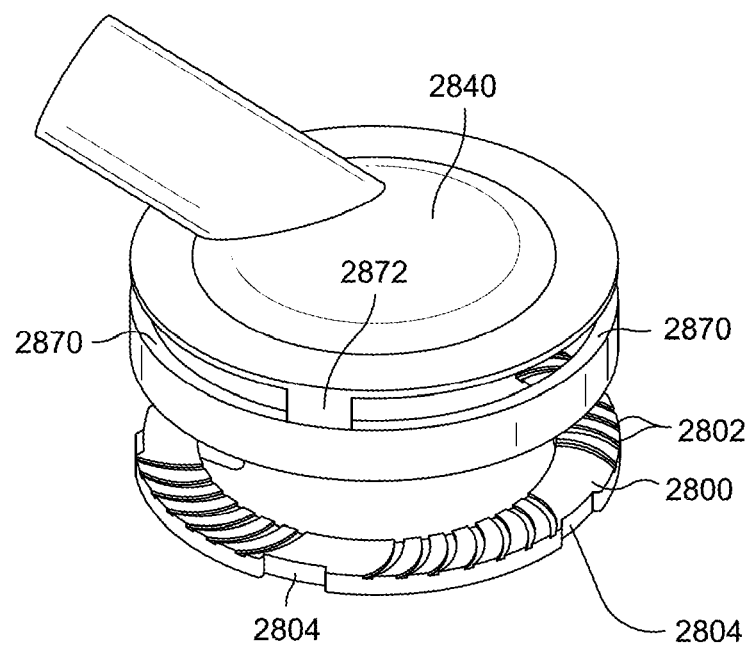
Figures 3, 5, 6, 7, 8:
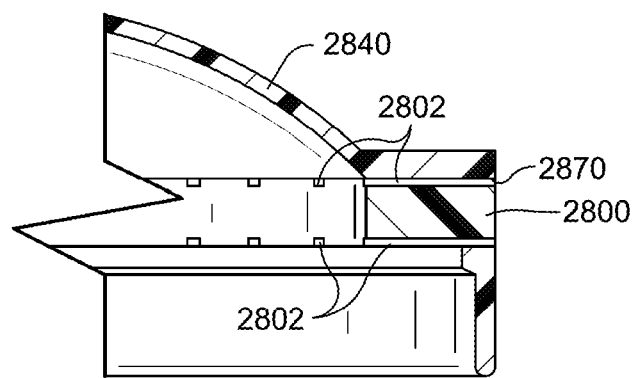
Figures 1, 5, 6, 7, 8, 9:
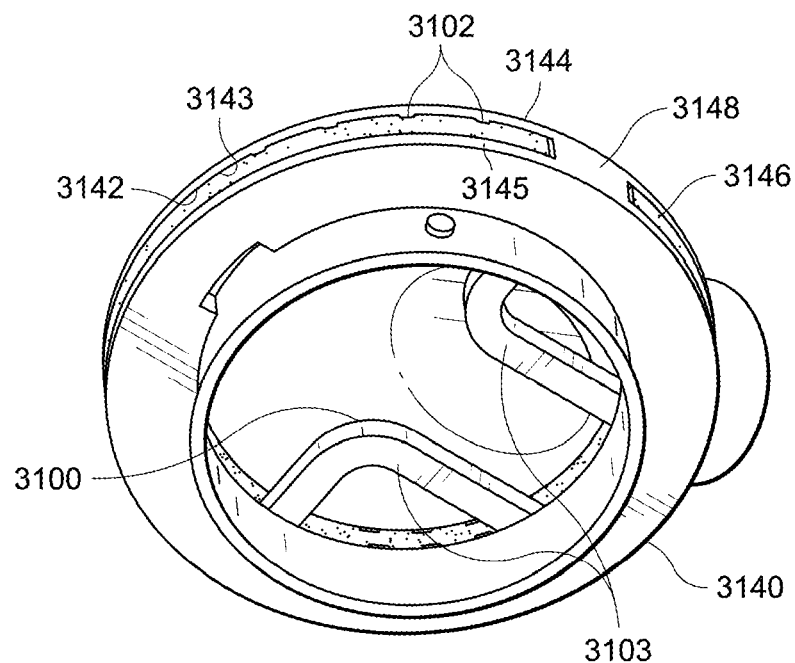
Figures 2, 5, 6, 7, 8, 9:
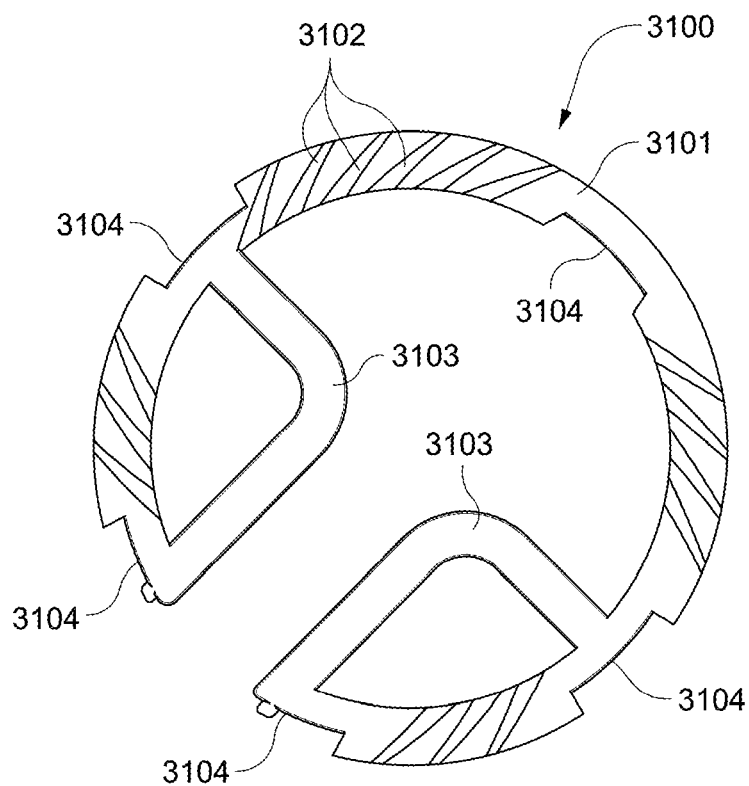
Figures 3, 5, 6, 7, 8, 9:
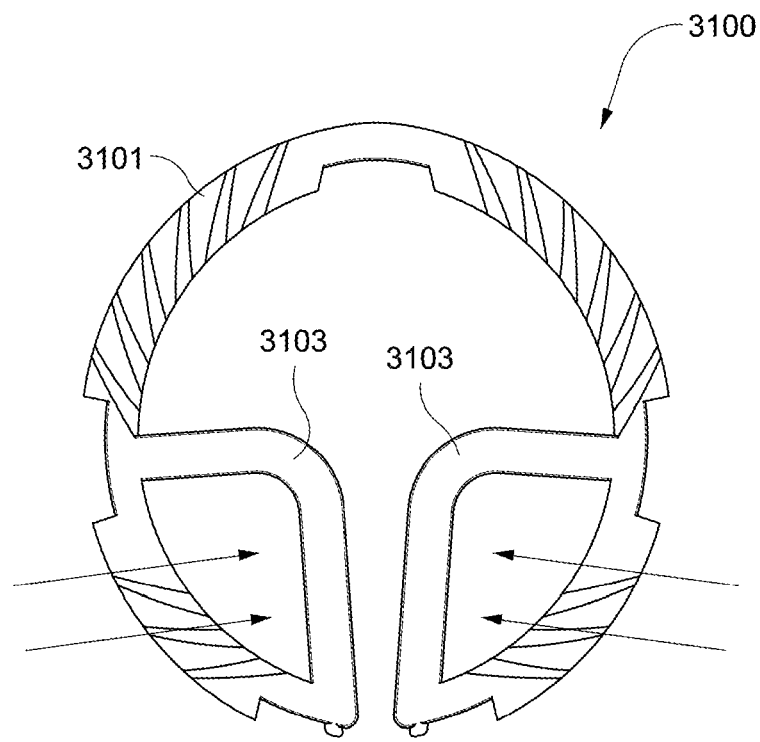
Figures 4, 5, 6, 7, 8, 9:
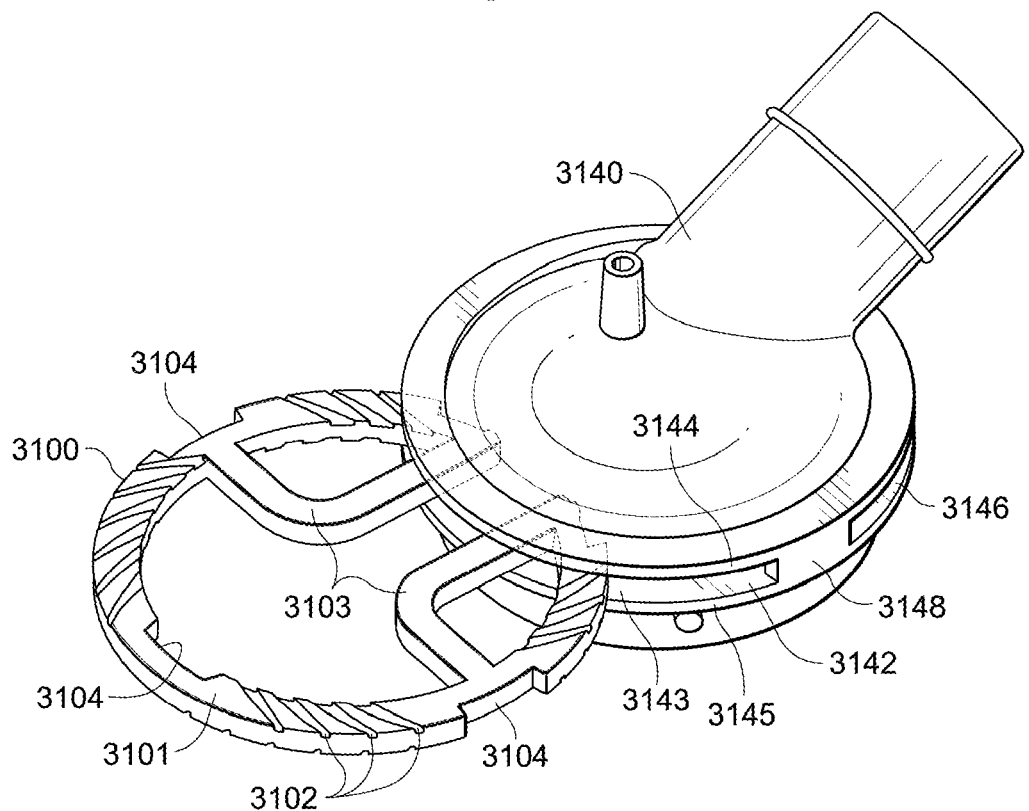
Figures 5, 6, 7, 8, 9:
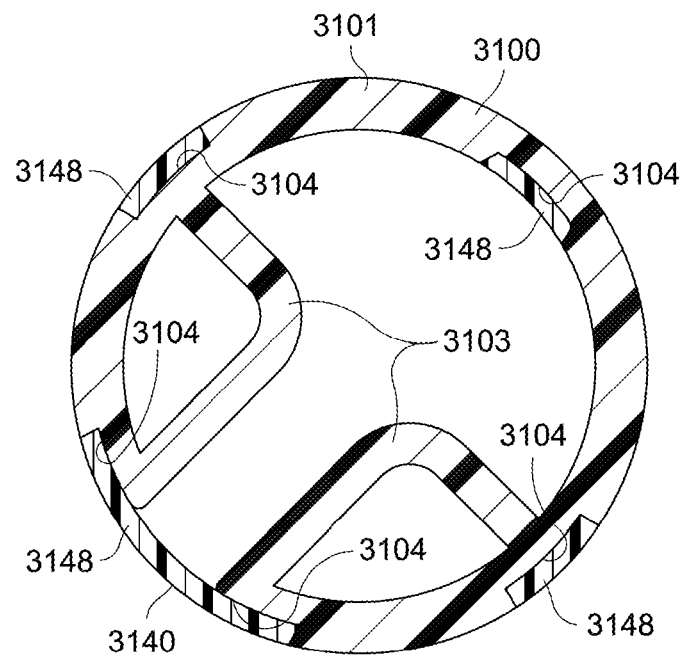
Figures 5, 6, 7, 8, 9:
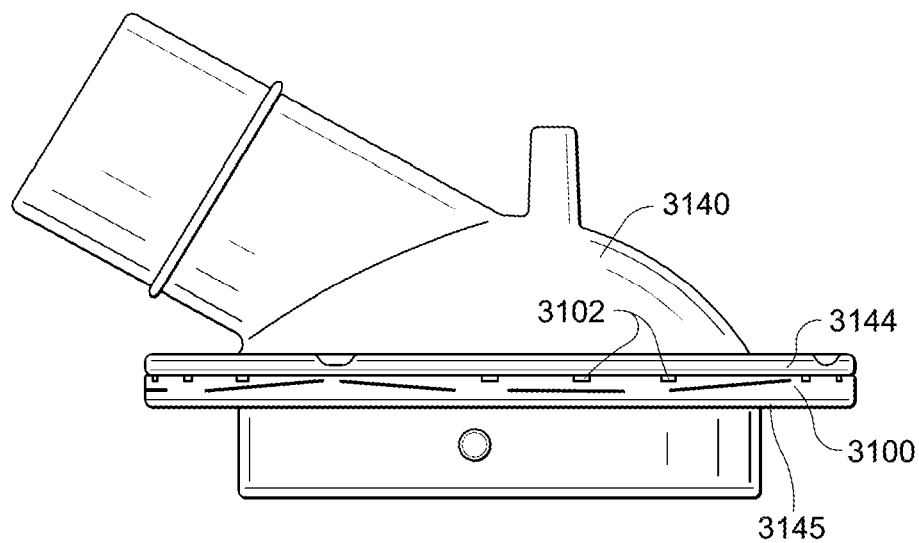
Figures 1, 5, 6, 7, 8, 9, 10:
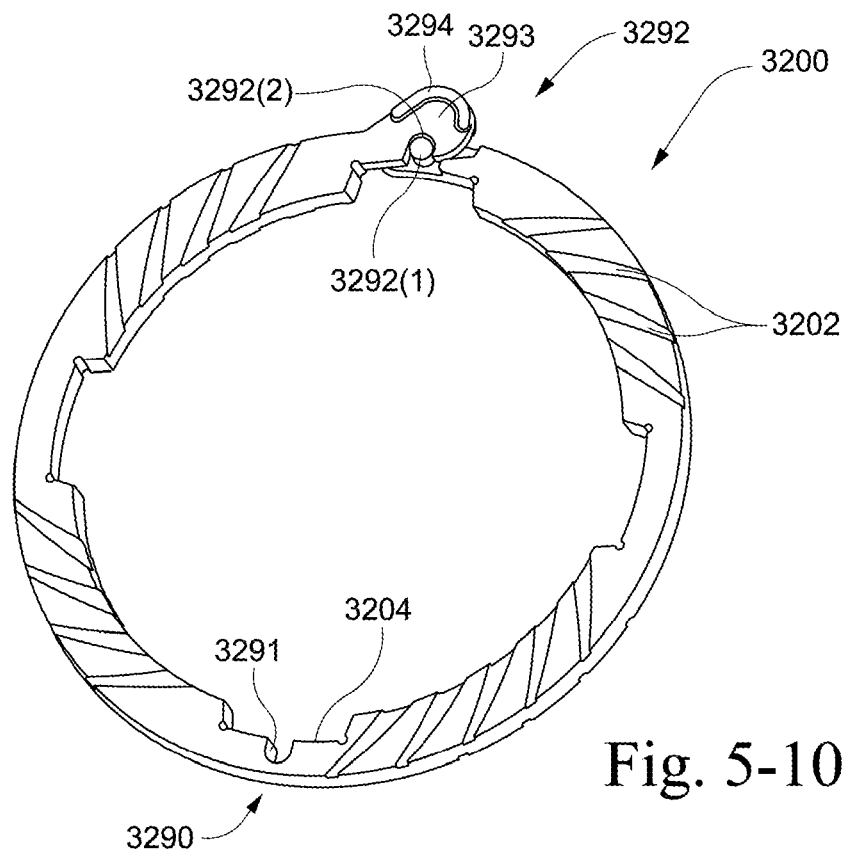
Figures 2, 5, 6, 7, 8, 9, 10:
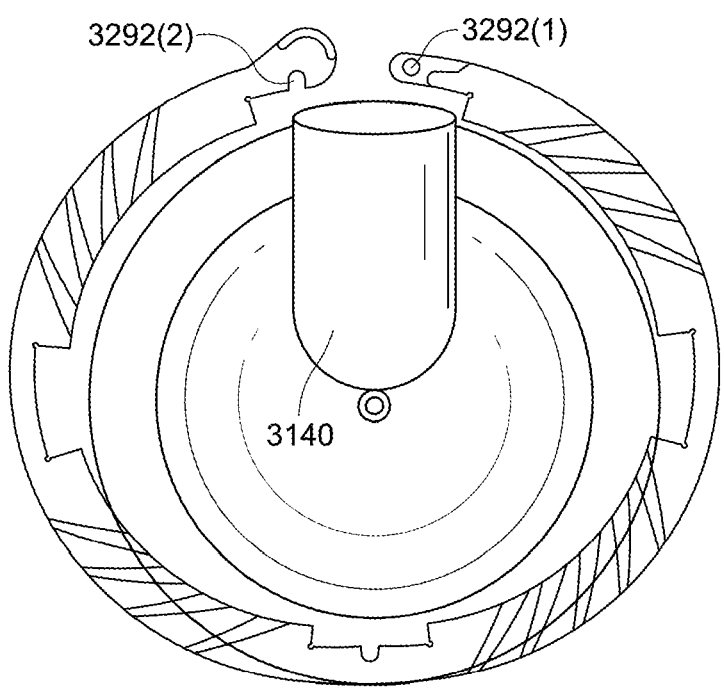
Figures 3, 5, 6, 7, 8, 9, 10:
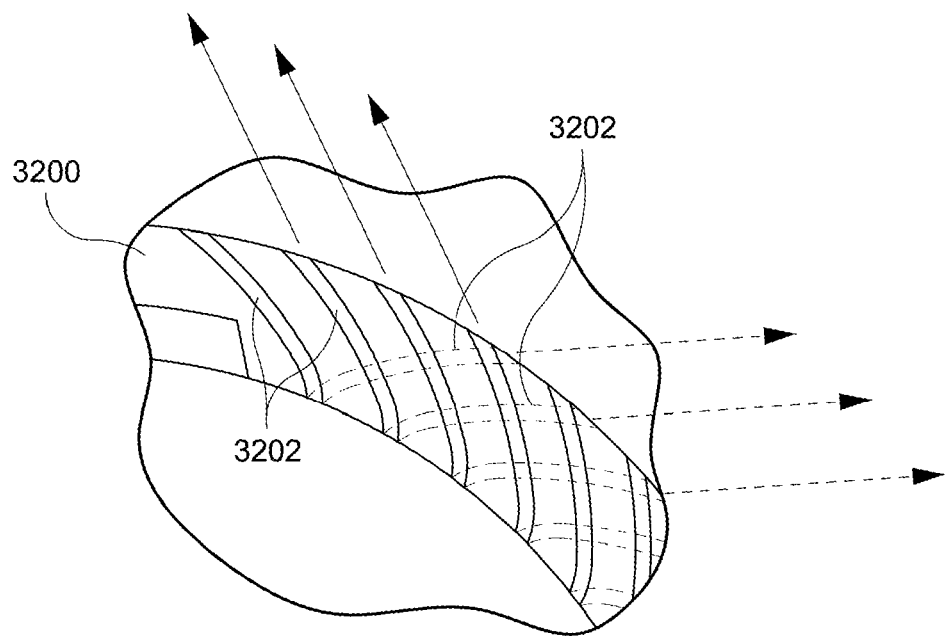
Figures 1, 5, 6, 7, 8, 9, 10, 11:
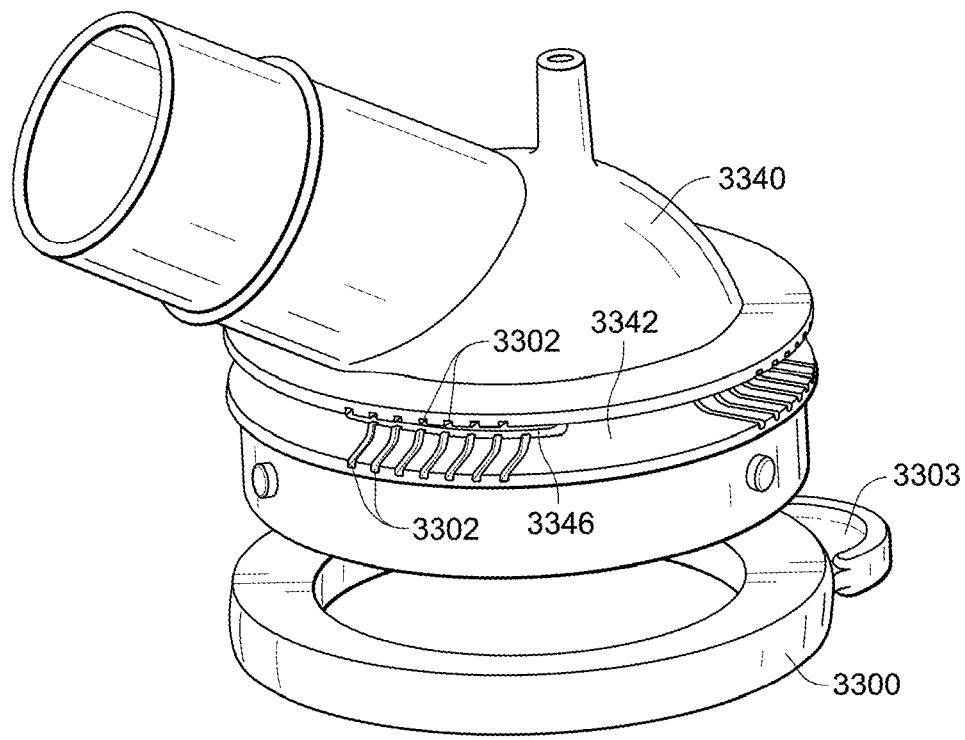
Figures 2, 5, 6, 7, 8, 9, 10, 11:
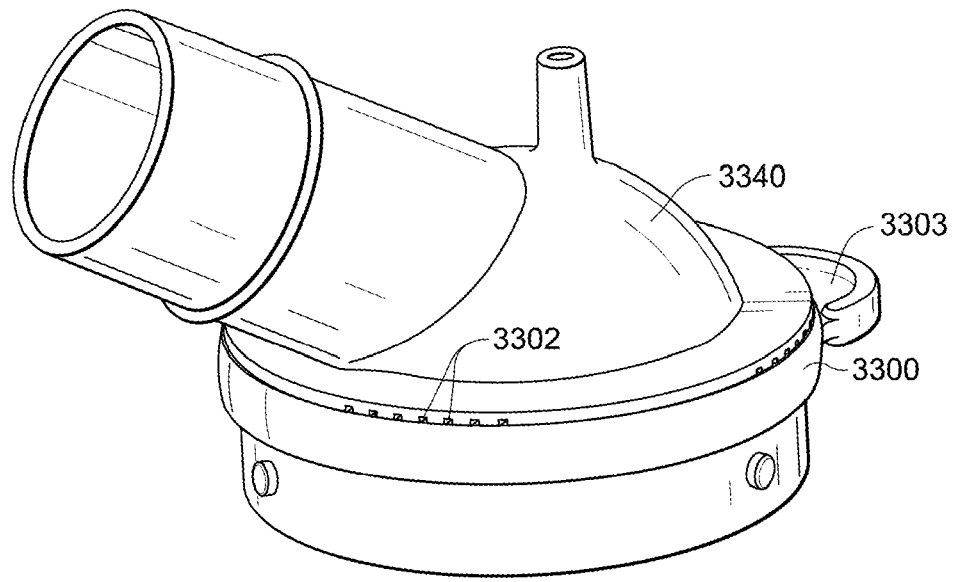
Figures 1, 5, 6, 7, 8, 9, 10, 11, 12:
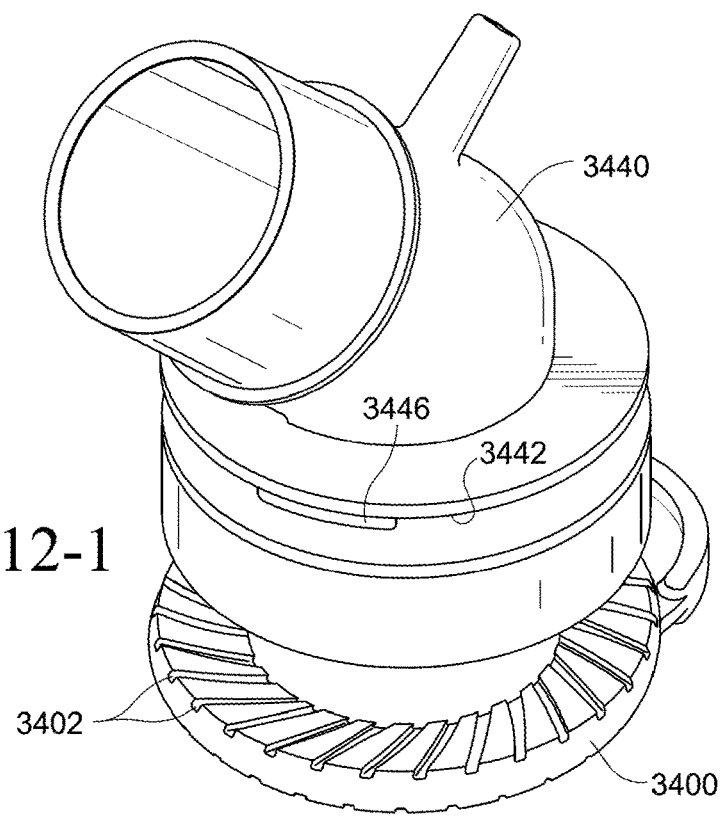
Figures 2, 5, 6, 7, 8, 9, 10, 11, 12:
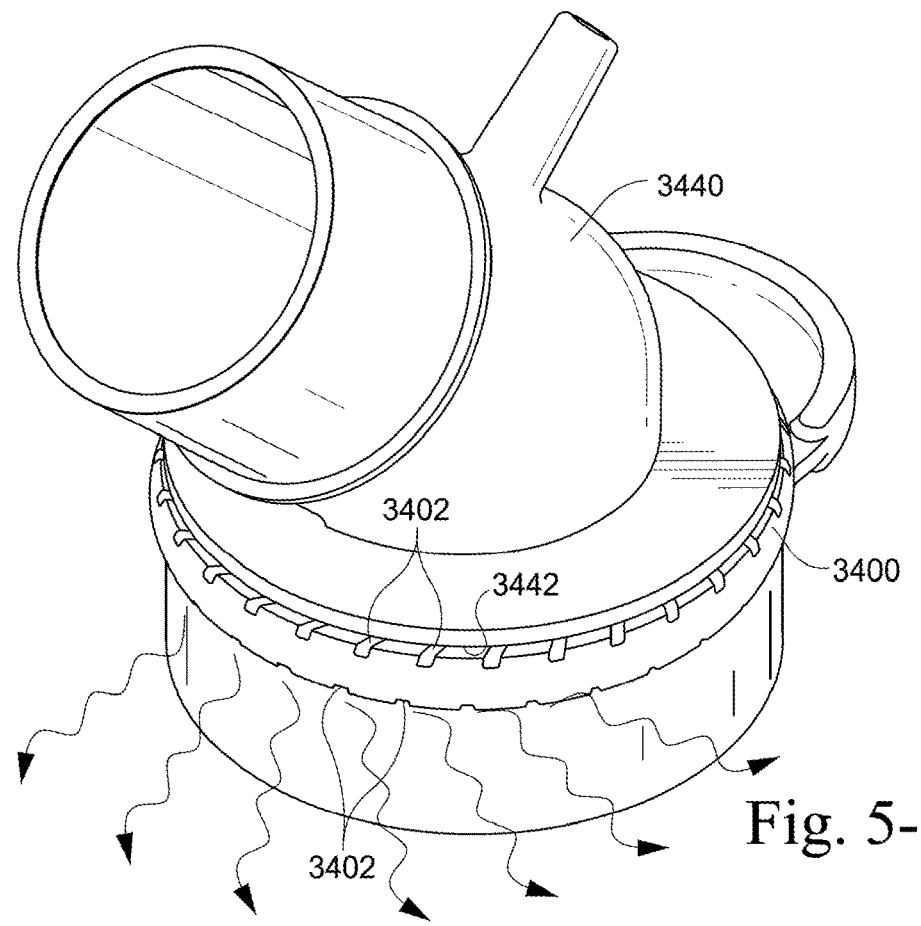
Figures 2, 6:
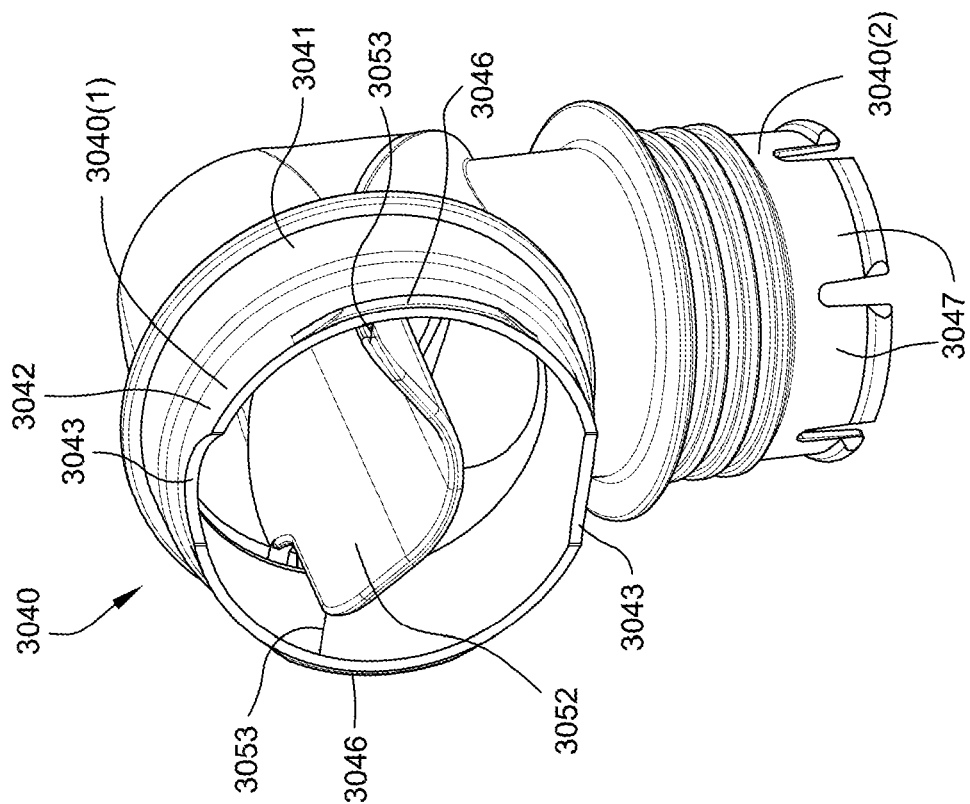
Figures 1, 6:
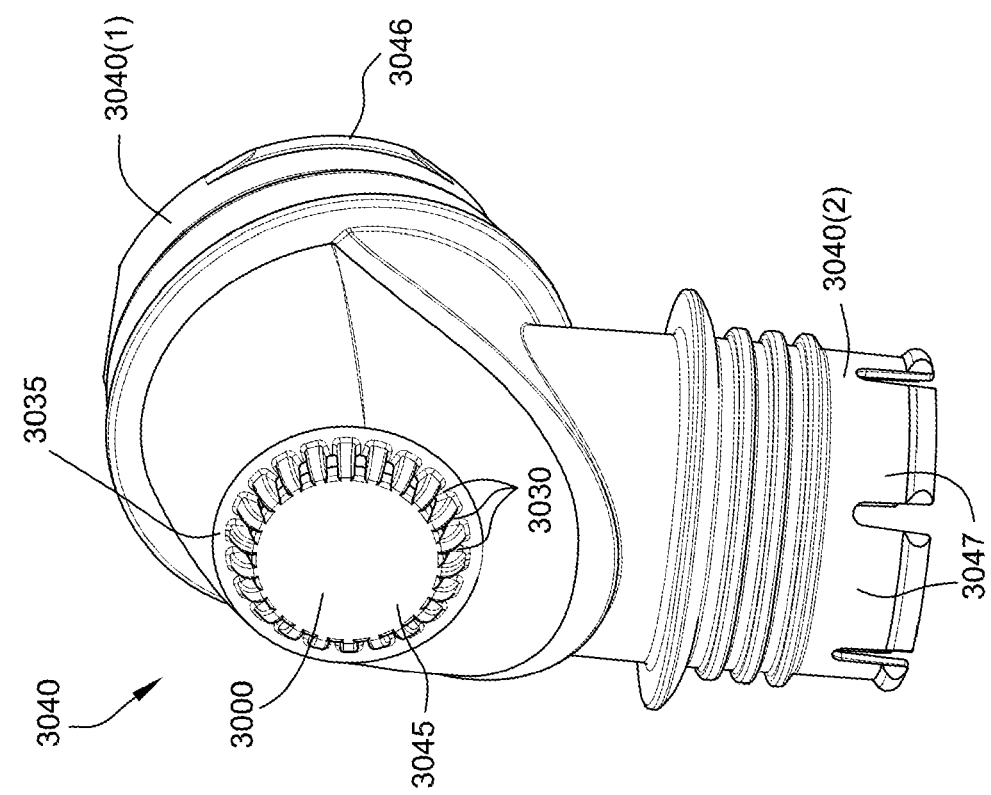
Figures 5, 6:
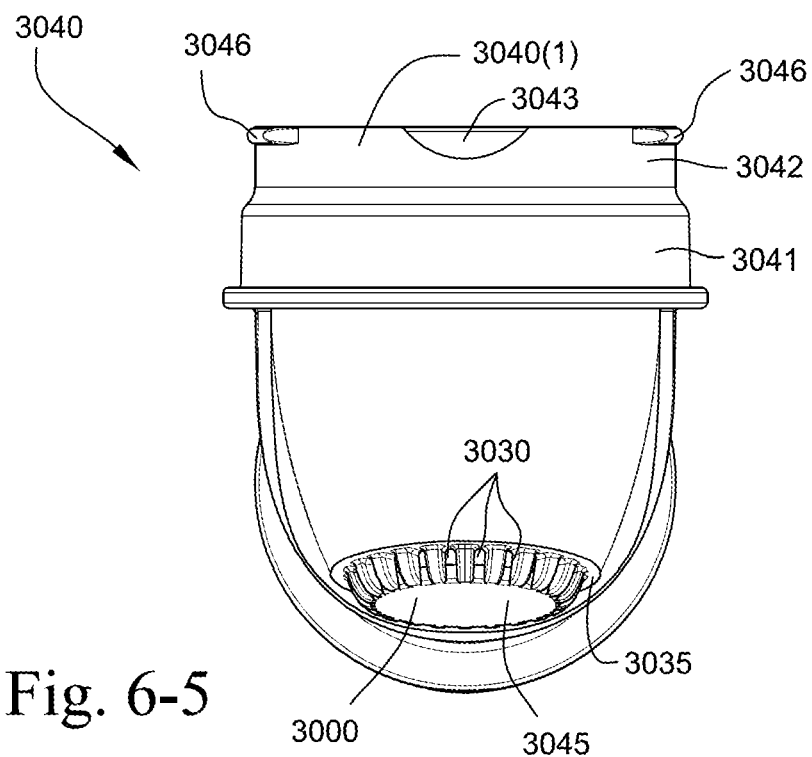
Figure 6:
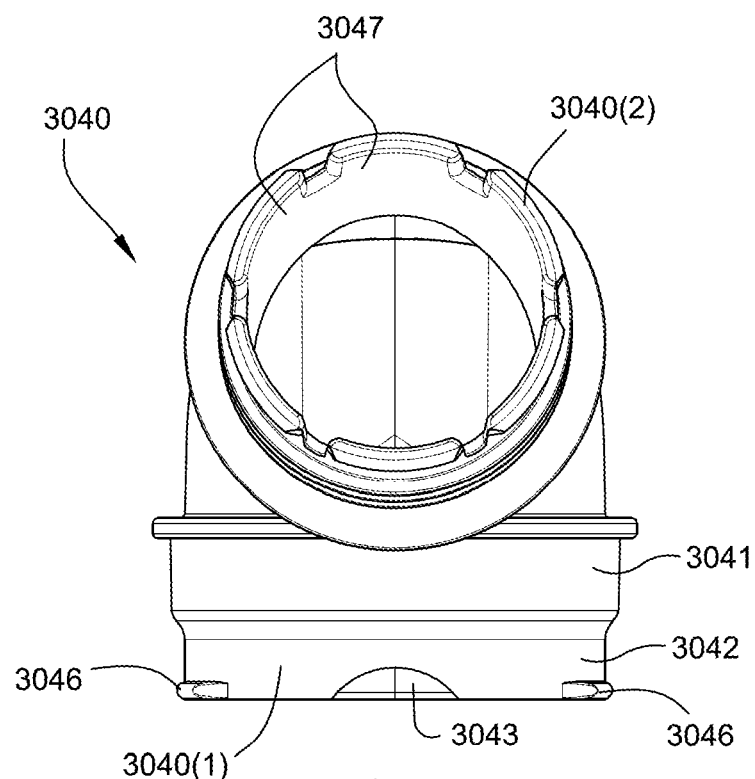
Figures 6, 7:
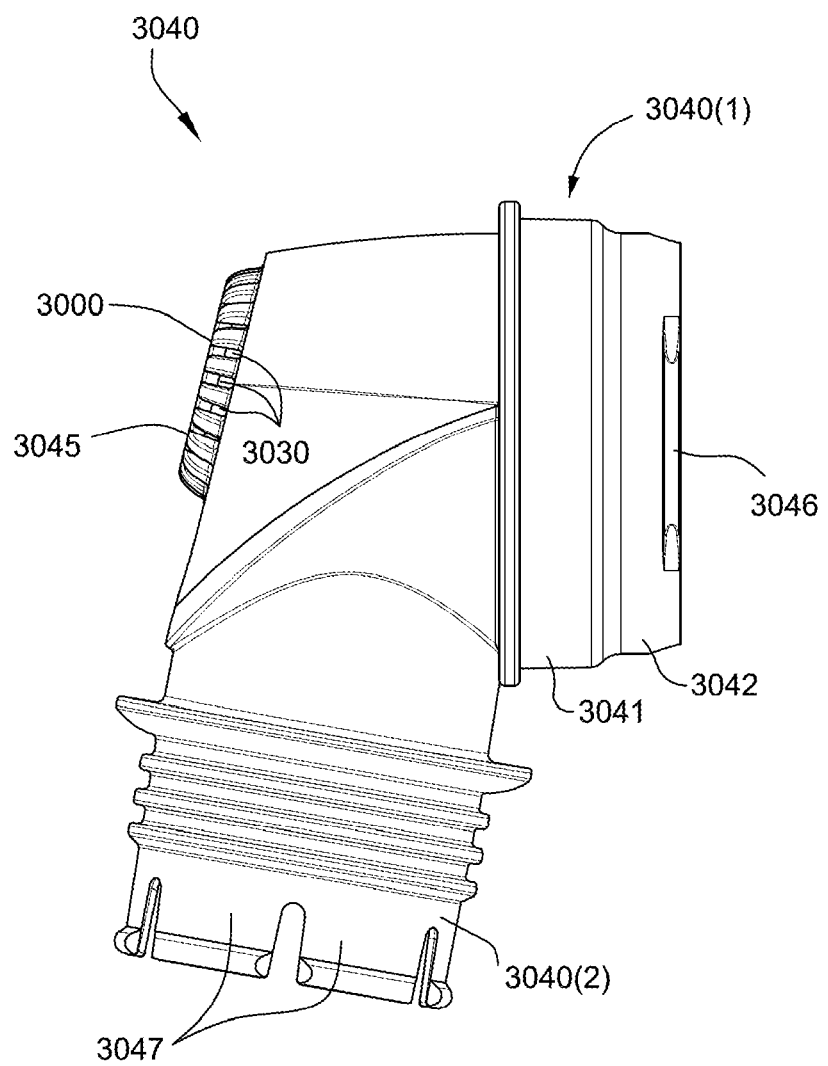
Figures 1, 7:
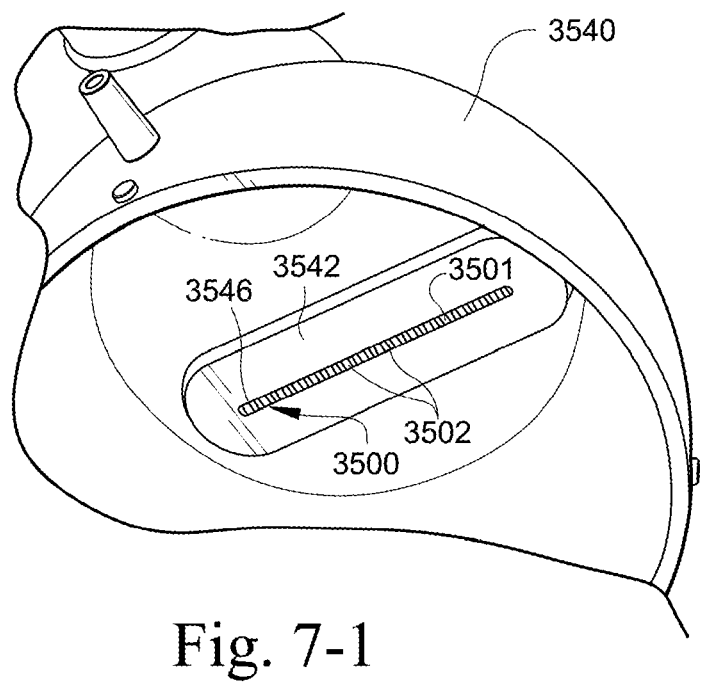
Figures 2, 7:
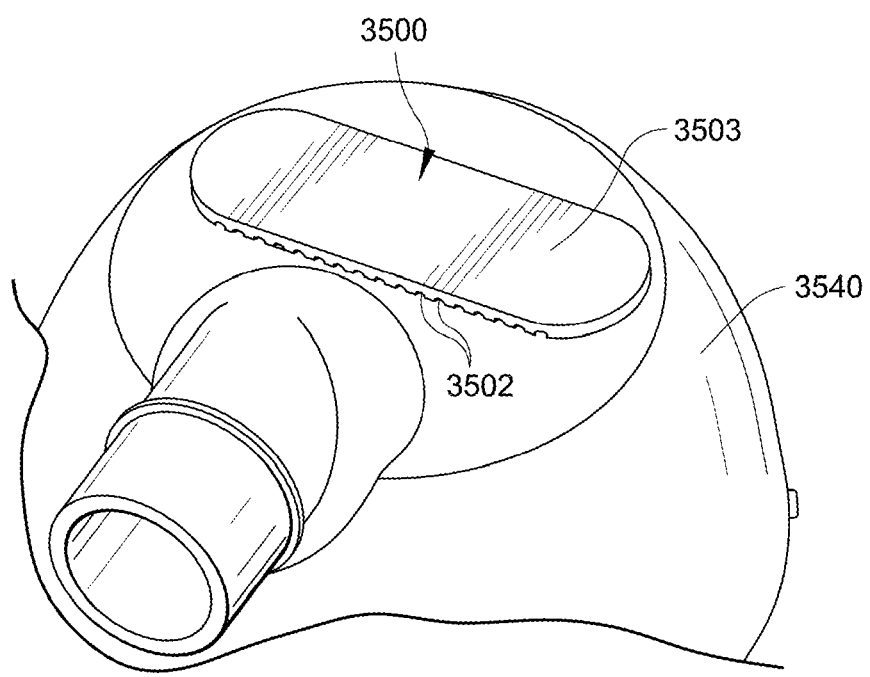
Figures 3, 7:
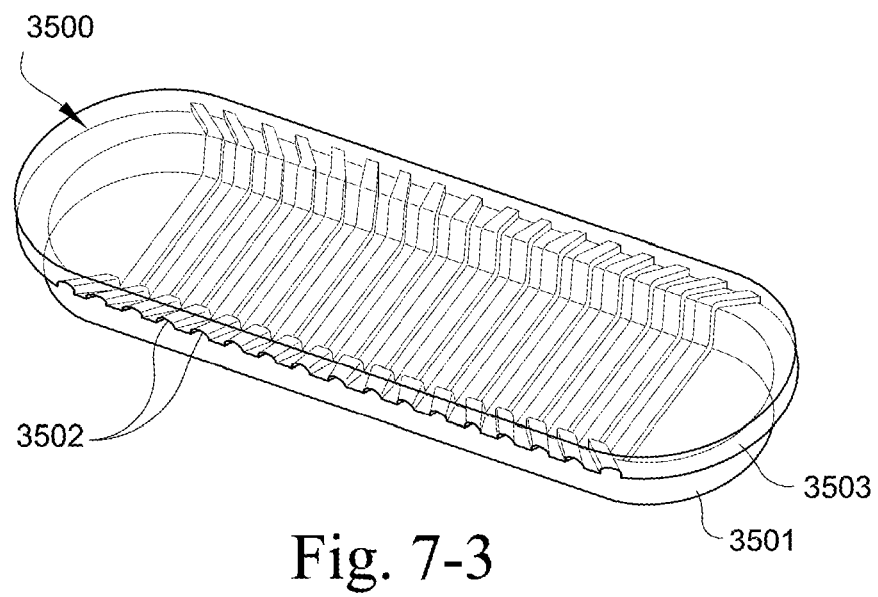
Figures 1, 8:
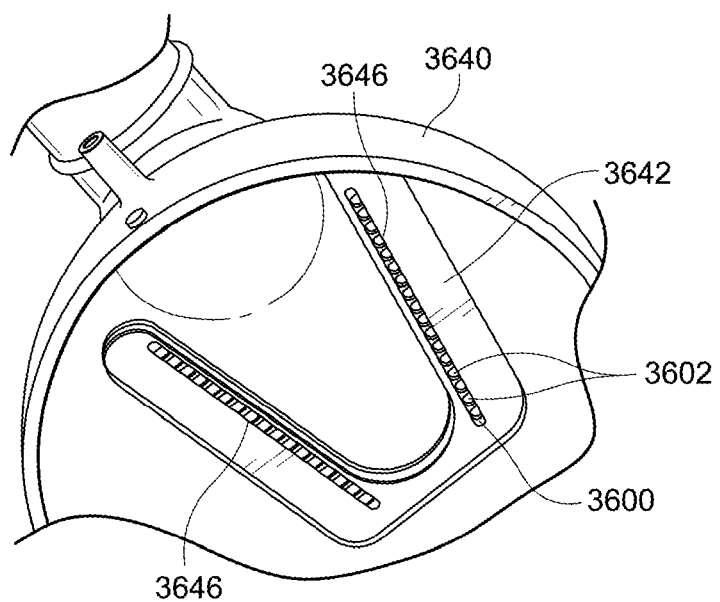
Figures 2, 8:
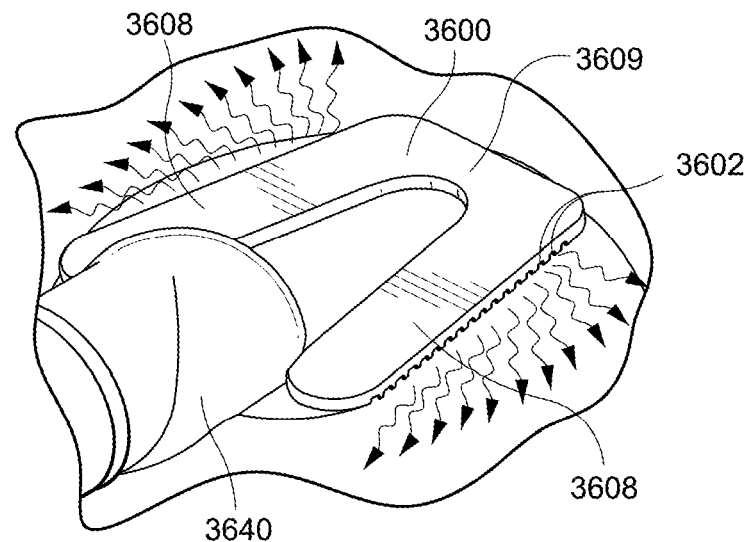
Figures 3, 8:
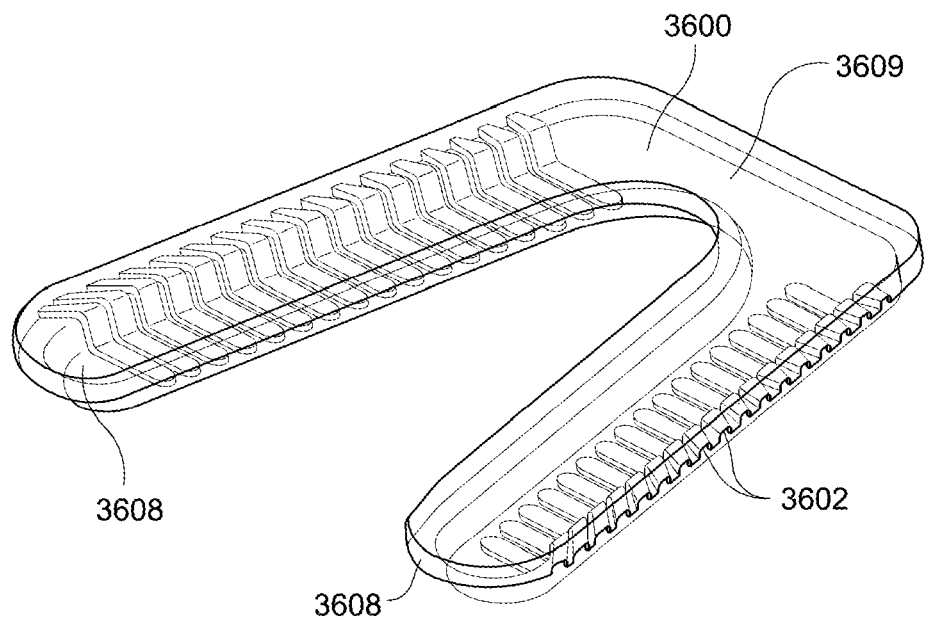
Figures 1, 9:
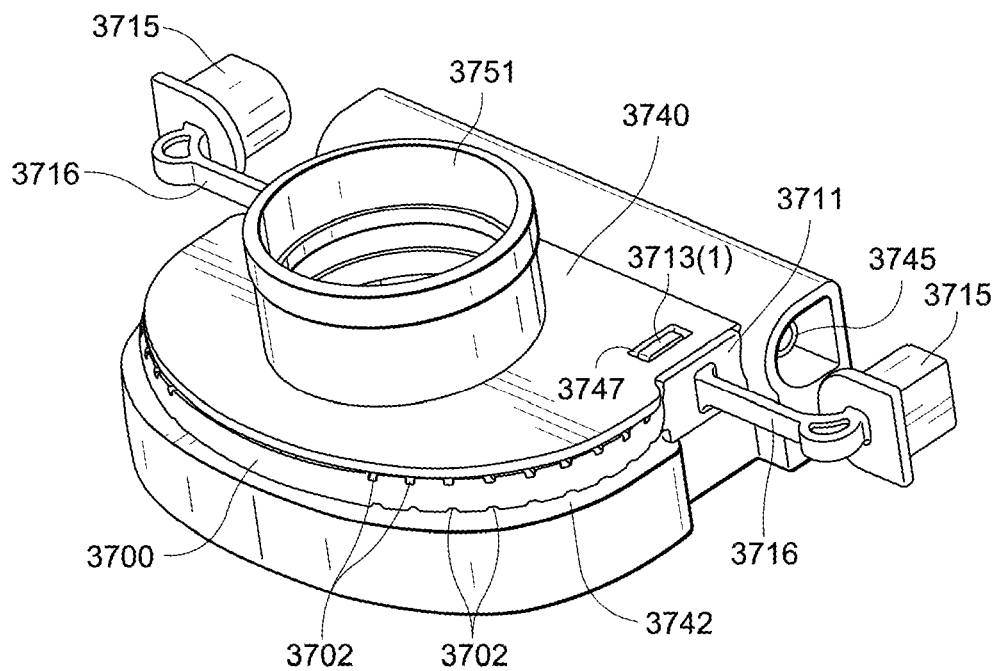
Figures 2, 9:
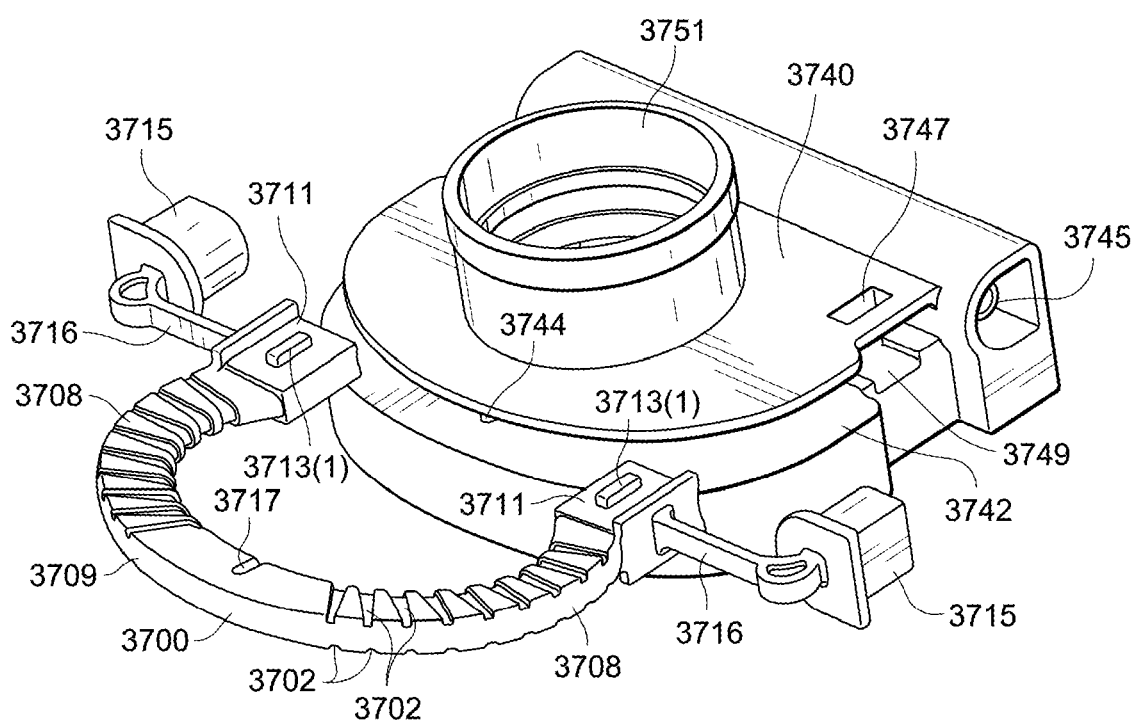
Figures 3, 9:
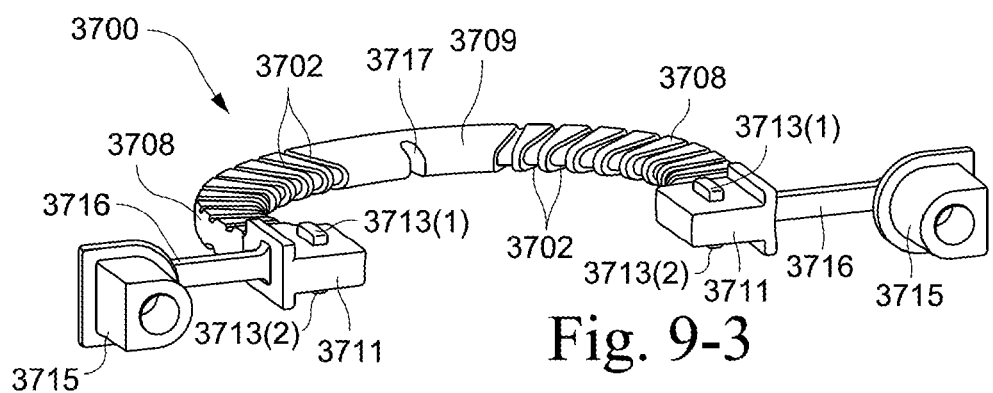
Figures 4, 9:
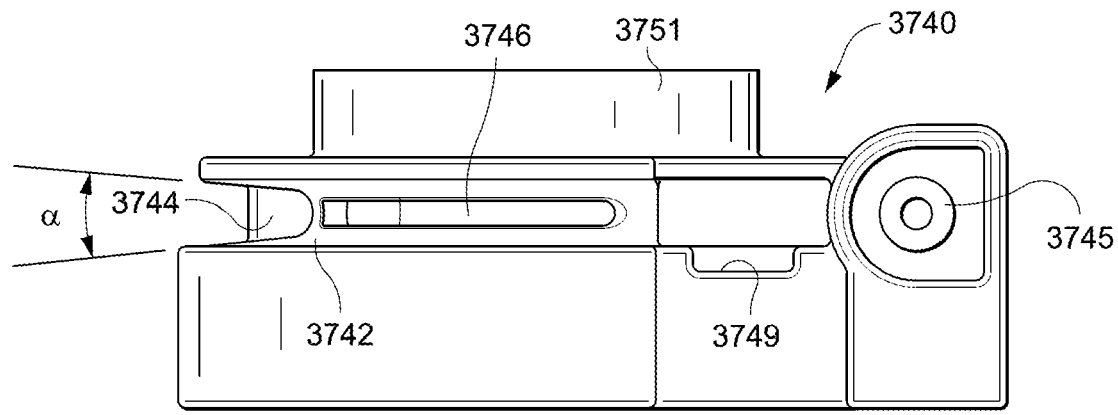

In FIGS. 4-1A to 4-3B, the vent cap has a generally circular shape. However, the vent cap may have other suitable shapes that allow a bayonet connection or other connection mechanism. For example, as shown in FIGS. 4-4A and 4-4B, the vent cap 2300 may include an extended edge 2380 that protrudes outwardly from the base wall 2335.

4.2 Super Quiet Diffused Vent

The ideal vent will be quiet and diffuse. Noise can be minimized by promoting low velocity, fully developed, laminar flow from the vent. Diffuse flow can be achieved by releasing the air flow over a larger area. Vent arrangements are described below that are structured to minimize noise and diffuse flow from the vent though a combination of features.

Additionally, the vent will be able to maintain flow under saturated or humidified conditions, minimize $CO_2$ re-breathing, be manufacturable, be cleanable or disposable, and biocompatible.

In an embodiment, air flow that is exiting a mask system will be directed through a vent that is quiet and diffuse. In a preferred form, noise from the vent will be less than about 30-40 dBA, e.g., less than 35 dBA. In an embodiment, the vent may be considered "super quiet" when noise is less than about 30 dBA, e.g., about 20-25 dBA.

It is to be understood that the following embodiments include features that may be incorporated into a mask system individually or in combination.

4.2.1 Baffle

Figures 2, 3, 4, 5:
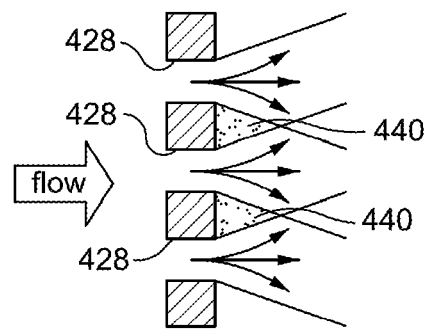

In an embodiment, a baffle 2500 may be provided between a mask 2520 and an elbow 2540 as schematically shown in FIG. 5-1. The baffle 2500 may be positioned between the elbow 2540 and a frame or cushion of the mask 2520 where air is typically vented from the mask 2520. As illustrated, the baffle 2500 is designed to force air exiting the mask 2520 to flow through a narrow pathway.

Preferably, as shown in solid lines in the diagram of FIG. 5-2, the baffle will be wide so that the air will flow through a longer pathway (as compared to a narrow baffle in which the pathway is shorter). Such a longer pathway encourages low velocity, fully developed, laminar flow.

In the illustrated embodiment, the baffle is generally circular. However, the baffle may have any suitable shape that closely matches the geometry of the elbow to frame or elbow to cushion connection, e.g., elliptical. In a preferred embodiment, the baffle will be relatively thin to minimize the weight of the mask system. Also, the baffle may not form a completely closed shape, e.g., the baffle may be hemispherical. This arrangement may allow for passage of another apparatus (e.g., anti-asphyxia valve (AAV)) or easier insertion and removal of the baffle.

In an embodiment, as shown in FIGS. 5-3-1 and 5-3-2, the baffle 2500 may have undulations or curves 2502 to force the air to flow over a larger area before exiting the mask system. This will slow the flow of the air producing low velocity, fully developed, laminar flow.

In one form, the baffle may form a part of the elbow. However, the baffle may be a separate part that may be retrofitted to an elbow. If retrofitted, the baffle may be held in place by any suitable means, e.g., interference fit, push fit, adhesive, etc. In the case where the baffle is to be interference or push fit into the elbow, a lip may be provided to the baffle to enhance sealing.

In another embodiment, as shown in FIGS. 5-3-1 and 5-3-2 and schematically shown in FIG. 5-4, the baffle may be attached by a bayonet connection. In the illustrated embodiment, the baffle 2500 includes an annular side wall 2510 with one or more male connectors 2512 provided to an exterior surface of the annular side wall 2510. The elbow 2540 includes an annular side wall 2542 with a corresponding number of female connectors 2544 (i.e., L-shaped female connectors) provided to an interior surface of the annular side wall 2542. In use, the male connectors 2512 are received in the first leg 2544(1) of respective female connectors 2544, and then the baffle 2500 and elbow 2540 are rotated relative to one another to slide the male connectors 2512 into the second leg 2544(2) of respective female connectors 2544.

However, it should be appreciated that other suitable arrangements of the bayonet connection may be provided. For example, the baffle may include female connectors for attachment with male connectors on the elbow. Also, the bayonet connection may be positioned on the annular side walls of the baffle and elbow (as shown in FIGS. 5-3-1, 5-3-2, and 5-4), or the bayonet connection may be positioned on the mating surfaces of the baffle and elbow (e.g., see FIG. 5-5).

In the illustrated embodiment, the elbow 2540 includes multiple vent holes 2545 arranged on an annular side wall so that the elbow 2540 and baffle 2550 are arranged to force washout gas generally parallel to the user's face in use. Typically vents are positioned so that vent flow from the mask system is perpendicular to the user's face and may possibly jet vent flow onto the bed partner or other interferences such as bedding. Jetting increases noise and discomfort for the bed partner. Vented gas traveling parallel to the user's face tends to avoid these problems by "spreading" the vent flow radially over a larger area rather than concentrating it all in a small region. That is, the vent flow in this arrangement is akin to a distributed load rather than a concentrated load, should it meet with an obstruction in its path.

In one form, the air path 2560 created by the elbow and the baffle will be about 0.01 to 5 mm, e.g., 1 mm.

In another form, the baffle 2500 may not be anchored in one position. For example, the baffle 2500 may be able to rotate within the elbow 2540.

In another form, a series of baffles could be used to force air flow out of multiple air paths. For example, 2, 3, 4, or more baffles may be stacked and placed between the elbow and the mask.

In one form, the baffle may be about 1-30 mm wide (radially), e.g., 10 mm wide (radially).

In an embodiment, the baffle may be constructed of a hard plastic, e.g., such as polycarbonate. Alternatively, the baffle may be constructed from softer materials to absorb more of the sound, e.g., low durometer silicone. However, other suitable materials are possible.

Figures 2, 3, 4, 5, 6:
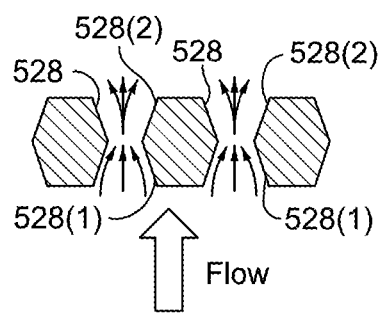

In an alternative embodiment, as shown in FIGS. 5-6-1 and 5-6-2, a single baffle may be used that is coiled to form multiple air paths. FIG. 5-6-1 shows the coil-type baffle 2600 in its uncoiled or uncompressed position, and FIG. 5-6-2 shows the coil-type baffle 2600 in its coiled or compressed position between a mask 2620 and elbow 2640. As illustrated, the coils cooperate to form multiple air paths along its length. In an embodiment, one or more grooves may be provided in each coil to define air paths across the coil. Such arrangement provides a "stack" of vent rings integrally formed as a one-piece structure.

4.2.2 Tracks or Guides

In an embodiment, tracks or guides may be provided to a vent hole that are structured to force washout gas to flow in long, narrow passages as it exits the mask system.

For example, FIGS. 5-7-1 and 5-7-2 illustrate an elbow 2740 including multiple vent holes 2745 and spaced-apart raised tracks 2747 proximate each vent hole 2745 along the inner surface of the elbow 2740 (i.e., the side of the elbow that is subjected to the pressurized air flow). In the illustrated embodiment, the tracks 2747 are generally rectangular. However, the tracks may have other suitable shapes to direct washout gas, e.g., elliptical. In an embodiment, the "track" arrangement may also incorporate the use of an annular baffle as shown in FIGS. 5-3-1 and 5-3-2.

In an alternative embodiment, the tracks may extend into the inner surface of the elbow 2740. In such embodiment, the tracks would resemble indents or recesses. In use, the indented tracks will draw air flow into them and create a long, narrow flow path.

In another form, the tracks may be uniform in length. Alternatively, the tracks may vary in length. In an embodiment, the tracks will be longer than about 2 mm, e.g., 4 mm.

In an embodiment, each vent hole 2745 will have one or more tracks leading to the opening of the hole, e.g., two tracks per vent hole as shown in FIG. 5-7-2. If there is more than one track for each vent hole, the track may be separated by any suitable amount, e.g., more than about 0.1 mm.

In an embodiment, the tracks may be molded or otherwise formed into the elbow. Alternatively, the tracks may be provided in a separate component (e.g., molded into separate component) and retrofitted to the elbow.

In another embodiment, two or more tracks may join together or otherwise cooperate about a vent hole to form a tube (or at least a portion of a tube). This tube may have a circular cross section, or any other desired cross section, e.g., square. Similar to the tracks, the tube will direct air flow down a long, narrow pathway to form low velocity, fully developed, laminar flow.

4.2.3 Baffle with Tracks or Guides

In an embodiment, a baffle with tracks may be provided to an elbow.

For example, FIG. 5-8-1 illustrates a baffle 2800 including a plurality of tracks 2802. As illustrated, the baffle 2800 includes a ring-like structure with each track 2802 extending from an inner radius of the baffle to an outer radius of the baffle.

In the illustrated embodiment, groups of tracks 2802 are placed about the baffle. However, the tracks may be arranged in other suitable manners, e.g., continuous around the baffle, randomly arranged.

In the illustrated embodiment, each track 2802 extends into the surface of the baffle like an indent or recess. Alternatively, each track may be raised from the surface of the baffle.

In the illustrated embodiment, each track 2802 may be curved from the inner radius of the baffle to the outer radius of the baffle. This arrangement maximizes the length of the tracks so that the air travels a longer distance and loses velocity. However, each track may have other suitable shape along its length, e.g., straight line or coiled extending from the inner radius to the outer radius of the baffle.

As shown in FIGS. 5-8-1 and 5-8-2, the tracks 2802 are provided to one side of the baffle 2800. However, the tracks 2802 may be provided to both sides of the baffle (e.g., see FIG. 5-8-3).

FIGS. 5-8-2 and 5-8-3 show the baffle 2800 provided to an elbow 2840. As illustrated, the elbow 2840 includes one or more windows 2870 about its circumference adapted to receive the baffle 2800. Specifically, the baffle 2800 extends through the windows 2870 and includes cutouts 2804 to receive elbow wall portions 2872 adjacent the windows 2870. Also, the baffle 2800 is open ended (e.g., C-shaped) to allow the baffle 2800 to deform slightly during assembly/disassembly to the elbow 2840, e.g., spring like a circlip.

In an embodiment, the baffle 2800 with tracks on one side may reduce noise from the vent by at least 10 dBA when compared to other conventional masks (e.g., ResMed's Mirage Micro). In terms of human hearing, a 10 dBA reduction in noise corresponds to half the amount of noise previously emitted. A vent cap (as described above in section 4.1) may reduce noise from the vent by at least 3 dBA when compared to other conventional masks. A 5 dBA reduction in noise is clearly noticeable when compared to the noise previously emitted. A 3 dBA reduction in noise is just noticeable when compared to the noise previously emitted. Therefore, the baffle is highly effective in terms of maximizing noise reduction from the vent and diffusing air flow from the vent.

FIGS. 5-9-1 to 5-9-6 illustrate a baffle or vent ring 3100 for an elbow 3140 according to another embodiment of the present invention. As illustrated, the vent ring 3100 has an open-ended C-shaped main body 3101 with L-shaped finger tabs 3103 adjacent the open end (see FIG. 5-9-2). The main body 3101 includes a plurality of radially arched tracks or grooves 3102 on one or both sides thereof. The grooves 3102 extend from an inner radius of the vent ring to an outer radius of the vent ring.

In the illustrated embodiment, each groove is open-ended (e.g., U-shaped, V-shaped, semi-circular shaped, etc.) and tapers along its length from the inner radius to the outer radius of the vent ring. In addition, each groove may be radially arched or curved along its length. However, it should be appreciated that each groove may include other suitable arrangements, e.g., same width along its length, zig-zag or other tortuous path along its length, different size, different depth, extend at different angle along main body (e.g., longest path from inner radius to outer radius of vent ring), etc.

Similar to the baffle 2800 described above, the vent ring 3100 is deformable (e.g., like a c-clip or circlip) to assemble/disassemble to the elbow 3140. As best shown in FIG. 5-9-4, the elbow 3140 includes a slot 3142 adapted to receive and support the vent ring 3100 within the elbow 3140. Specifically, the slot 3142 provides an entry/exit window 3143 to receive the vent ring 3100, upper and lower flanges 3144, 3145 to support the vent ring 3100 within the elbow, and windows 3146 along with entry/exit window 3143 that allow gas washout across the vent ring 3100, and supporting beams 3148 to maintain and align the vent ring 3100 within the elbow 3140.

To assemble the vent ring 3100 to the elbow 3140, the user's fingers may be placed in the gaps defined by the finger tabs 3103 of the vent ring 3100 so as facilitate gripping and squeezing the finger tabs 3103 towards one another, which distorts or deforms the generally round vent ring into an oval shape (see FIG. 5-9-3). Since the width of the distorted vent ring 3100 is now less than a width of the entry/exit window 3143 of the elbow 3140, the vent ring 3100 may be slid through the entry/exit window 3143 and into the elbow 3140 (see FIG. 5-9-4). When the finger tabs 3103 are released, the vent ring 3100 resiliently springs back into shape. The vent ring 3100 is held in place by an interference fit, where the width of the vent ring 3100 is substantially the same as that of the entry/exit window 3143. In addition, the vent ring 3100 includes cutouts 3104 to receive supporting beams 3148 of the elbow 3140 (see FIGS. 5-9-1 and 5-9-5).

Due to forces applied to the vent ring 3100 for insertion and removal from the elbow 3140, the vent ring 3100 may be made from a substantially rigid or semi-rigid material. Also, the elbow 3140 provides flanges 3144, 3145 on opposing sides of the vent ring 3100 to support the vent ring 3100 when it is loaded (e.g., pressurized gas flow), thereby preventing bowing of the vent ring 3100 and thus leak (see FIG. 5-9-6).

In use, the grooved vent ring combines with the elbow to define vent orifices, i.e., each vent orifice defined by a part of the vent ring (the groove) and a part of the elbow (upper and/or lower flange). Thus, vented gas escapes along the one or more tracks or grooves between an outer surface of the elbow and the vent ring.

FIGS. 5-10-1 to 5-10-3 illustrate a vent ring 3200 according to another embodiment of the present invention. In this embodiment, the vent ring 3200 includes a hinge or movable joint 3290 and a locking mechanism 3292 diametrically opposed from the hinge 3290. When the locking mechanism 3292 is unlocked, the hinge 3290 allows the vent ring 3200 to pivot open and be wrapped around the slot 3142 in the elbow 3140 (see FIG. 5-10-2). In the illustrated embodiment, the locking mechanism 3292 includes a pin and groove arrangement wherein the pin 3292(1) and groove 3292(2) can be pushed together and interlocked (see FIG. 5-10-1) to close the arms of the vent ring 3200 around the slot. The groove 3292(2) may be provided to a finger tab 3293 with an arched protrusion 3294 to facilitate grip. Also, as illustrated, the hinge 3290 is provided by a thinned region of the vent ring 3200 (e.g., cutout 3204 and slot 3291). The vent ring 3200 should be somewhat flexible to allow the vent ring 3200 to be deformed (hoop stress) into an unlocked or open position for assembly to the elbow 3140.

Similar to the above, the vent ring 3200 includes a plurality of radially arched tracks or grooves 3202 on one or both sides thereof. When grooves 3202 are provided on both sides, it is preferable to have the grooves 3202 extending in opposite directions on opposing top and bottom sides so that air streams are exhausted in opposite directions (see FIG. 5-10-3), which provides more diffuse exhaust.

FIGS. 5-11-1 and 5-11-2 illustrate a vent ring 3300 and elbow 3340 according to another embodiment of the present invention. In this embodiment, the vent ring 3300 is soft and flexible and includes a closed, o-ring shape so that the vent ring 3300 can be stretched or wrapped around the elbow 3340. A finger tab 3303 is provided to the vent ring 3300 to facilitate assembly/disassembly to the elbow 3340.

The elbow 3340 includes a slot 3342 around its perimeter to receive the vent ring 3300. The bottom wall of the slot 3342 includes openings 3346 for gas washout and each side wall of the slot 3342 (adjacent each opening 3346) includes a plurality of tracks or grooves 3302. Thus, no grooves are provided on the vent ring 3300, rather the grooves 3302 are provided on the elbow 3340. In use, the vent ring 3300 forms a seal with the elbow 3340 so that air can only exhaust between the vent ring 3300 and the grooves 3302 on the elbow 3340. Also, the soft and flexible vent ring 3300 may dampen sound in use.

FIGS. 5-12-1 and 5-12-2 illustrate a vent ring 3400 and elbow 3440 according to another embodiment of the present invention. This embodiment is similar to the embodiment of FIGS. 5-11-1 and 5-11-2; in contrast, grooves 3402 are provided on the vent ring 3400, and no grooves are provided on the elbow 3440 (e.g. smooth surface on side walls of the slot 3442). The bottom wall of the slot 3442 includes openings 3446 for gas washout. This arrangement may be easier to manufacture.

As illustrated, the vent ring 3400 includes a plurality of tracks or grooves 3402 along the entire perimeter of the vent ring 3400. This arrangement provides 360° vent flow which may provide more diffuse exhaust. In an embodiment, a section of the vent ring 3400 may not have grooves, and this section could be aligned with the patient's eyes so that air flow does not irritate the patient's eyes in use.

5. One-Piece Elbow with Integral Diffused Vent Cap

Figures 1, 2, 3, 4, 5, 6, 7:
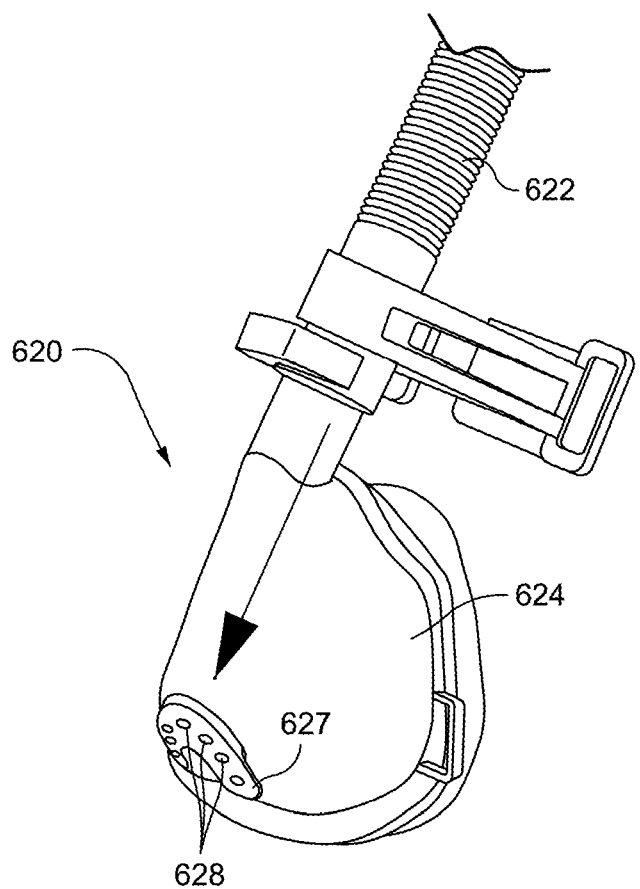
Figures 2, 3, 4, 5, 6, 7:
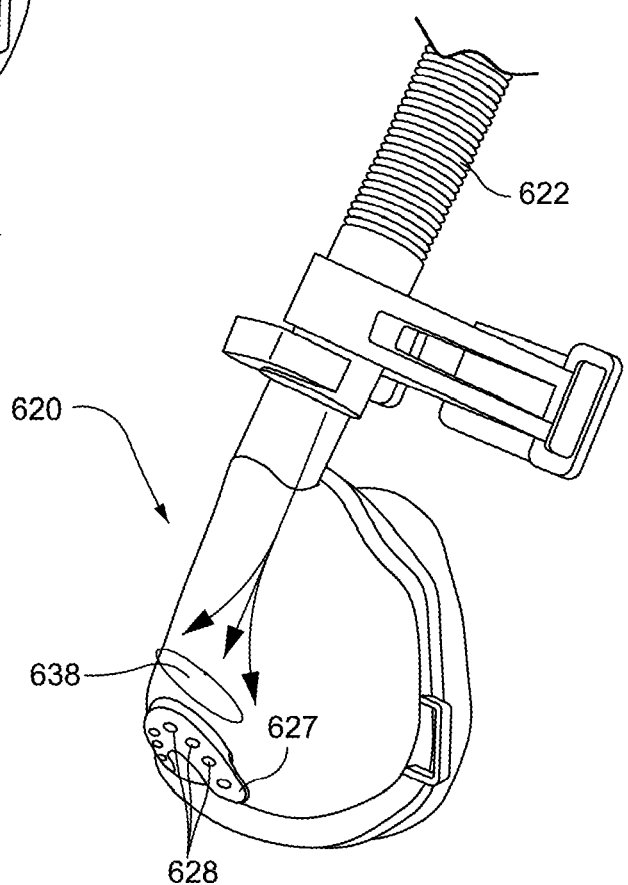

FIGS. 6-1 to 6-7 illustrate an elbow 3040 including a vent arrangement according to another embodiment of the present invention. In this embodiment, the vent arrangement is in the form of a diffused vent cap 3000 that is integrally formed in one-piece with the elbow 3040. This arrangement provides a single piece elbow with no removable parts, e.g., so patients do not have to disassemble the elbow for cleaning. In alternative embodiments, the vent cap may be integrally formed in one piece with other portions of the mask, e.g., mask frame, associated conduit, etc.

As illustrated, the elbow 3040 includes a first end 3040(1) for releasably engaging with an opening in a mask frame and a second end 3040(2) for releasably engaging with a swivel. In the illustrated embodiment, the first end 3040(1) includes opposing ribs 3046 adapted to engage the mask frame with a snap-fit. The first end 3040(1) may also have a long sealing surface 3041 adapted to interface with the mask frame, whereby such a long sealing surface promotes better sealing thereby reducing leak between the elbow and mask frame. Also, the sealing surface 3041 may be frosted or textured to prevent noise (for example squeak) created by the friction of two moving parts. The first end 3040(1) may also have a stepped arrangement whereby sealing surface 3041 is wider than stepped surface 3042. This may allow for easier disassembly of the elbow from the mask frame. Additionally, scallops or cut outs 3043 may be provided to stepped surface 3042 to allow the stepped surface 3042 to flex inwards thereby enabling disassembly of the elbow from the mask frame. The second end 3040(2) includes a plurality of resilient flexible arms 3047 adapted to engage the swivel with a snap-fit. However, the first and second ends 3040(1), 3040(2) may include other suitable structures for engaging the frame/swivel.

The main body of the elbow 3040 includes a vent cap 3000 integrally formed in one-piece therewith. Similar to the vent cap 2300 described above, the vent cap 3000 includes a base wall 3035, a dome 3045 extending upwardly from the base wall 3035, and multiple vent holes 3030 arranged on an annular side wall of the dome 3045 to provide diffuse airflow that is directed away from the patient's face as well as the bed partner. The angle of the diffused airflow can be tuned by altering the dimensions of the vent cap. The diffused airflow provides venting over a larger area to avoid jetting and may also reduce noise.

As shown in FIGS. 6-2 and 6-4, the elbow 3040 includes a baffle 3052 adjacent to where the elbow 3040 is attached to the mask frame. The baffle 3052 has a generally U-shape and is arranged to divide the upper arm of the elbow into an air delivery passage and an exhaust passage, e.g., to enhance $CO_2$ washout. In the illustrated embodiment, the baffle 3052 is integrally formed with the elbow 3040. However, in an alternative embodiment, the baffle may be retrofit to the elbow. Gaps 3053 are provided on either side of the baffle 3052 from the inner surfaces of first end 3040(1) to allow stepped surface 3042 to freely flex inwards when assembled and disassembled to the mask frame.

6. Plug Type Vent

FIGS. 7-1 to 7-3 illustrate a plug-type vent 3500 and frame 3540 according to another embodiment of the present invention. In this embodiment, the plug 3500 is soft and flexible and includes a relatively long and narrow shape (e.g., I-shaped) for insertion into a corresponding I-shaped slot 3542 in the frame 3540.

As illustrated, the plug 3500 includes a base 3501 and a top lip 3503 extending from the base 3501. A plurality of tracks or grooves 3502 are provided along the exterior surface of the base 3501 and the lower surface of the lip 3503. The bottom wall of the slot 3542 includes an elongated opening 3546 for gas washout. In use, the grooved plug 3500 forms a seal with the slot 3542 so that air can only exhaust between the slot walls and the grooves 3502 on the plug 3500. Also, the soft and flexible plug 3500 facilitates attachment to the frame 3540 and may dampen sound in use.

In the illustrated embodiment, the grooves 3502 extend along the entire perimeter of the plug, e.g., 360° vent flow, which may allow vent flow to be directed into the patient's eyes. In an alternative embodiment, the grooves may exit the plug vertically rather than horizontally so as to direct air flow away from the patient's eyes.

Figures 2, 3, 4, 5, 6, 7, 8, 9, 10, 11:
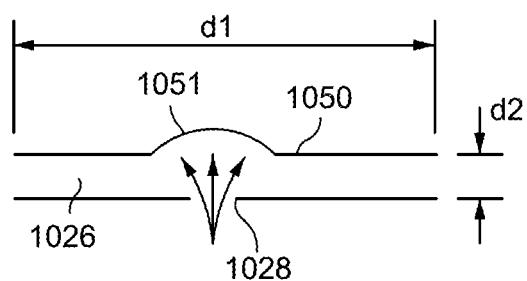
Figures 2, 3, 4, 5, 6, 7, 8, 9, 10, 11, 12:
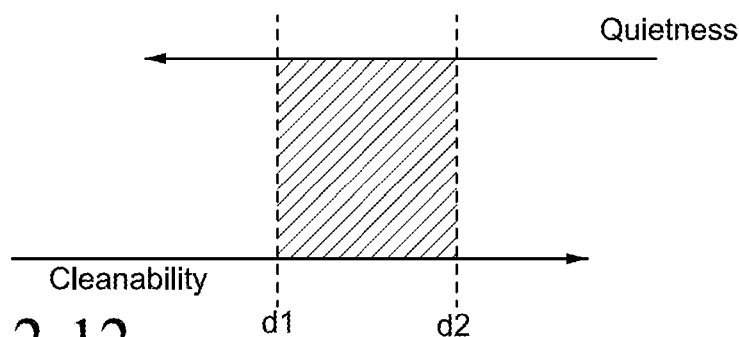
Figures 1, 2, 3, 4, 5, 6, 7, 8, 9, 10, 11, 12, 13:
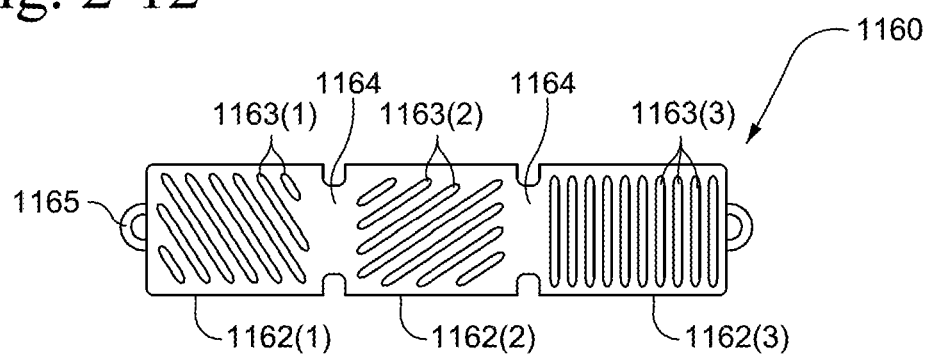
Figures 2, 3, 4, 5, 6, 7, 8, 9, 10, 11, 12, 13:
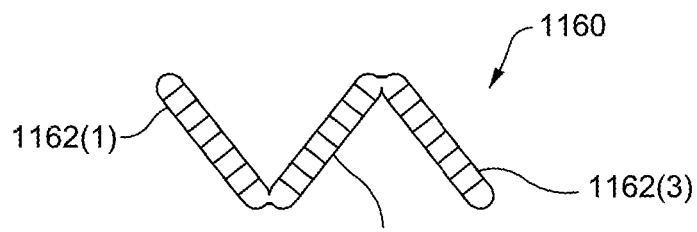
Figures 2, 3, 4, 5, 6, 7, 8, 9, 10, 11, 12, 13:
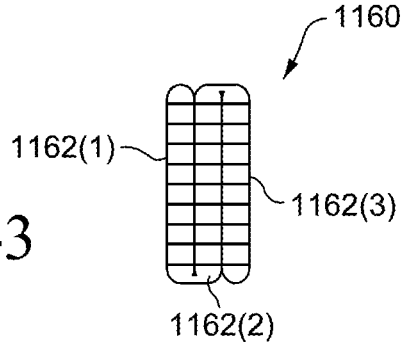
Figures 1, 2, 3, 4, 5, 6, 7, 8, 9, 10, 11, 12, 13, 14:
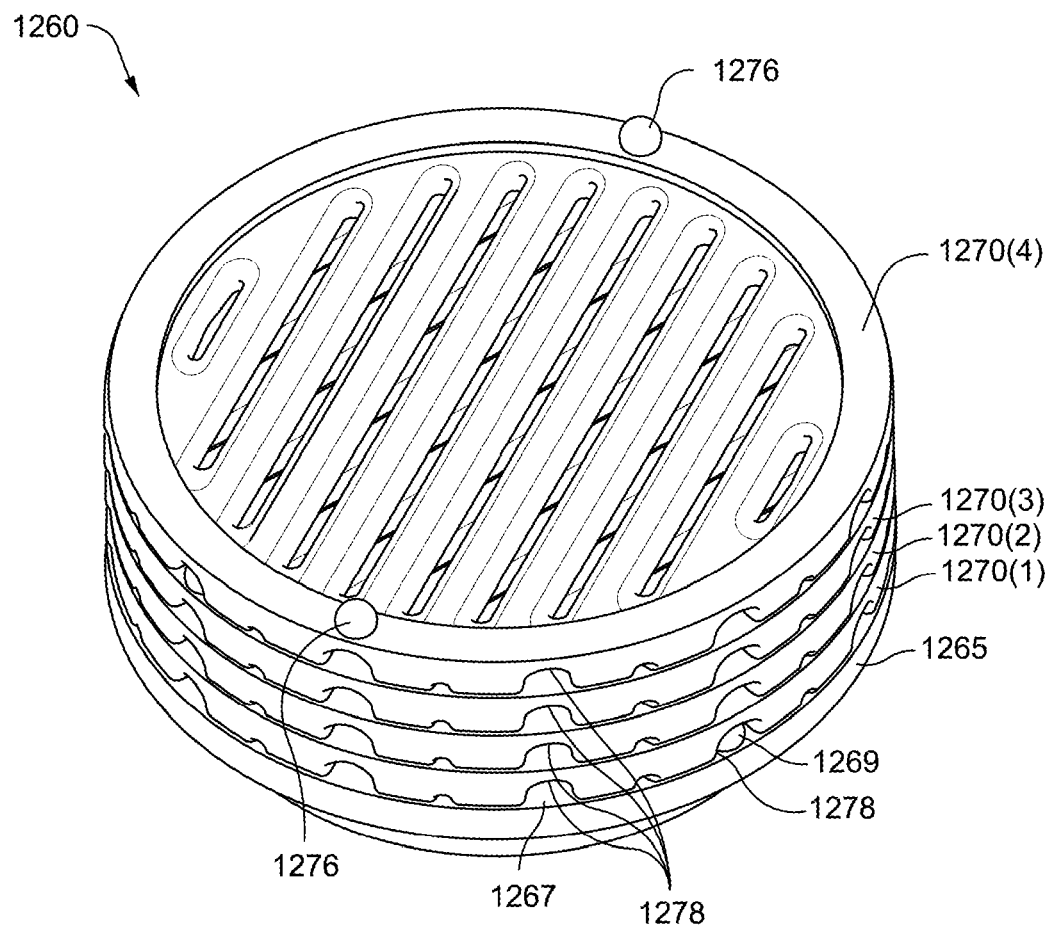
Figures 2, 3, 4, 5, 6, 7, 8, 9, 10, 11, 12, 13, 14:
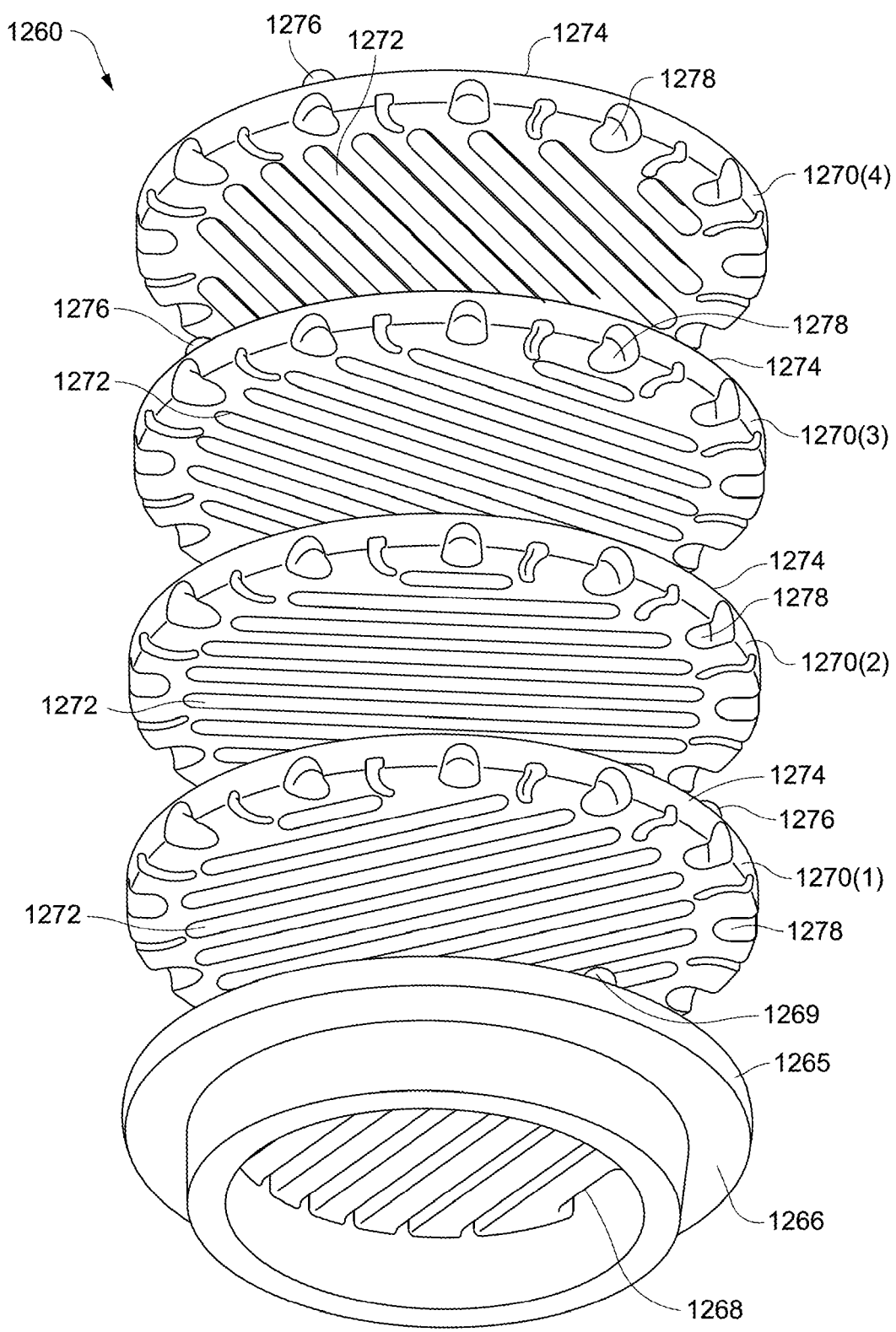
Figures 2, 3, 4, 5, 6, 7, 8, 9, 10, 11, 12, 13, 14:
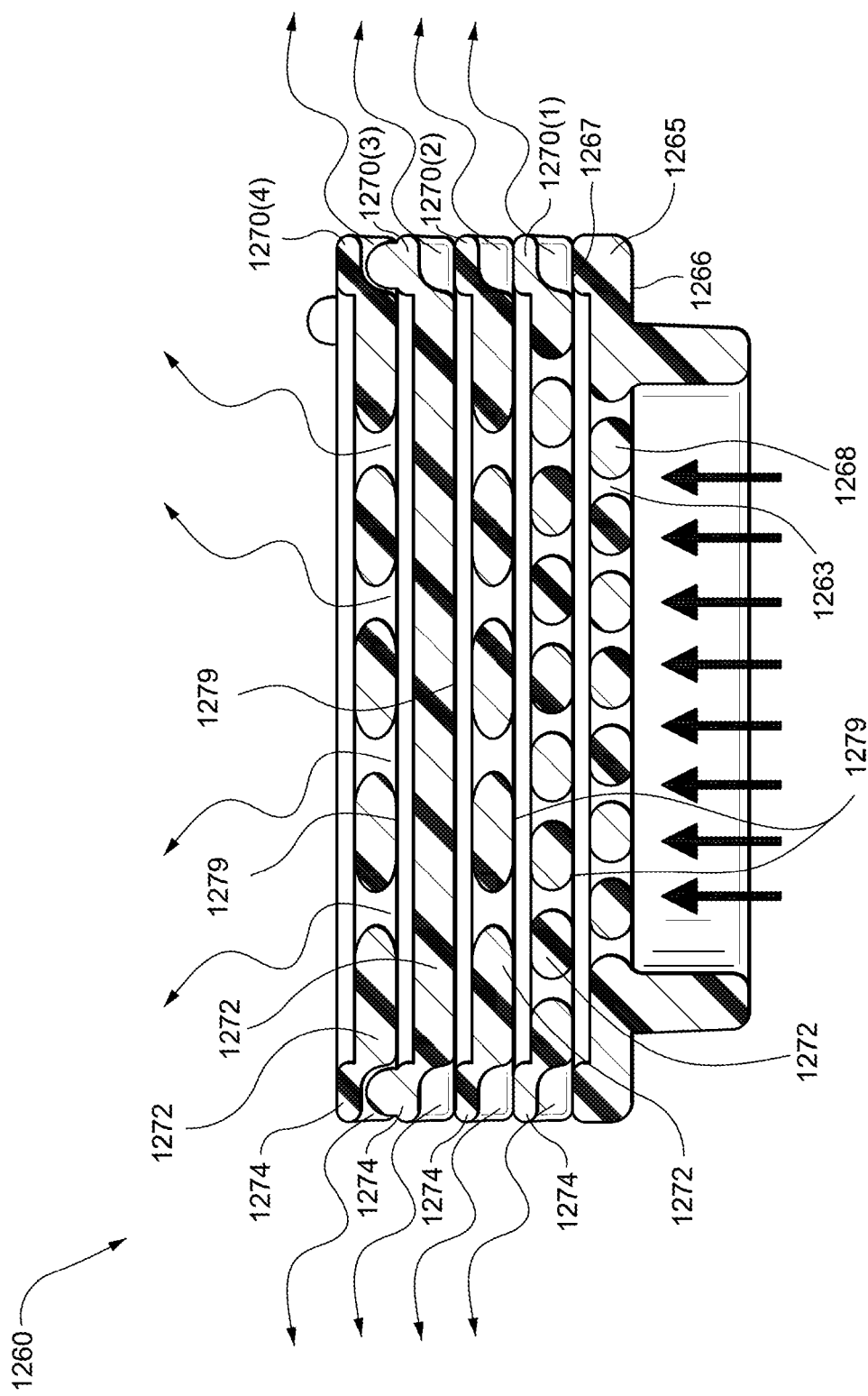
Figures 1, 2, 3, 4, 5, 6, 7, 8, 9, 10, 11, 12, 13, 14, 15:
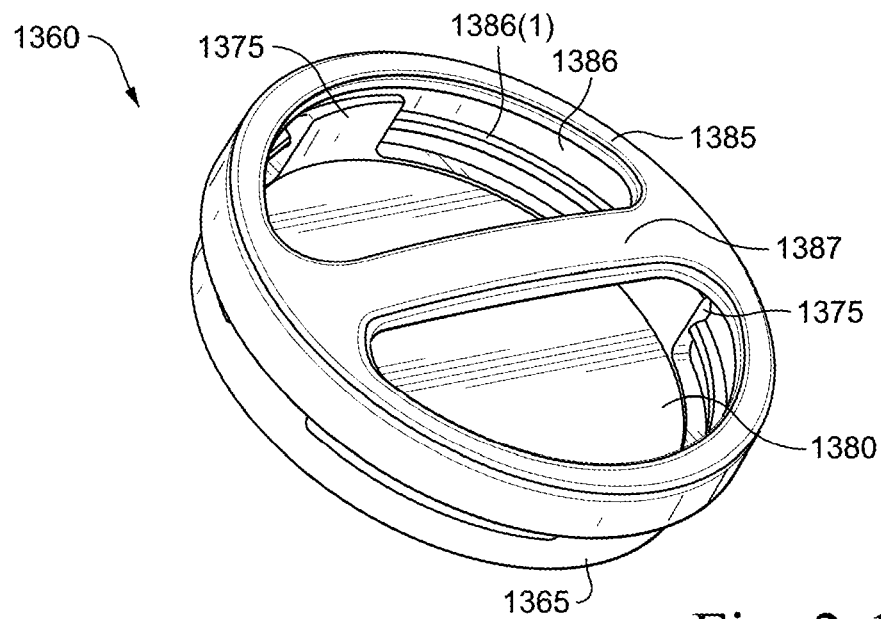
Figures 2, 3, 4, 5, 6, 7, 8, 9, 10, 11, 12, 13, 14, 15:
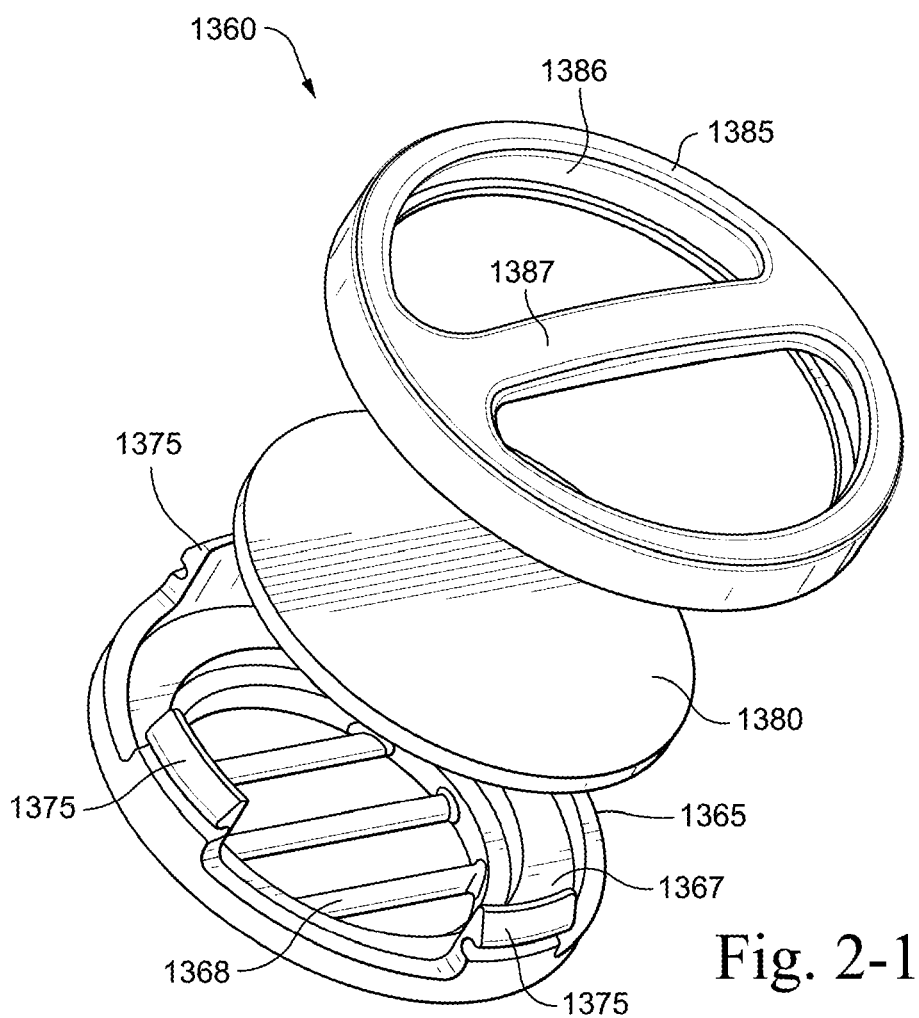
Figures 2, 3, 4, 5, 6, 7, 8, 9, 10, 11, 12, 13, 14, 15:
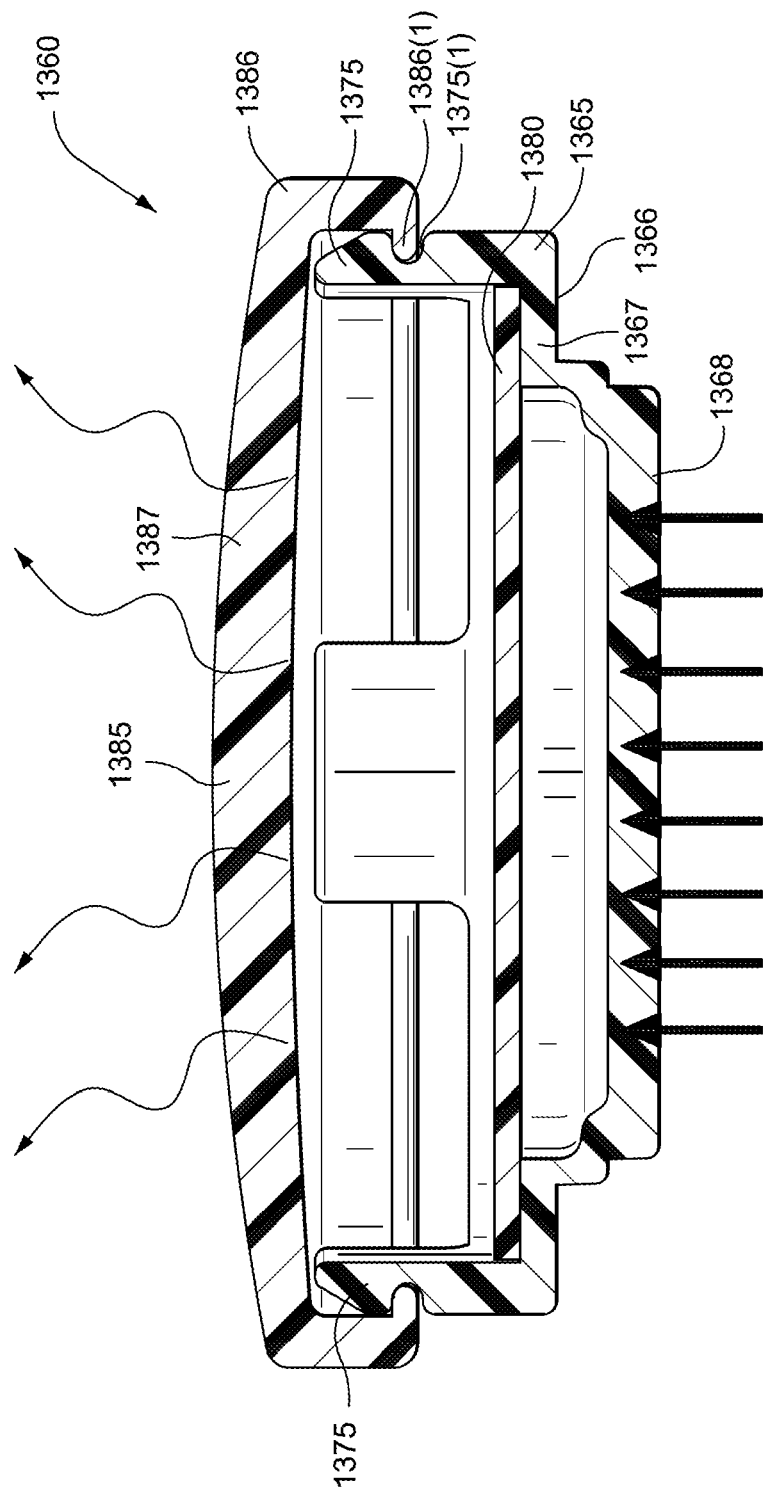
Figures 1, 2, 3, 4, 5, 6, 7, 8, 9, 10, 11, 12, 13, 14, 15, 16:
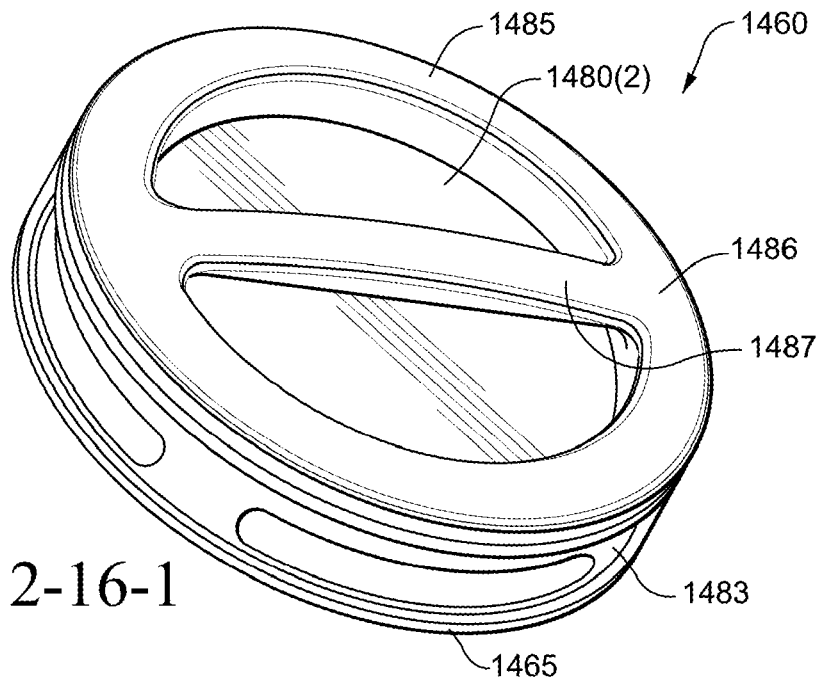
Figures 2, 3, 4, 5, 6, 7, 8, 9, 10, 11, 12, 13, 14, 15, 16:
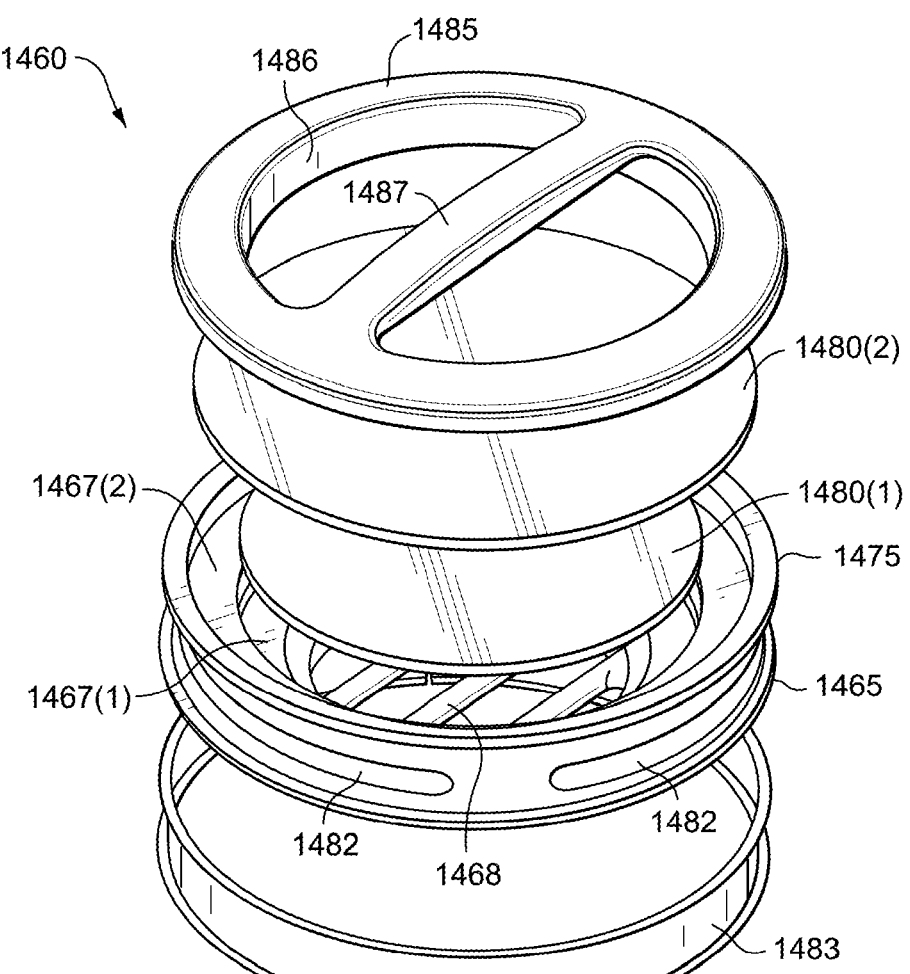
Figures 2, 3, 4, 5, 6, 7, 8, 9, 10, 11, 12, 13, 14, 15, 16:
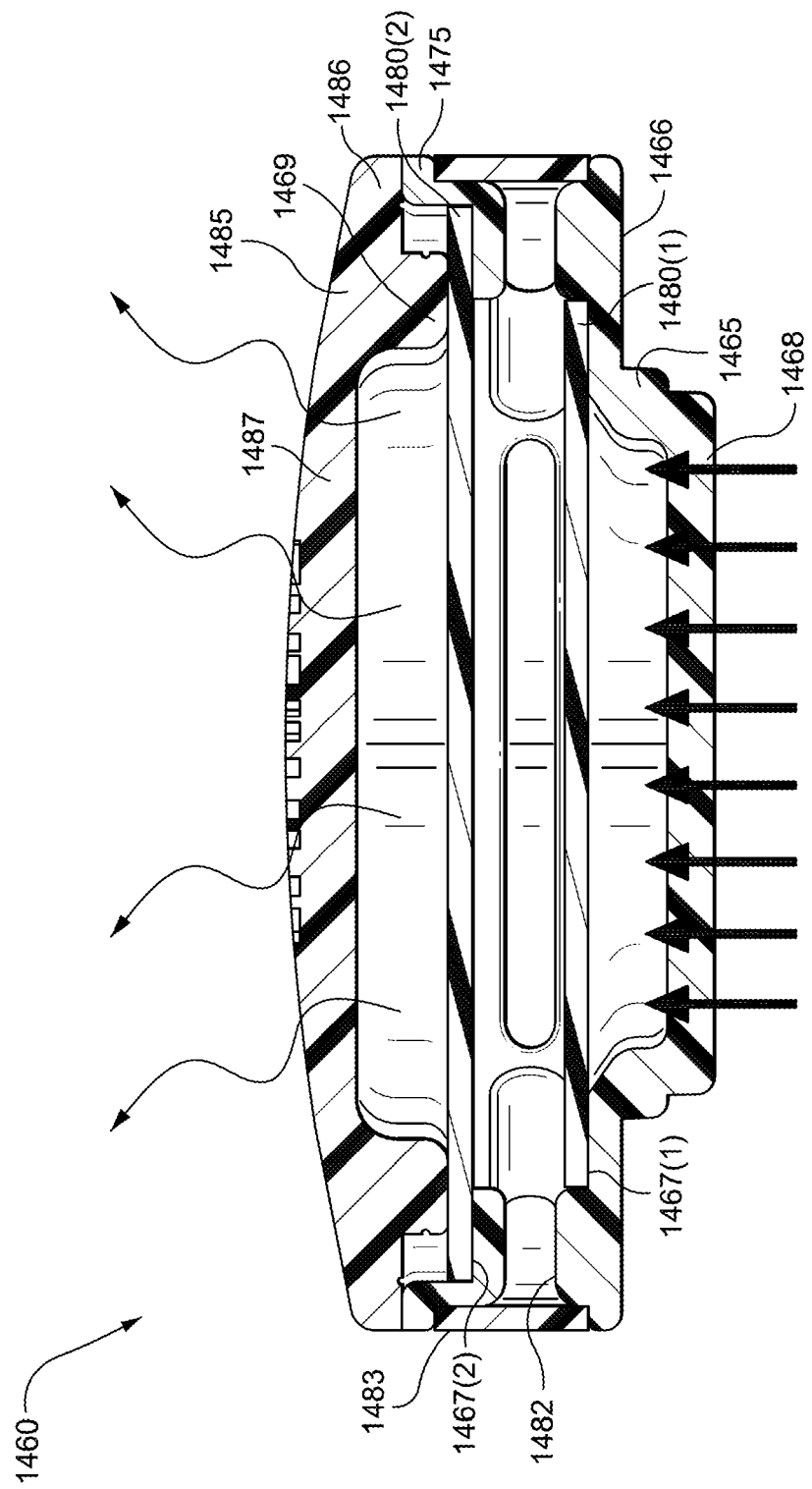
Figures 1, 2, 3, 4, 5, 6, 7, 8, 9, 10, 11, 12, 13, 14, 15, 16, 17:
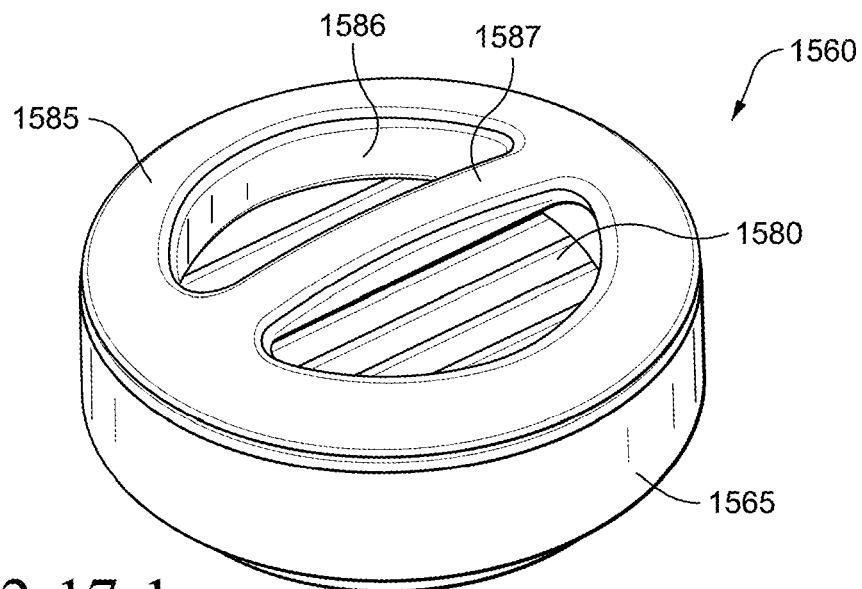
Figures 2, 3, 4, 5, 6, 7, 8, 9, 10, 11, 12, 13, 14, 15, 16, 17:
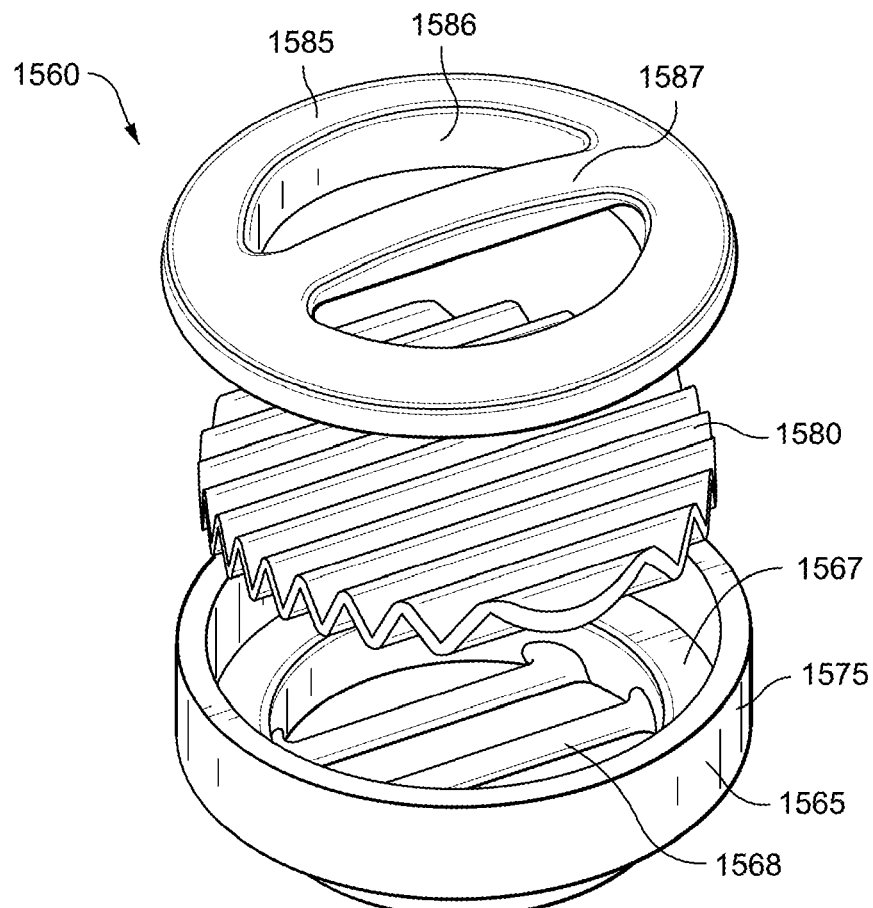
Figures 1, 2, 3, 4, 5, 6, 7, 8, 9, 10, 11, 12, 13, 14, 15, 16, 17, 18:
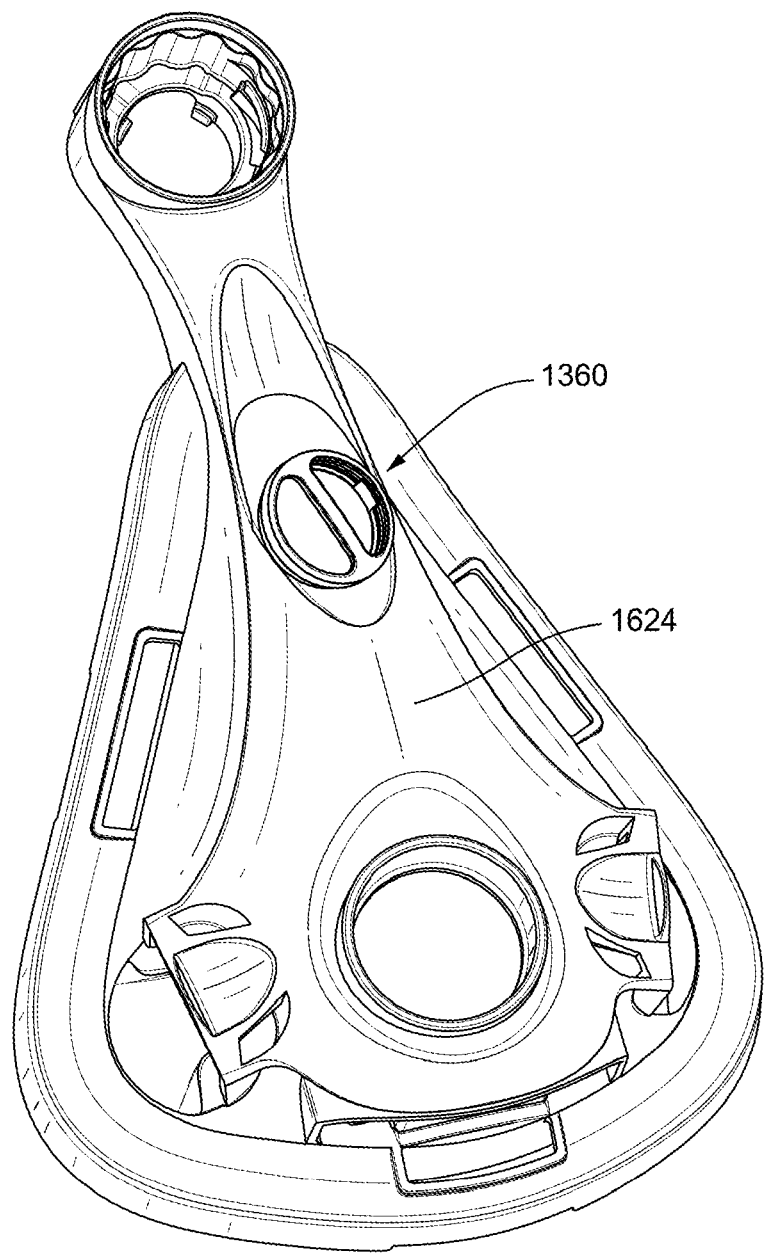
Figures 2, 3, 4, 5, 6, 7, 8, 9, 10, 11, 12, 13, 14, 15, 16, 17, 18:
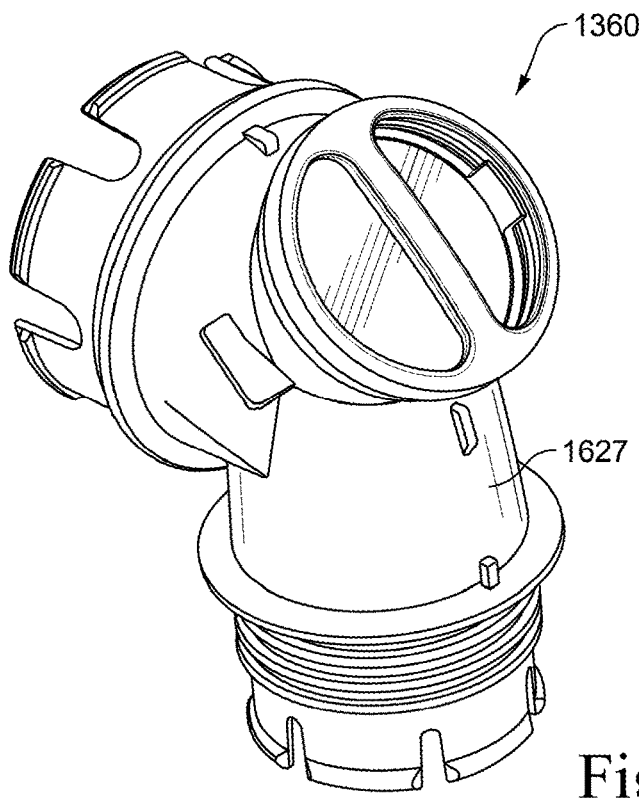
Figures 2, 3, 4, 5, 6, 7, 8, 9, 10, 11, 12, 13, 14, 15, 16, 17, 18:
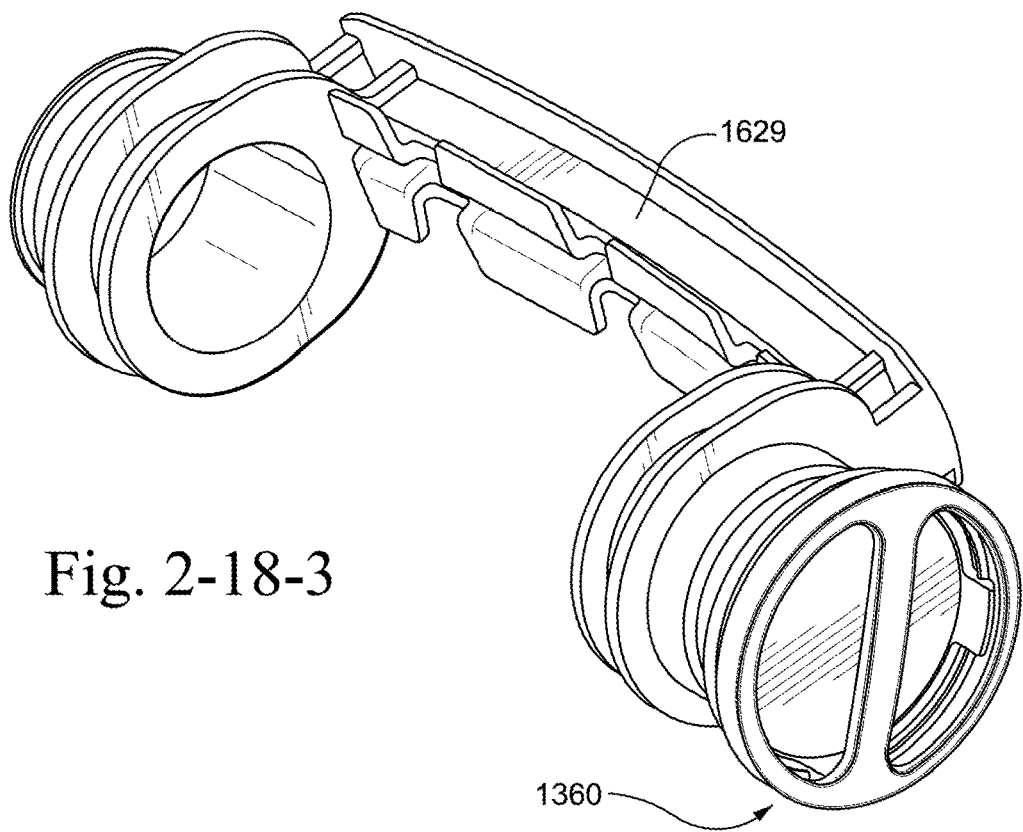
Figures 2, 3, 4, 5, 6, 7, 8, 9, 10, 11, 12, 13, 14, 15, 16, 17, 18, 19:
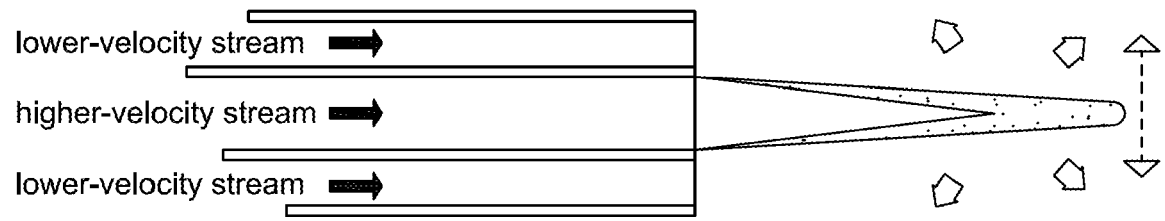
Figures 2, 3, 4, 5, 6, 7, 8, 9, 10, 11, 12, 13, 14, 15, 16, 17, 18, 19, 20:
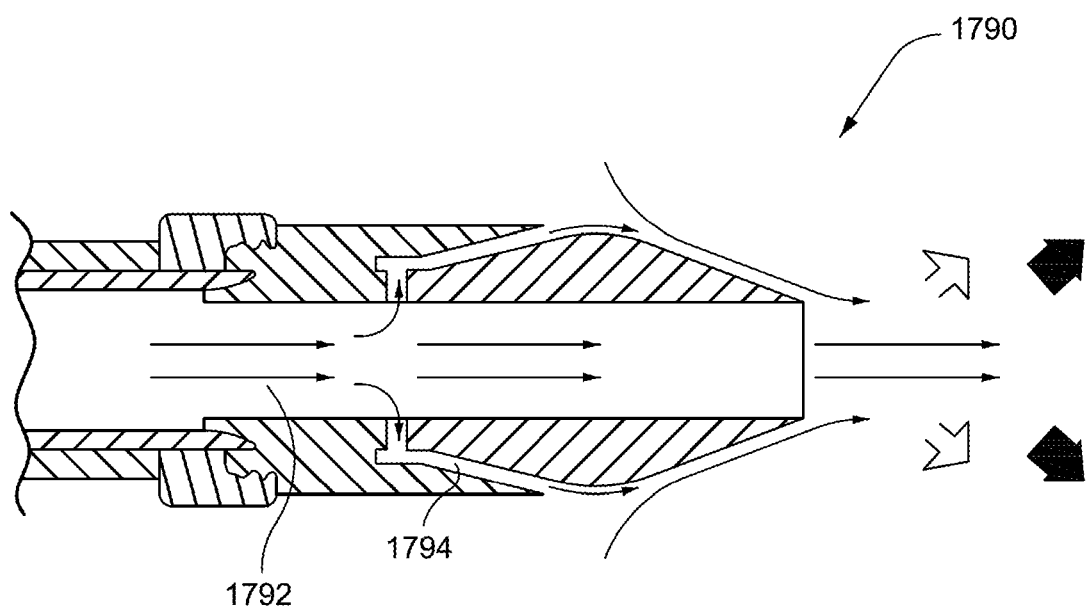
Figures 1, 2, 3, 4, 5, 6, 7, 8, 9, 10, 11, 12, 13, 14, 15, 16, 17, 18, 19, 20, 21:
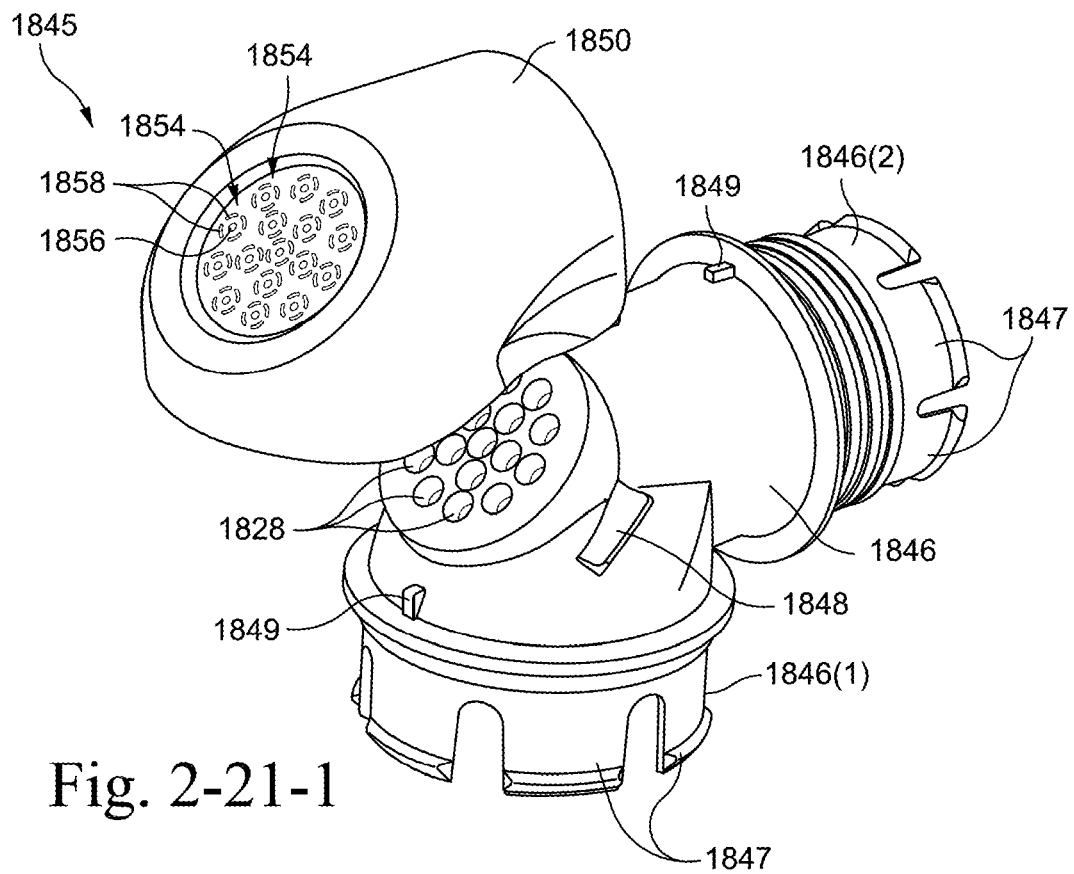
Figures 2, 3, 4, 5, 6, 7, 8, 9, 10, 11, 12, 13, 14, 15, 16, 17, 18, 19, 20, 21:
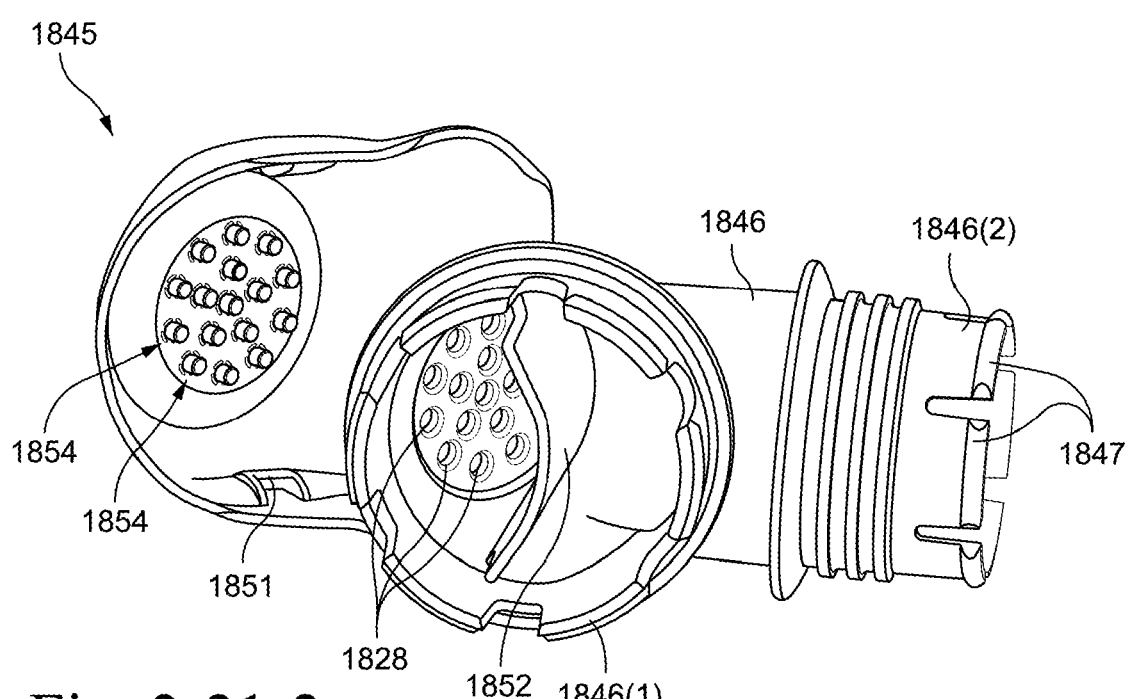
Figures 2, 3, 4, 5, 6, 7, 8, 9, 10, 11, 12, 13, 14, 15, 16, 17, 18, 19, 20, 21:
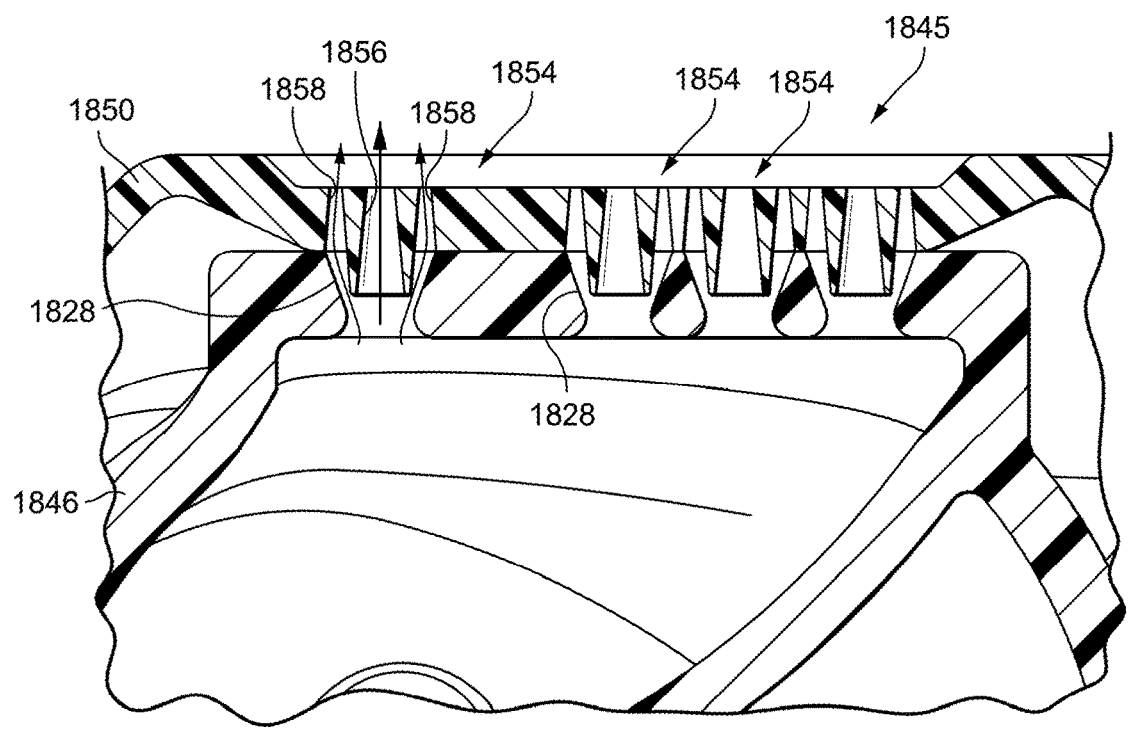
Figures 2, 3, 4, 5, 6, 7, 8, 9, 10, 11, 12, 13, 14, 15, 16, 17, 18, 19, 20, 21:
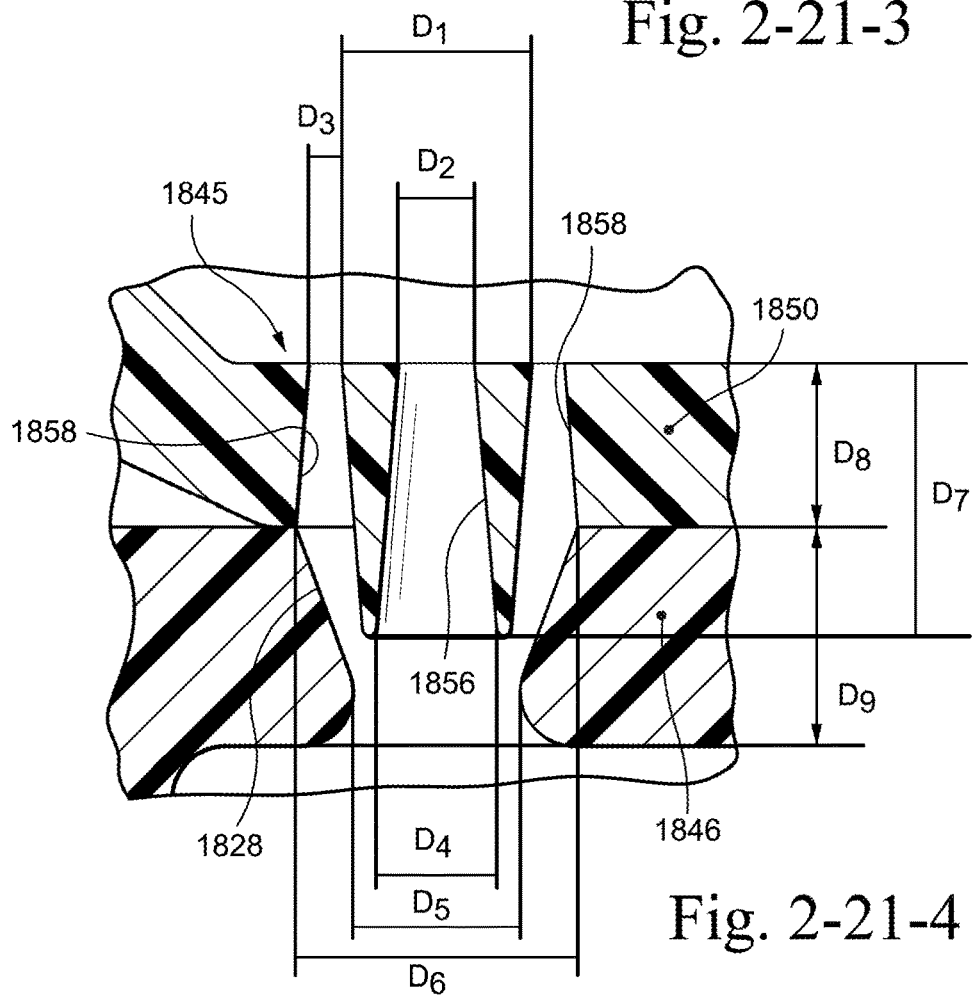
Figures 1, 2, 3, 4, 5, 6, 7, 8, 9, 10, 11, 12, 13, 14, 15, 16, 17, 18, 19, 20, 21, 22:
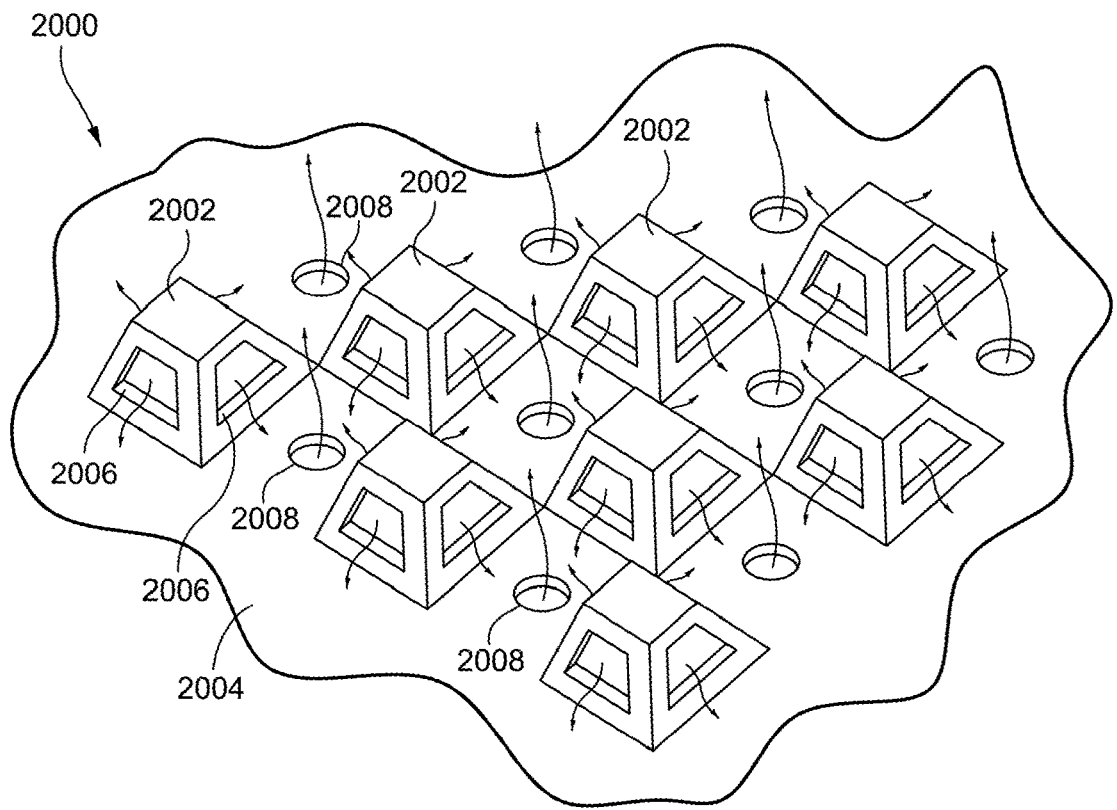
Figures 2, 3, 4, 5, 6, 7, 8, 9, 10, 11, 12, 13, 14, 15, 16, 17, 18, 19, 20, 21, 22:
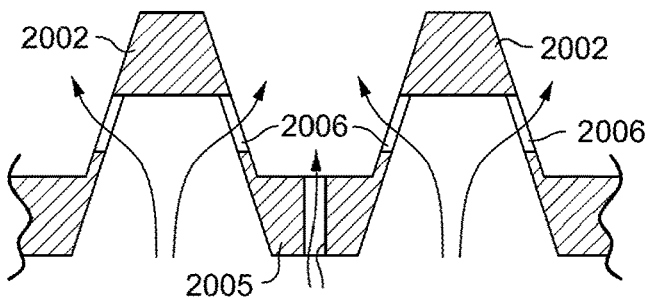
Figures 2, 3, 4, 5, 6, 7, 8, 9, 10, 11, 12, 13, 14, 15, 16, 17, 18, 19, 20, 21, 22:
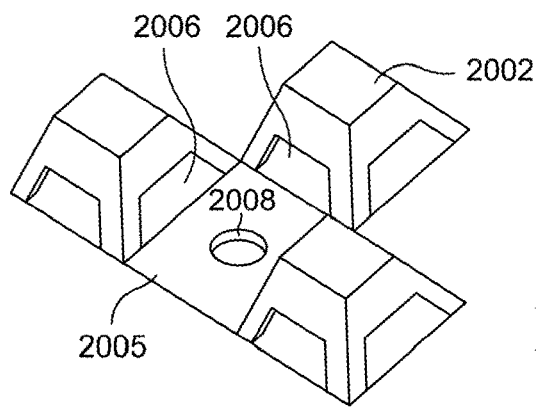
Figures 2, 3, 4, 5, 6, 7, 8, 9, 10, 11, 12, 13, 14, 15, 16, 17, 18, 19, 20, 21, 22:
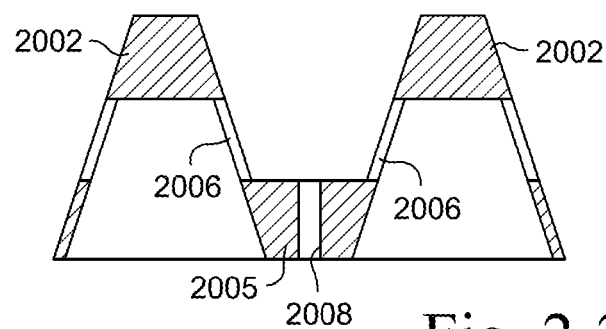
Figures 2, 3, 4, 5, 6, 7, 8, 9, 10, 11, 12, 13, 14, 15, 16, 17, 18, 19, 20, 21, 22:
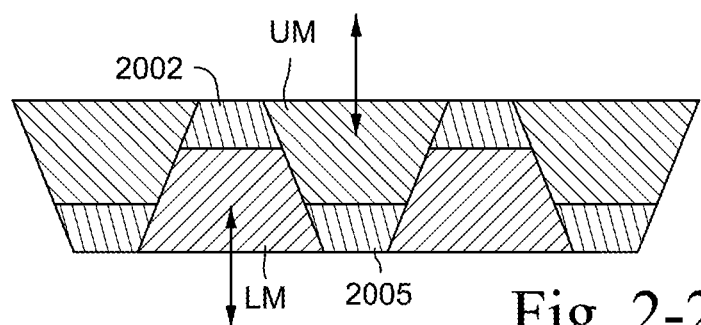
Figures 2, 3, 4, 5, 6, 7, 8, 9, 10, 11, 12, 13, 14, 15, 16, 17, 18, 19, 20, 21, 22, 23:
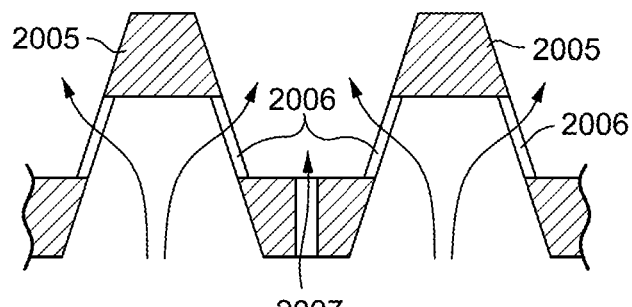
Figures 2, 3, 4, 5, 6, 7, 8, 9, 10, 11, 12, 13, 14, 15, 16, 17, 18, 19, 20, 21, 22, 23, 24:
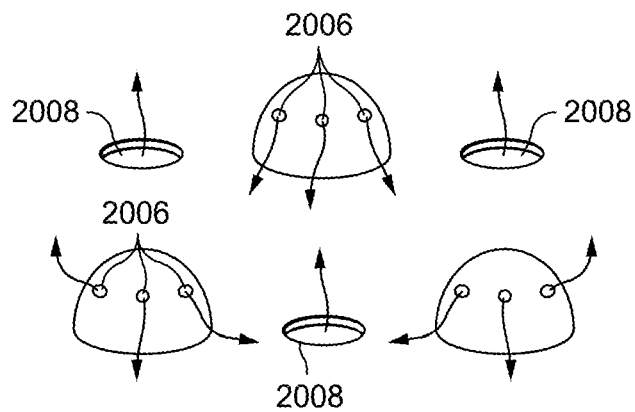
Figures 2, 3, 4, 5, 6, 7, 8, 9, 10, 11, 12, 13, 14, 15, 16, 17, 18, 19, 20, 21, 22, 23, 24, 25:
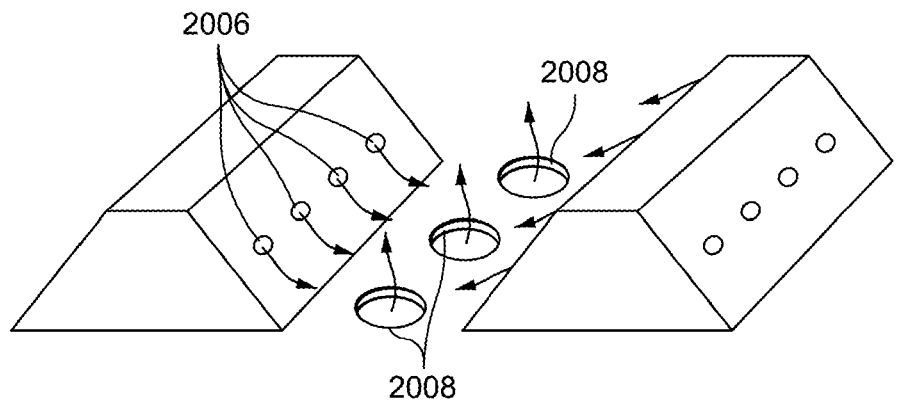
Figures 2, 3, 4, 5, 6, 7, 8, 9, 10, 11, 12, 13, 14, 15, 16, 17, 18, 19, 20, 21, 22, 23, 24, 25, 26:
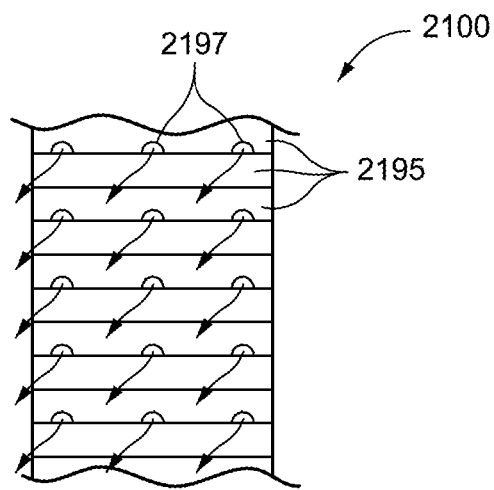

FIGS. 8-1 to 8-3 illustrate a plug-type vent 3600 and frame 3640 according to another embodiment of the present invention. In this embodiment, the plug 3600 and corresponding slot 3642 have a generally v-shaped configuration.

As illustrated, the plug 3600 includes a pair of arms 3608 and a connecting portion 3609 connecting the arms 3608. A plurality of tracks or grooves 3602 are provided to each arm 3608 and extend along the bottom surface and the outer side of each arm. Each arm of the slot 3642 includes an elongated opening 3646 for gas washout.

In use, the grooves 3602 direct vent flow along sides of the frame and avoid exhaust into the patient's eyes. In an alternative embodiment, the grooves may extend along the inner side of each arm 3608 so that exhaust could flow out the inner sides and cause air paths to collide.

FIGS. 9-1 to 9-4 illustrate a plug-type vent 3700 and frame 3740 according to another embodiment of the present invention. In this embodiment, the plug 3700 and corresponding slot 3742 have a generally u-shaped configuration.

As best shown in FIGS. 9-2 and 9-3, the plug 3700 includes a pair of arms 3708 and a bight portion 3709 connecting the arms 3708. Each arm 3708 includes a plurality of tracks or grooves 3702 on one or both sides thereof and a connecting portion 3711 for engaging the frame 3740. In addition, each arm 3708 includes a port cap 3715 extending from the connecting portion 3711 and adapted to engage a respective port 3745 provided in the frame 3740.

The frame 3740 includes a slot 3742 to receive the plug 3700. The bottom wall of the slot 3742 includes one or more openings 3746 for gas washout (see FIG. 9-4). In use, the grooved plug 3700 forms a seal with the slot 3742 so that air can exhaust between the slot walls and the grooves 3702 on the plug 3700.

As shown in FIG. 9-4, the slot walls define an angle α (e.g., in the range of 5-45°, e.g., 10°) which directs the air stream outwards from the slot 3742. Preferably, the angle α is not relatively large so as to direct the air stream onto the patient's chest.

A support beam 3744 is provided in the center of the slot 3742 to maintain spacing between upper and lower slot walls. A groove 3717 is provided in the bight portion 3709 of the plug 3700 to receive at least a portion of the support beam 3744, e.g., to align the plug in the slot and enhance the interference fit. However, it should be appreciated that multiple support beams may be provided. In such embodiment, the support beams should be sufficiently spaced apart from one another so that sufficient exhaust gas can enter the grooves 3702 on the plug 3700 to provide adequate $CO_2$ washout. In an embodiment, baffles may be provided inside the frame to help with $CO_2$ washout.

In the illustrated embodiment, the connecting portion 3711 of each arm includes locking bumps 3713(1), 3713(2) on opposing sides thereof, one of which is adapted to interlock with a retention slot 3747 (see FIGS. 9-1 and 9-2) provided to the frame 3740 along the slot 3742 (i.e., interference fit). A clearance 3749 is provided to the slot 3742 opposite the retention slot 3747 to receive the other of the locking bumps. This arrangement allows the plug 3700 to be assembled in either orientation since the plug is symmetrical. However, alignment markings may be incorporated into the plug and/or frame to facilitate assembly (e.g., alignment dots, arrows).

As illustrated, the plug 3700 is adapted to wrap around and under an inlet opening 3751 provided to the frame 3740. However, the plug may be positioned at other suitable locations on the frame.

In the illustrated embodiment, port caps 3715 are integrated or incorporated into the plug 3700 (e.g., integrally formed in one piece). Such one-piece arrangement reduces the number of mask parts, prevents loss and/or misplacement of parts (e.g., port cap retained to plug when port cap is unplugged from port), and facilitates manufacturing. It should be appreciated that any suitable number of port caps may be provided to the plug. The connecting arm or hinge 3716 connecting each port cap 3715 to the plug 3700 may have any suitable length or thickness (e.g., arm could be wider, thicker, and/or longer), which may depend on material properties and/or desired assembly/disassembly force. The connecting arm 3716 is flexible to allow bending of the connecting arm in the plane of the plug 3700 and/or bending or twisting transverse to the plane of the plug 3700. Also, when removing the port cap 3715 from the respective port 3745, the plug 3700 may be maintained in position within the slot 3742, unless removal of the whole plug is desired.

In an embodiment, the plug 3700 is constructed from a soft and flexible material (e.g., silicone, TPE, rubber) to facilitate attachment to the frame and dampen noise in use. In an embodiment, the plug material may have little to no moisture retention and may not be prone to creep. Also, the plug may be made from an opaque elastomer and/or may be a relatively large part so that the plug is harder for the patient to lose.

In the embodiment, the plug 3700 may be made by two shot molding, i.e., a first shot may be made from a more rigid material to form a skeleton and then a second shot may be made from a softer material. Advantages of such construction include structural integrity of the plug, easier and more accurate assembly/disassembly, and/or soft outside surface to dampen noise. In such embodiment, a polypropylene material may be used.

In an alternative embodiment, the groove 3717 in the bight portion 3709 and the support beam 3744 of the frame 3740 may not be provided, e.g., frame may warp out of shape without the support beam. Also, the groove 3717 is shown as a thin slot, however it may also be a scalloped, wider slot to avoid concentrated stress at the groove.

In addition, the tracks or grooves 3702 along the plug 3700 are relatively thin, however it is possible to extend the length of the bight portion and thus the grooves 3702 may be made wider to allow for sufficient gas flow from the vent. Increasing the size of the bight portion will mean that less or no gas flow is directed towards the chest of the patient in use.

In each embodiment described above, it should be appreciated that the vent component may be provided to any portion of the mask, e.g., a portion of the elbow or a portion of the frame. Also, in each embodiment, the separate vent component may not be completely removable from the mask, e.g., the vent component may be partially removed for cleaning while some part of the vent component is permanently attached to the frame/elbow. This arrangement may reduce the possibility of incorrect assembly and loss of parts.

Also, in an embodiment, the vent component may be retrofit to an existing vent opening in a portion of the mask (e.g., elbow or frame). For example, the vent component (e.g., plug-type vent of FIGS. 7-1 to 7-3 and 8-1 to 8-3) may be suitably sized to be inserted in the vent opening of an existing mask. In another example, the vent component may include a groove around its periphery, the groove adapted to locate the vent component against a correspondingly sized rim of the vent opening in the mask.

In another embodiment, a mask may be provided with a series of replaceable vent components (e.g., series of vent rings or vent plugs) with different venting characteristics (e.g., number of grooves, positioning of grooves, shape of grooves, size of grooves, etc.). This arrangement allows a vent component to be selected from the series to provide a more customized mask system for the patient, e.g., based on treatment requirement, optimal gas washout, venting direction, sound requirement, etc.

While the invention has been described in connection with what are presently considered to be the most practical and preferred embodiments, it is to be understood that the invention is not to be limited to the disclosed embodiments, but on the contrary, is intended to cover various modifications and equivalent arrangements included within the spirit and scope of the invention. Also, the various embodiments described above may be implemented in conjunction with other embodiments, e.g., aspects of one embodiment may be combined with aspects of another embodiment to realize yet other embodiments. Further, each independent feature or component of any given assembly may constitute an additional embodiment. Furthermore, each individual component of any given assembly, one or more portions of an individual component of any given assembly, and various combinations of components from one or more embodiments may include one or more ornamental design features. In addition, while the invention has particular application to patients who suffer from OSA, it is to be appreciated that patients who suffer from other illnesses (e.g., congestive heart failure, diabetes, morbid obesity, stroke, bariatric surgery, etc.) can derive benefit from the above teachings. Moreover, the above teachings have applicability with patients and non-patients alike in non-medical applications.

What is claimed is:

1. A mask system configured to deliver air pressurized by a flow generator system by at least 4 cm $H_2O$ above atmospheric pressure to the airways of a patient to treat sleep disordered breathing (SDB) by continuous positive airway pressure (CPAP) therapy, the mask system comprising:
  an elbow; and
  a vent component provided to the elbow, the vent component configured to discharge gas from a pressurized interior of the elbow to atmosphere during said CPAP therapy,
  the vent component including an annular side wall and a plurality of vent holes for gas washout arranged on the annular side wall, the plurality of vent holes configured to remain open in use at least during the inhalation and exhalation phases of the patient's breathing cycle for the discharge of gas during CPAP therapy,
  wherein the annular side wall comprises a plurality of spaced support walls, and adjacent ones of the plurality of spaced support walls form a respective one of the plurality of vent holes,
  wherein the vent holes are arranged radially on the annular side wall to radially divide exhaust flow over one or more portions totaling at least 90° of a circumference of the annular side wall so as to diffuse the exhaust flow and reduce noise, and
  wherein the elbow includes a baffle configured to divide the elbow into an air delivery passage and an exhaust passage, the exhaust passage arranged to guide washout gas along a flow path to the plurality of vent holes.

2. The mask system according to claim 1, wherein the vent holes are arranged to radially divide exhaust flow up to 180° of the circumference of the annular side wall.

3. The mask system according to claim 1, wherein the vent holes are arranged to radially divide exhaust flow up to 270° of the circumference of the annular side wall.

4. The mask system according to claim 1, wherein the vent holes are arranged to radially divide exhaust flow up to 360° of the circumference of the annular side wall.

5. The mask system according to claim 1, wherein the vent holes are arranged to radially divide exhaust flow in different directions.

6. The mask system according to claim 1, wherein the vent holes are provided along one or more selected arcs or portions of the annular side wall so as to divide exhaust flow along one or more selected arcs or portions of the circumference of the annular side wall.

7. The mask system according to claim 1, wherein the vent holes are arranged to radially divide exhaust flow to avoid direct collision between air exiting adjacent vent holes.

8. The mask system according to claim 1, wherein the vent holes are arranged in only a single row or plane over said one or more portions totaling at least 90° of the circumference of the annular side wall.

9. The mask system according to claim 1, wherein the vent component comprises a base wall and a cap wall that extend parallel to one another, and the annular side wall is arranged between the base wall and the cap wall and extends transverse to the base wall and the cap wall.

10. The mask system according to claim 1, wherein the vent holes are constructed and arranged to allow gas washout while allowing a therapy pressure to be maintained.

11. The mask system according to claim 1, wherein the vent component comprises at least 20 of said vent holes.

12. The mask system according to claim 1, wherein each of the plurality of vent holes provides an open flow path from the pressurized interior to atmosphere during CPAP therapy.

13. The mask system according to claim 1, wherein the plurality of vent holes are configured to continuously discharge exhaled gas during CPAP therapy.

14. A mask system configured to deliver air pressurized by a flow generator system by at least 4 cm $H_2O$ above atmospheric pressure to the airways of a patient to treat sleep disordered breathing (SDB) by continuous positive airway pressure (CPAP) therapy, the mask system comprising:
  a mask component; and
  a vent component provided to the mask component, the vent component configured to discharge gas from a pressurized interior of the mask component to atmosphere during said CPAP therapy,
  the vent component including an annular side wall and a plurality of vent holes for gas washout arranged on the annular side wall, the plurality of vent holes configured to remain open in use at least during the inhalation and exhalation phases of the patient's breathing cycle for the discharge of gas during CPAP therapy,
  wherein the annular side wall comprises a plurality of spaced support walls, and adjacent ones of the plurality of spaced support walls form a respective one of the plurality of vent holes,
  wherein the vent holes are arranged radially on the annular side wall to radially divide exhaust flow over one or more portions totaling at least 90° of a circumference of the annular side wall so as to diffuse the exhaust flow and reduce noise, and
  wherein the vent component comprises an integral one piece construction with the mask component.

15. The mask system according to claim 14, wherein the mask component is an elbow.

16. A mask system configured to deliver air pressurized by a flow generator system by at least 4 cm $H_2O$ above atmospheric pressure to the airways of a patient to treat sleep disordered breathing (SDB) by continuous positive airway pressure (CPAP) therapy, the mask system comprising:
  a mask component; and
  a vent component provided to the mask component, the vent component configured to discharge gas from a pressurized interior of the mask component to atmosphere during said CPAP therapy,
  the vent component including an annular side wall and a plurality of vent holes for gas washout arranged on the annular side wall, the plurality of vent holes configured to remain open in use at least during the inhalation and exhalation phases of the patient's breathing cycle for the discharge of gas during CPAP therapy,
  wherein the annular side wall comprises a plurality of spaced support walls, and adjacent ones of the plurality of spaced support walls form a respective one of the plurality of vent holes,
  wherein the vent holes are arranged radially on the annular side wall to radially divide exhaust flow over one or more portions totaling at least 90° of a circumference of the annular side wall so as to diffuse the exhaust flow and reduce noise, and
  wherein the vent component comprises a cap portion arranged to alter the exhaust flow from a first incoming direction to a second outgoing direction that is sloped or angled to the first incoming direction.

17. The mask system according to claim 16, wherein the mask component is an elbow.

18. The mask system according to claim 16, wherein the second outgoing direction is perpendicular to the first incoming direction.

* * * * *